(12) United States Patent
Senda et al.

(10) Patent No.: US 8,084,559 B2
(45) Date of Patent: Dec. 27, 2011

(54) TRANSITION METAL COMPLEX, PROCESS FOR PRODUCING SAID TRANSITION METAL COMPLEX, SUBSTITUENT-CARRYING FLUORENE COMPOUND, PROCESS FOR PRODUCING SAID FLUORENE COMPOUND, CATALYST COMPONENT FOR OLEFIN POLYMERIZATION, CATALYST FOR OLEFIN POLYMERIZATION, AND PROCESS FOR PRODUCING OLEFIN POLYMER

(75) Inventors: Taichi Senda, Takatsuki (JP); Hidenori Hanaoka, Suita (JP); Shinya Nakahara, Ichihara (JP); Kenji Sogoh, Sodegaura (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 528 days.

(21) Appl. No.: 11/795,967

(22) PCT Filed: Jan. 24, 2006

(86) PCT No.: PCT/JP2006/301390
§ 371 (c)(1),
(2), (4) Date: Jul. 25, 2007

(87) PCT Pub. No.: WO2006/080475
PCT Pub. Date: Aug. 3, 2006

(65) Prior Publication Data
US 2008/0161514 A1 Jul. 3, 2008

(30) Foreign Application Priority Data

Jan. 28, 2005 (JP) ................. 2005-020958
Jan. 28, 2005 (JP) ................. 2005-020963

(51) Int. Cl.
*C08F 4/64* (2006.01)
*C08F 4/76* (2006.01)
*C08F 4/52* (2006.01)
*C07F 17/00* (2006.01)

(52) U.S. Cl. ........ 526/160; 526/170; 526/943; 526/941; 526/129; 526/348; 526/352; 526/134; 556/53; 556/51; 502/113; 502/114

(58) Field of Classification Search ............ 556/51, 556/52, 53; 526/161, 171, 172, 160
See application file for complete search history.

(56) References Cited

U.S. PATENT DOCUMENTS 4,542,199 A 9/1985 Kaminsky et al.
(Continued)

FOREIGN PATENT DOCUMENTS
EP 0 754 698 A2 1/1997
(Continued)

OTHER PUBLICATIONS

Alt, et al., Syndiospezifische Polymerisation von Propylen: Synthese $CH_2$-und CHR—verbrückter fluorenylhaltiger Ligandvorstufen für Metallocenkomplexe des Typs $(C_{13}H_{8-n}R'_nCHR-C_5H_4)ZrCl_2$ (n = 0,2; R = H, Alkyl; R' = H, Hai), Journal of Organometallic Chemistry, vol. 526, pp. 295-301, 1996.

Busico, et al., Syndiotactic Poly(propylene) from [$Me_2Si$(3,6-di-tert-butyl-9-fluorenyl)(N-tert-butyl)]$TiCL_2$—Based Catalysts: Chain-End or Enantiotopic-Sites Stereocontrol, Macromol. Chem. Phys., vol. 204, pp. 1269-1274, 2003.

(Continued)

*Primary Examiner* — Rip A. Lee
(74) *Attorney, Agent, or Firm* — Foley & Lardner LLP

(57) ABSTRACT

A transition metal complex represented by formula [1], and its production process; a substituent-carrying fluorene compound represented by formula [2], and its production process; an olefin polymerization catalyst component comprising the complex; an olefin polymerization catalyst obtained by contacting the catalyst component with a defined aluminum compound and/or a defined boron compound; and a production process of an olefin polymer using the catalyst:

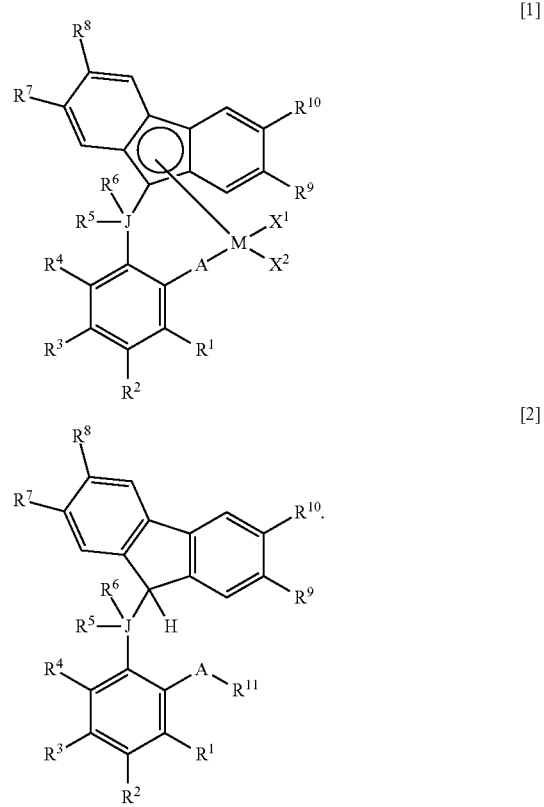

14 Claims, No Drawings

U.S. PATENT DOCUMENTS

| | | | |
|---|---|---|---|
| 6,090,961 A * | 7/2000 | Hanaoka et al. | 556/11 |
| 6,329,478 B1 * | 12/2001 | Katayama et al. | 526/127 |
| 7,211,537 B2 * | 5/2007 | Fujita et al. | 502/150 |
| 7,615,660 B2 * | 11/2009 | Senda et al. | 556/11 |

FOREIGN PATENT DOCUMENTS

| | | |
|---|---|---|
| JP | 4-69394 | 3/1992 |
| JP | 5-51393 | 3/1993 |
| JP | 7-247309 | 9/1995 |
| JP | 2004-155739 | 6/2004 |
| JP | 2004-189869 | 7/2004 |
| WO | WO 92/05204 A1 | 4/1992 |
| WO | WO 97/03992 A1 * | 2/1997 |
| WO | WO 98/02469 A1 * | 1/1998 |
| WO | WO 02/12358 A1 * | 2/2002 |

OTHER PUBLICATIONS

Razavi, et al., Preparation and crystal structures of the complexes ($\eta^5$-$C_5H_3$TMS-$CMe_2$-$\eta^5$-$C_{13}H_8$)$MCl_2$ and [3,6-di'But$C_{13}H_6$-$SiMe_2$-N'Bu]$MCl_2$ (M = Hf, Zr or Ti): mechanistic aspects of the catalytic formation of a isotactic-syndiotactic stereoblock-type polypropylene, Journal of Organometallic Chemistry, vol. 621, pp. 267-276, 2001.

Schmid, et al., Unverbrückte (Pentamethylcyclopentadienyl) (fluorenyl)—Komplexe des Zirconiums und Hafniums. Die Molekülstrukturen von ($C_5Me_5$) (2,7-$Me_2$-$C_{13}H_7$) $MCl_2$ (M = Zr, Hf), Journal of Organometallic Chemistry, vol. 525, pp. 9-14, 1996.

* cited by examiner

TRANSITION METAL COMPLEX, PROCESS FOR PRODUCING SAID TRANSITION METAL COMPLEX, SUBSTITUENT-CARRYING FLUORENE COMPOUND, PROCESS FOR PRODUCING SAID FLUORENE COMPOUND, CATALYST COMPONENT FOR OLEFIN POLYMERIZATION, CATALYST FOR OLEFIN POLYMERIZATION, AND PROCESS FOR PRODUCING OLEFIN POLYMER

CONTINUING DATA

This application is the U.S. national phase of International Application PCT/JP2006/301390, filed on Jan. 24, 2006, claiming priority to JP 2005-020963, filed on Jan. 28, 2005, and JP 2005-020958, filed on Jan. 28, 2005.

TECHNICAL FIELD

The present invention relates to a transition metal complex; a catalyst component for olefin polymerization comprising said transition metal complex; a catalyst for olefin polymerization using said transition metal complex as a catalyst component for olefin polymerization; a process for producing an olefin polymer comprising the step of polymerizing an olefin in the presence of said catalyst for olefin polymerization; a substituent-carrying fluorene compound usable for producing said transition metal complex; a process for producing said substituent-carrying fluorene compound; and a process for producing said transition metal complex using said substituent-carrying fluorene compound.

BACKGROUND ART

Many reports have already been made about a transition metal complex and a process for producing an olefin polymer using said transition metal complex as a catalyst component. Examples of a process for producing an ethylene-based polymer using a high active polymerization catalyst are a process for producing a polyethylene using bis(cyclopentadienyl)zirconium dichloride as a catalyst component (for example, JP 58-19309A); and a process for producing an ethylene-1-hexene copolymer using dimethylsilylene(tetramethylcyclopentadienyl)(3-tert-butyl-5-methyl-2-phenoxy)titanium dichloride as a catalyst component (for example, JP 9-87313A). Also, an example of a process for producing a high molecular weight-carrying propylene-based polymer is a process for producing a polypropylene using 2,7-di-tert-butylfluorenyldimethylsilyl-tert-butylamidotitanium dichloride as a catalyst component (for example, JP 2000-514488T).

However, olefin polymers produced by a process for producing an olefin polymer using the above-mentioned respective transition metal complexes as a catalyst component do not give quite satisfaction in view of height of their molecular weight.

DISCLOSURE OF INVENTION

In view of those circumstances, the present invention has an object to provide a transition metal complex, whose use as a catalyst component for olefin polymerization can polymerize an olefin to produce a high molecular weight olefin polymer; a catalyst component for olefin polymerization comprising said transition metal complex; a catalyst for olefin polymerization using said transition metal complex as a catalyst component for olefin polymerization; a process for producing an olefin polymer comprising the step of polymerizing an olefin in the presence of said catalyst for olefin polymerization; a process for producing said transition metal complex; a substituent-carrying fluorene compound usable for producing said transition metal complex; and a process for producing said substituent-carrying fluorene compound using said substituent-carrying fluorene compound.

The present first invention relates to a transition metal complex represented by the general formula [1]:

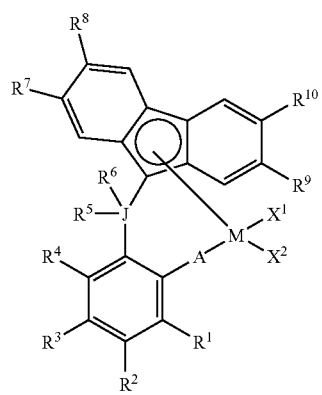

[1]

wherein M is the group 4 transition metal atom in the periodic table of elements; A is the group 16 atom therein; J is the group 14 atom therein; $R^1$, $R^2$, $R^3$, $R^4$, $R^5$, $R^6$, $X^1$ and $X^2$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^1$ and $R^2$, $R^2$ and $R^3$, and $R^3$ and $R^4$ may be linked to each other, respectively, to form respective rings; $R^5$ and $R^6$ may be linked to each other to form a ring; $R^7$, $R^8$, $R^9$ and $R^{10}$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; at least two of $R^7$, $R^8$, $R^9$ and $R^{10}$ are the substituent selected from the above-mentioned group or a halogen atom; $R^7$ and $R^8$ may be linked to each other to form a ring; and $R^9$ and $R^{10}$ may be linked to each other to form a ring.

The present second invention relates to a process for producing a transition metal complex represented by the above-mentioned general formula [1], which comprises the steps of:
(1) reacting a substituent-carrying fluorene compound represented by the general formula [2] with a base; and
(2) further reacting with a transition metal compound represented by the general formula [3],

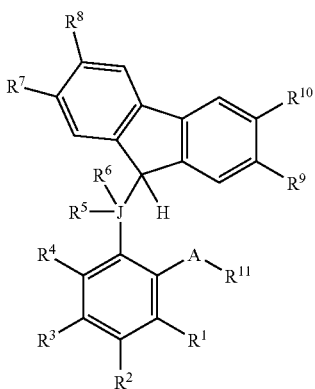

[2]

wherein A is the group 16 atom in the periodic table of elements; J is the group 14 atom therein; $R^1$, $R^2$, $R^3$, $R^4$, $R^5$ and $R^6$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^1$ and $R^2$, $R^2$ and $R^3$, and $R^3$ and $R^4$ may be linked to each other, respectively, to form respective rings; $R^5$ and $R^6$ may be linked to each other to form a ring; $R^7$, $R^8$, $R^9$ and $R^{10}$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; at least two of $R^7$, $R^8$, $R^9$ and $R^{10}$ are the substituent selected from the above-mentioned group or a halogen atom; $R^7$ and $R^8$ may be linked to each other to form a ring; $R^9$ and $R^{10}$ may be linked to each other to form a ring; and $R^{11}$ is a hydrocarbyl group or a three substituent-carrying silyl group, and $$M-X^3_n \qquad [3]$$

wherein M is the group 4 transition metal atom in the periodic table of elements; n is an integer of 3 or 4; $X^3$ is (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying amino group having 1 to 20 carbon atoms, which substituent is a hydrocarbyl group, and said hydrocarbyl group may be substituted by a halogen atom, (1-5) an alkoxy group having 1 to 20 carbon atoms, which may be substituted by a halogen atom, (1-6) an aralkyloxy group having 7 to 20 carbon atoms, which may be substituted by a halogen atom, and (1-7) an aryloxy group having 6 to 20 carbon atoms, which may be substituted by a halogen atom, (2) a halogen atom or (3) a hydrogen atom; and plural $X^3$s are the same as, or different from one another.

The present third invention relates to a substituent-carrying fluorene compound represented by the general formula [2]:

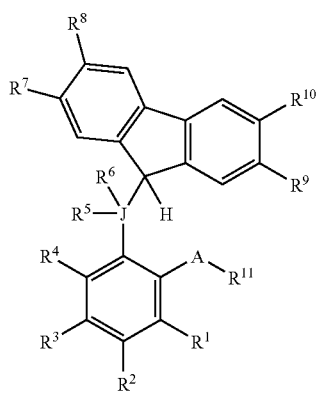

[2]

wherein A is the group 16 atom in the periodic table of elements; J is the group 14 atom therein; $R^1$, $R^2$, $R^3$, $R^4$, $R^5$ and $R^6$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^1$ and $R^2$, $R^2$ and $R^3$, and $R^3$ and $R^4$ may be linked to each other, respectively, to form respective rings; $R^5$ and $R^6$ may be linked to each other to form a ring; $R^7$, $R^8$, $R^9$ and $R^{10}$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; at least two of $R^7$, $R^8$, $R^9$ and $R^{10}$ are the substituent selected from the above-mentioned group or a halogen atom; $R^7$ and $R^8$ may be linked to each other to form a ring; $R^9$ and $R^{10}$ may be linked to each other to form a ring; and $R^{11}$ is a hydrocarbyl group or a three substituent-carrying silyl group.

The present fourth invention relates to a process for producing a substituent-carrying fluorene compound represented by the above-mentioned general formula [2], which comprises the steps of:

(1) reacting a substituent-carrying fluorene compound represented by the general formula [4] with a base; and (2) further reacting with a compound represented by the general formula [5],

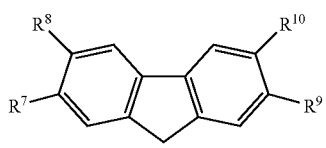

[4]

wherein $R^7$, $R^8$, $R^9$ and $R^{10}$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; at least two of $R^7$, $R^8$, $R^9$ and $R^{10}$ are the substituent selected from the above-mentioned group or a halogen atom; $R^7$ and $R^8$ may be linked to each other to form a ring; and $R^9$ and $R^{10}$ may be linked to each other to form a ring, and

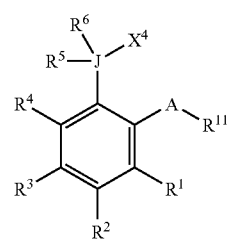

[5]

wherein A is the group 16 atom in the periodic table of elements; J is the group 14 atom therein; $R^1$, $R^2$, $R^3$, $R^4$, $R^5$ and $R^6$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^1$ and $R^2$, $R^2$ and $R^3$, and $R^3$ and $R^4$ may be linked to each other, respectively, to form respective rings; $R^5$ and $R^6$ may be linked to each other to form a ring; $R^{11}$ is a hydrocarbyl group or a three substituent-carrying silyl group; and $X^4$ is a halogen atom.

The present fifth invention relates to a catalyst component for olefin polymerization comprising the above-mentioned transition metal complex.

The present sixth invention relates to a catalyst for olefin polymerization using the above-mentioned transition metal complex as a catalyst component for olefin polymerization.

The present seventh invention relates to a process for producing an olefin polymer using the above-mentioned catalyst for olefin polymerization.

BEST MODE FOR CARRYING OUT THE INVENTION

[Transition Metal Complex]

The transition metal complex of the present invention is the compound represented by the following general formula [1]:

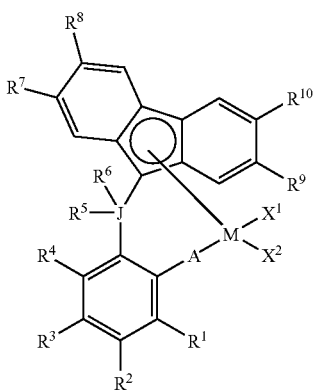

[1]

wherein M is the group 4 transition metal atom in the periodic table of elements according to the revised IUPAC nomenclature of inorganic chemistry (1989), and the below-mentioned periodic table is the same as that; A is the group 16 atom therein; J is the group 14 atom therein; $R^1$, $R^2$, $R^3$, $R^4$, $R^5$, $R^6$, $X^1$ and $X^2$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^1$ and $R^2$, $R^2$ and $R^3$, and $R^3$ and $R^4$ may be linked to each other, respectively, to form respective rings; $R^5$ and $R^6$ may be linked to each other to form a ring; $R^7$, $R^8$, $R^9$ and $R^{10}$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; at least two of $R^7$, $R^8$, $R^9$ and $R^{10}$ are the substituent selected from the above-mentioned group or a halogen atom; $R^7$ and $R^8$ may be linked to each other to form a ring; and $R^9$ and $R^{10}$ may be linked to each other to form a ring.

In the general formula [1], M is the group 4 transition metal atom in the periodic table of elements. Examples of M are a titanium atom, a zirconium atom and a hafnium atom. Among them, preferred is a titanium atom.

In the general formula [1], A is the group 16 atom in the periodic table of elements. Examples of A are an oxygen atom, a sulfur atom and a selenium atom. Among them, preferred is an oxygen atom.

In the general formula [1], J is the group 14 atom in the periodic table of elements. Examples of J are a carbon atom, a silicon atom and a germanium atom. Among them, preferred is a silicon atom or a germanium atom, and more preferred is a silicon atom.

In the general formula [1], $R^1$, $R^2$, $R^3$, $R^4$, $R^5$, $R^6$, $X^1$ and $X^2$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom.

Examples of the alkyl group having 1 to 20 carbon atoms in $R^1$, $R^2$, $R^3$, $R^4$, $R^5$, $R^6$, $X^1$ and $X^2$ are a methyl group, an ethyl group, a n-propyl group, an isopropyl group, a n-butyl group, a sec-butyl group, a tert-butyl group, a n-pentyl group, a neopentyl group, an isopentyl group, a n-hexyl group, a n-heptyl group, a n-octyl group, a n-decyl group, a n-nonyl group, a n-decyl group, a n-dodecyl group, a n-tridecyl group, a n-tetradecyl group, a n-pentadecyl group, a n-hexadecyl group, a n-heptadecyl group, a n-octadecyl group, a n-nonadecyl group, and a n-eicosyl group. Among them, preferred is a methyl group, an ethyl group, an isopropyl group, a tert-butyl group, a n-pentyl group, a neopentyl group or an isopentyl group.

Each of those alkyl groups may be substituted by a halogen atom such as a fluorine atom, a chlorine atom, a bromine atom and an iodine atom. Examples of an alkyl group substituted by a halogen atom and having 1 to 20 carbon atoms are a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, and a perbromoeicosyl group.

Examples of the aralkyl group having 7 to 20 carbon atoms in $R^1$, $R^2$, $R^3$, $R^4$, $R^5$, $R^6$, $X^1$ and $X^2$ are a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-tetradecylphenyl)methyl group, a naphthylmethyl group and an anthracenylmethyl group. Among them, preferred is a benzyl group. Each of those aralkyl groups may be substituted by a halogen atom such as a fluorine atom, a chlorine atom, a bromine atom and an iodine atom.

Examples of the aryl group having 6 to 20 carbon atoms in $R^1$, $R^2$, $R^3$, $R^4$, $R^5$, $R^6$, $X^1$ and $X^2$ are a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group. Among them, preferred is a phenyl group. Each of those aryl groups may be substituted by a halogen atom such as a fluorine atom, a chlorine atom, a bromine atom and an iodine atom.

Examples of the substituent-carrying silyl group having 1 to 20 carbon atoms, which substituent is a hydrocarbyl group, in $R^1$, $R^2$, $R^3$, $R^4$, $R^5$, $R^6$, $X^1$ and $X^2$ are silyl groups substituted by a hydrocarbyl group such as an alkyl group having 1 to 20 carbon atoms (for example, a methyl group, an ethyl group, a n-propyl group, an isopropyl group, a n-butyl group, a sec-butyl group, a tert-butyl group, an isobutyl group, a n-pentyl group, a n-hexyl group, a cyclohexyl group, a n-heptyl group, a n-octyl group, a n-nonyl group, and a n-decyl group) and an aryl group (for example, a phenyl group). Specific examples thereof are a monosubstituent-carrying silyl group such as a methylsilyl group, an ethylsilyl group and a phenylsilyl group; a disubstituent-carrying silyl group such as a dimethylsilyl group, a diethylsilyl group and a diphenylsilyl group; and trisubstituent-carrying silyl group such as a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a triisobutylsilyl group, a tert-butyl-dimethylsilyl group, a tri-n-pentylsilyl group, a tri-n-hexylsilyl group, a tricyclohexylsilyl group, and a triphenylsilyl group. Among them, preferred is a trimethylsilyl group, a tert-butyldimethylsilyl group, or a triphenylsilyl group. Hydrocarbyl groups contained in each of those substituent-carrying silyl groups may be substituted by a halogen atom such as a fluorine atom, a chlorine atom, a bromine atom and an iodine atom.

Examples of the disubstituent-carrying amino group having 2 to 20 carbon atoms, which substituent is a hydrocarbyl group, in $R^1$, $R^2$, $R^3$, $R^4$, $R^5$, $R^6$, $X^1$ and $X^2$ are amino groups substituted by two hydrocarbyl groups such as an alkyl group having 1 to 20 carbon atoms (for example, a methyl group, an ethyl group, a n-propyl group, an isopropyl group, a n-butyl group, a sec-butyl group, a tert-butyl group, an isobutyl group, a n-pentyl group, a n-hexyl group, and a cyclohexyl group) and an aryl group (for example, a phenyl group). Specific examples thereof are a dimethylamino group, a diethylamino group, a di-n-propylamino group, a diisopropylamino group, a di-n-butylamino group, a di-sec-butylamino group, a di-tert-butylamino group, a diisobutylamino group, a tert-butylisopropylamino group, a di-n-hexylamino group, a di-n-octylamino group, a di-n-decylamino group, a diphenylamino group, a pyrrolyl group, a pyrrolidinyl group, a piperidinyl group, a carbazolyl group, and a dihydroisoindolyl group. Among them, preferred is a dimethylamino group, a diethylamino group, a pyrrolidinyl group, or a piperidinyl group.

Examples of the alkoxy group having 1 to 20 carbon atoms in $R^1$, $R^2$, $R^3$, $R^4$, $R^5$, $R^6$, $X^1$ and $X^2$ are a methoxy group, an ethoxy group, a n-propoxy group, an isopropoxy group, a n-butoxy group, a sec-butoxy group, a tert-butoxy group, a n-pentyloxy group, a neopentyloxy group, a n-hexyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group, and a n-eicosoxy group. Among them, preferred is a methoxy group, an ethoxy group, an isopropoxy group, or a tert-butoxy group. Each of those alkoxy groups may be substituted by a halogen atom such as a fluorine atom, a chlorine atom, a bromine atom and an iodine atom.

Examples of the aralkyloxy group having 7 to 20 carbon atoms in $R^1$, $R^2$, $R^3$, $R^4$, $R^5$, $R^6$, $X^1$ and $X^2$ are a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a (n-tetradecylphenyl)methoxy group, a naphthylmethoxy group, and an anthracenylmethoxy group. Among them, preferred is a benzyloxy group. Each of those aralkyloxy groups may be substituted by a halogen atom such as a fluorine atom, a chlorine atom, a bromine atom and an iodine atom.

Examples of the aryloxy group having 6 to 20 carbon atoms in $R^1$, $R^2$, $R^3$, $R^4$, $R^5$, $R^6$, $X^1$ and $X^2$ are a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group and an anthracenoxy group. Among them, preferred is a phenoxy group. Each of those aryloxy groups may be substituted by a halogen atom such as a fluorine atom, a chlorine atom, a bromine atom and an iodine atom.

Examples of the halogen atom in $R^1$, $R^2$, $R^3$, $R^4$, $R^5$, $R^6$, $X^1$ and $X^2$ are a fluorine atom, a chlorine atom, a bromine atom and an iodine atom. Among them, preferred is a fluorine atom, a chlorine atom, or a bromine atom, and more preferred is a chlorine atom.

$R^1$ and $R^2$, $R^2$ and $R^3$, and $R^3$ and $R^4$ may be linked to each other, respectively, to form respective rings, and $R^5$ and $R^6$ may be linked to each other to form a ring. Examples of said ring are a saturated hydrocarbon ring and an unsaturated hydrocarbon ring. Specific examples of said ring are a cyclopropane ring, a cyclobutane ring, a cyclopentane ring, a cyclohexane ring, a cycloheptane ring, a cyclooctane ring, a benzene ring, a naphthalene ring, and an anthracene ring. Those rings may be substituted by a group such as a hydrocarbyl group having 1 to 20 carbon atoms.

$R^1$ is preferably a substituent-carrying silyl group having 1 to 20 carbon atoms, which substituent is a hydrocarbyl group; an alkyl group having 1 to 20 carbon atoms; an aralkyl group having 7 to 20 carbon atoms; or an aryl group having 6 to 20 carbon atoms.

$R^5$ and $R^6$ are preferably an alkyl group having 1 to 20 carbon atoms; an aralkyl group having 7 to 20 carbon atoms; or an aryl group having 6 to 20 carbon atoms. Further, it is preferable that at least one of $R^5$ and $R^6$ is an ethyl group, and it is more preferable that both $R^5$ and $R^6$ are an ethyl group.

$X^1$ and $X^2$ are preferably a halogen atom; an alkyl group having 1 to 20 carbon atoms; an aralkyl group having 7 to 20 carbon atoms; a disubstituent-carrying amino group having 2 to 20 carbon atoms, which substituent is a hydrocarbyl group; an alkoxy group having 1 to 20 carbon atoms; or an aryloxy group having 6 to 20 carbon atoms; and more preferably a fluorine atom, a chlorine atom, a bromine atom, a methyl group, a tert-butyl group, a benzyl group, a dimethylamino group, a diethylamino group, a methoxy group, an ethoxy group, an isopropoxy group, a tert-butoxy group or a phenoxy group.

In the general formula [1], $R^7$, $R^8$, $R^9$ and $R^{10}$ are independently of one another (1) a substituent selected from the group consisting of (1-1) an alkyl group having 1 to 20 carbon atoms, (1-2) an aralkyl group having 7 to 20 carbon atoms, (1-3) an aryl group having 6 to 20 carbon atoms, (1-4) a substituent-carrying silyl group having 1 to 20 carbon atoms, which substituent is a hydrocarbyl group, (1-5) a disubstituent-carrying amino group having 2 to 20 carbon atoms, which substituent is a hydrocarbyl group, (1-6) an alkoxy group having 1 to 20 carbon atoms, (1-7) an aralkyloxy group having 7 to 20 carbon atoms, and (1-8) an aryloxy group having 6 to 20 carbon atoms, (2) a halogen atom or (3) a hydrogen atom.

Examples of the alkyl group having 1 to 20 carbon atoms in $R^7$, $R^8$, $R^9$ and $R^{10}$ are a methyl group, an ethyl group, a n-propyl group, an isopropyl group, a n-butyl group, a sec-butyl group, a tert-butyl group, a n-pentyl group, a neopentyl group, an isopentyl group, a n-hexyl group, a n-octyl group, a n-decyl group, a n-dodecyl group, a n-pentadecyl group, and a n-eicosyl group. Among them, preferred is a methyl group, an ethyl group, an isopropyl group, a tert-butyl group, a n-pentyl group, a neopentyl group or an isopentyl group; more preferred is a methyl group, an ethyl group or a tert-butyl group; and further preferred is a tert-butyl group.

Each of those alkyl groups may be substituted by a halogen atom such as a fluorine atom, a chlorine atom, a bromine atom and an iodine atom. Examples of an alkyl group substituted by a halogen atom, and having 1 to 20 carbon atoms are a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, and a perbromoeicosyl group.

Examples of the aralky group having 7 to 20 carbon atoms in $R^7$, $R^8$, $R^9$ and $R^{10}$ are a benzyl group, a (2-methylphenyl) methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl) methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-tetradecylphenyl)methyl group, a naphthylmethyl group and an anthracenylmethyl group. Among them, preferred is a benzyl group. Each of those aralkyl groups may be substituted by a halogen atom such as a fluorine atom, a chlorine atom, a bromine atom and an iodine atom.

Examples of the aryl group having 6 to 20 carbon atoms in $R^7$, $R^8$, $R^9$ and $R^{10}$ are a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group. Among them, preferred is a phenyl group. Each of those aryl groups may be substituted by a halogen atom such as a fluorine atom, a chlorine atom, a bromine atom and an iodine atom.

Examples of the substituent-carrying silyl group having 1 to 20 carbon atoms, which substituent is a hydrocarbyl group, in $R^7$, $R^8$, $R^9$ and $R^{10}$ are silyl groups substituted by a hydrocarbyl group such as an alkyl group having 1 to 20 carbon atoms (for example, a methyl group, an ethyl group, a n-propyl group, an isopropyl group, a n-butyl group, a sec-butyl group, a tert-butyl group, an isobutyl group, a n-pentyl group, a n-hexyl group, a cyclohexyl group) and an aryl group (for example, a phenyl group). Specific examples thereof are a monosubstituent-carrying silyl group such as a methylsilyl group, an ethylsilyl group and a phenylsilyl group; a disubstituent-carrying silyl group such as a dimethylsilyl group, a diethylsilyl group and a diphenylsilyl group; and trisubstituent-carrying silyl group such as a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a triisobutylsilyl group, a tert-butyldimethylsilyl group, a tri-n-pentylsilyl group, a tri-n-hexylsilyl group, a tricyclohexylsilyl group, and a triphenylsilyl group. Among them, preferred is a trimethylsilyl group, a tert-butyldimethylsilyl group, or a triphenylsilyl group. Hydrocarbyl groups contained in each of those substituent-carrying silyl groups may be substituted by a halogen atom such as a fluorine atom, a chlorine atom, a bromine atom and an iodine atom.

Examples of the disubstituent-carrying amino group having 2 to 20 carbon atoms, which substituent is a hydrocarbyl group, in $R^7$, $R^8$, $R^9$ and $R^{10}$ are amino groups substituted by two hydrocarbyl groups such as an alkyl group having 1 to 20 carbon atoms (for example, a methyl group, an ethyl group, a n-propyl group, an isopropyl group, a n-butyl group, a sec-butyl group, a tert-butyl group, an isobutyl group, a n-pentyl group, a n-hexyl group, and a cyclohexyl group) and an aryl group (for example, a phenyl group). Specific examples thereof are a dimethylamino group, a diethylamino group, a di-n-propylamino group, a diisopropylamino group, a di-n-butylamino group, a di-sec-butylamino group, a di-tert-butylamino group, a diisobutylamino group, a tert-butylisopropylamino group, a di-n-hexylamino group, a di-n-octylamino group, a di-n-decylamino group, a diphenylamino group, a bistrimethylsilylamino group, and a bis-tert-butyldimethylsilylamino group. Among them, preferred is a dimethylamino group or a diethylamino group.

Examples of the alkoxy group having 1 to 20 carbon atoms in $R^7$, $R^8$, $R^9$ and $R^{10}$ are a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group, and a n-eicosoxy group. Among them, preferred is a methoxy group, an ethoxy group, or a tert-butoxy group. Each of those alkoxy groups may be substituted by a halogen atom such as a fluorine atom, a chlorine atom, a bromine atom and an iodine atom.

Examples of the aralkyloxy group having 7 to 20 carbon atoms in $R^7$, $R^8$, $R^9$ and $R^{10}$ are a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl) methoxy group, a (n-tetradecylphenyl)methoxy group, a naphthylmethoxy group, and an anthracenylmethoxy group. Among them, preferred is a benzyloxy group. Each of those aralkyloxy groups may be substituted by a halogen atom such as a fluorine atom, a chlorine atom, a bromine atom and an iodine atom.

Examples of the aryloxy group having 6 to 20 carbon atoms in $R^7$, $R^8$, $R^9$ and $R^{10}$ are a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group and an anthracenoxy group. Among them, preferred is a phenoxy group. Each of those aryloxy groups may be substituted by a halogen atom such as a fluorine atom, a chlorine atom, a bromine atom and an iodine atom.

Examples of the halogen atom in $R^7$, $R^8$, $R^9$ and $R^{10}$ are a fluorine atom, a chlorine atom, a bromine atom and an iodine atom.

$R^7$ and $R^8$ may be linked to each other to form a ring, and $R^9$ and $R^1$ may be linked to each other to form a ring. Examples of said ring are a saturated hydrocarbon ring and an unsaturated hydrocarbon ring. Specific examples of said ring are a cyclopropane ring, a cyclobutane ring, a cyclopentane ring, a cyclohexane ring, a cycloheptane ring, a cyclooctane ring, a benzene ring, a naphthalene ring, and an anthracene ring. Those rings may be substituted by a group such as a hydrocarbyl group having 1 to 20 carbon atoms.

The substituent and the halogen atom in $R^7$, $R^8$, $R^9$ and $R^{10}$ are preferably an alkyl group having 1 to 20 carbon atoms; an aryl group having 6 to 20 carbon atoms; a substituent-carrying silyl group having 1 to 20 carbon atoms, which substituent is a hydrocarbyl group; a disubstituent-carrying amino group having 2 to 20 carbon atoms, which substituent is a hydrocarbyl group; an alkoxy group having 1 to 20 carbon atoms; or a halogen atom, more preferably an alkyl group having 1 to 20 carbon atoms; an aryl group having 6 to 20 carbon atoms; a substituent-carrying silyl group having 1 to 20 carbon atoms, which substituent is a hydrocarbyl group; or a halogen atom, further preferably a tert-butyl group; a phenyl group; a trimethylsilyl group; or a chlorine atom, and most preferably a tert-butyl group.

At least two of $R^7$, $R^8$, $R^9$ and $R^{10}$ are the above-mentioned substituent or a halogen atom. Combinations of two of $R^7$, $R^8$, $R^9$ and $R^{10}$ satisfying said requirement are a combination of $R^7$ and $R^8$, that of $R^9$ and $R^{10}$, that of $R^7$ and $R^9$, that of $R^8$ and $R^{10}$, that of $R^7$ and $R^{10}$, and that of $R^8$ and $R^9$; combinations of three thereof satisfying said requirement are a combination of $R^7$, $R^8$ and $R^9$, that of $R^7$, $R^8$ and $R^{10}$, that of $R^7$, $R^9$ and $R^{10}$, and that of $R^8$, $R^9$ and $R^{10}$; and a combination of four thereof satisfying said requirement are a combination of $R^7$, $R^8$, $R^9$ and $R^{10}$. Among them, preferred are combinations of two of $R^7$, $R^8$, $R^9$ and $R^{10}$.

Whether each of $R^7$, $R^8$, $R^9$ and $R^{10}$ is the above-mentioned substituent or a halogen atom is determined by the kind of an olefin, which is polymerized by a catalyst for olefin polymerization using the transition metal complex represented by the general formula [1] as a catalyst component for olefin polymerization. It is preferable, for example, that $R^7$ and $R^9$ are said substituent or a halogen atom for copolymerization of ethylene with an α-olefin. For copolymerization of ethylene with a cyclic olefin, it is preferable that at least one of $R^8$ and $R^{10}$ is said substituent or a halogen atom, and more preferable that both $R^8$ and $R^{10}$ are said substituent or a halogen atom.

Coordination number, η, in the bond between M and the fluorenyl group in the general formula [1] is not particularly limited, and η is any number which the fluorenyl group can take. Examples of η are η5-coordination, η4-coordination, η3-coordination, η2-coordination, and η1-coordination, and preferably η5-coordination, η3-coordination or, η1-coordination, and more preferably η5-coordination or η3-coordination.

Examples of the transition metal complex represented by the general formula [1] are compounds mentioned below, wherein substitution positions on a fluorenyl ring are indicated by the numbers represented by the following formula,

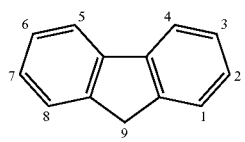

substitution positions on a benzofluorenyl ring are indicated by the numbers represented by the following formula, and

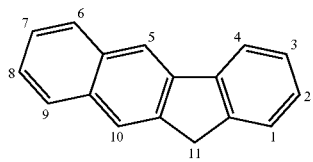

substitution positions on a dibenzofluorenyl ring are indicated by the numbers represented by the following formula,

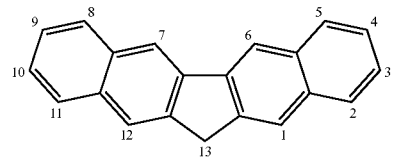

diethylsilylene(2,7-di-tert-butylfluoren-9-yl)(2-phenoxy)titanium dichloride, diethylsilylene(2,7-di-tert-butylfluoren-9-yl)(3,4-dimethyl-2-phenoxy)titanium dichloride, diethylsilylene(2,7-di-tert-butylfluoren-9-yl)(3-tert-butyl-5-methyl-2-phenoxy)titanium dichloride, diethylsilylene(2,7-di-tert-butylfluoren-9-yl)(3-tert-butyl-5-methoxy-2-phenoxy)titanium dichloride, diethylsilylene(2,7-di-tert-butylfluoren-9-yl)(3-tert-butyl-5-dimethylamino-2-phenoxy)titanium dichloride, diethylsilylene(2,7-di-tert-butylfluoren-9-yl)(3-tert-butyl-2-phenoxy)titanium dichloride, diethylsilylene(2,7-di-tert-butylfluoren-9-yl)(3-tert-butyl-5-chloro-2-phenoxy)titanium dichloride, diethylsilylene(2,7-di-tert-butylfluoren-9-yl)(3-phenyl-2-phenoxy)titanium dichloride, diethylsilylene(2,7-di-tert-butylfluoren-9-yl)(3-tert-butyldimethylsilyl-5-methyl-2-phenoxy)titanium dichloride, diethylsilylene(2,7-di-tert-butylfluoren-9-yl)(3-trimethylsilyl-5-methyl-2-phenoxy)titanium dichloride, diethylsilylene(2,7-di-tert-butylfluoren-9-yl)(2-naphthoxy)titanium dichloride, diethylsilylene(2,7-diphenylfluoren-9-yl)(2-phenoxy)titanium dichloride, diethylsilylene(2,7-diphenylfluoren-9-yl)(3,4-dimethyl-2-phenoxy)titanium dichloride, diethylsilylene(2,7-diphenylfluoren-9-yl)(3-tert-butyl-5-methyl-2-phenoxy)titanium dichloride, diethylsilylene(2,7-diphenylfluoren-9-yl)(3-tert-butyl-5-methoxy-2-phenoxy)titanium dichloride, diethylsilylene(2,7-diphenylfluoren-9-yl)(3-tert-butyl-5-dimethylamino-2-phenoxy)titanium dichloride, diethylsilylene(2,7-diphenylfluoren-9-yl)(3-tert-butyl-2-phenoxy)titanium dichloride, diethylsilylene(2,7-diphenylfluoren-9-yl)(3-tert-butyl-5-chloro-2-phenoxy)titanium dichloride, diethylsilylene(2,7-diphenylfluoren-9-yl)(3-phenyl-2-phenoxy)titanium dichloride, diethylsilylene(2,7-diphenylfluoren-9-yl)(3-tert-butyldimethylsilyl-5-methyl-2-phenoxy)titanium dichloride, diethylsilylene(2,7-diphenylfluoren-9-yl)(3-trimethylsilyl-5-methyl-2-phenoxy)titanium dichloride, diethylsilylene(2,7-diphenylfluoren-9-yl)(2-naphthoxy)titanium dichloride, diethylsilylene{(2,7-bis(trimethylsilyl)fluoren-9-yl}(2-phenoxy)titanium dichloride, diethylsilylene{2,7-bis(trimethylsilyl)fluoren-9-yl}(3,4-dimethyl-2-phenoxy)titanium dichloride, diethylsilylene{2,7-bis(trimethylsilyl)fluoren-9-yl}(3-tert-butyl-5-methyl-2-phenoxy)titanium dichloride, diethylsilylene{2,7-bis(trimethylsilyl)fluoren-9-yl}(3-tert-butyl-5-methoxy-2-phenoxy)titanium dichloride, diethylsilylene{2,7-bis(trimethylsilyl)fluoren-9-yl}(3-tert-butyl-5-dimethylamino-2-phenoxy)titanium dichloride, diethylsilylene{2,7-bis(trimethylsilyl)fluoren-9-yl}(3-tert-butyl-2-phenoxy)titanium dichloride, diethylsilylene{2,7-bis(trimethylsilyl)fluoren-9-yl}(3-tert-butyl-5-chloro-2-phenoxy)titanium dichloride, diethylsilylene{2,7-bis(trimethylsilyl)fluoren-9-yl}(3-phenyl-2-phenoxy)titanium dichloride, diethylsilylene{2,7-bis(trimethylsilyl)fluoren-9-yl}(3-tert-butyldimethylsilyl-5-methyl-2-phenoxy)titanium dichloride, diethylsilylene{2,7-bis(trimethylsilyl)fluoren-9-yl}(3-trimethylsilyl-5-methyl-2-phenoxy)titanium dichloride, diethylsilylene{2,7-bis(trimethylsilyl)fluoren-9-yl}(2- naphthoxy)titanium dichloride, diethylsilylene{2,7-bis(dimethylamino)fluoren-9-yl}(2-phenoxy)titanium dichloride, diethylsilylene{2,7-bis(dimethylamino)fluoren-9-yl}(3,4-dimethyl-2-phenoxy)titanium dichloride, diethylsilylene{(3,6-bis(dimethylamino)fluoren-9-yl}(3-tert-butyl-5-methyl-2-phenoxy)titanium dichloride, diethylsilylene{2,7-bis(dimethylamino)fluoren-9-yl}(3-tert-butyl-5-methoxy-2-phenoxy)titanium dichloride, diethylsilylene{2,7-bis(dimethylamino)fluoren-9-yl}(3-tert-butyl-5-dimethylamino-2-phenoxy)titanium dichloride, diethylsilylene{2,7-bis(dimethylamino)fluoren-9-yl}(3-tert-butyl-2-phenoxy)titanium dichloride, diethylsilylene{2,7-bis(dimethylamino)fluoren-9-yl}(3-tert-butyl-5-chloro-2-phenoxy)titanium dichloride, diethylsilylene{2,7-bis(dimethylamino)fluoren-9-yl}(3-phenyl-2-phenoxy)titanium dichloride, diethylsilylene{2,7-bis(dimethylamino)fluoren-9-yl}(3-tert-butyldimethylsilyl-5-methyl-2-phenoxy)titanium dichloride, diethylsilylene{2,7-bis(dimethylamino)fluoren-9-yl}(3-trimethylsilyl-5-methyl-2-phenoxy)titanium dichloride, diethylsilylene{2,7-bis(dimethylamino)fluoren-9-yl}(2-naphthoxy)titanium dichloride, diethylsilylene(2,7-dimethoxyfluoren-9-yl)(2-phenoxy)titanium dichloride, diethylsilylene(2,7-dimethoxyfluoren-9-yl)(3,4-dimethyl-2-phenoxy)titanium dichloride, diethylsilylene(2,7-dimethoxyfluoren-9-yl)(3-tert-butyl-5-methyl-2-phenoxy)titanium dichloride, diethylsilylene(2,7-dimethoxyfluoren-9-yl)(3-tert-butyl-5-methoxy-2-phenoxy)titanium dichloride, diethylsilylene(2,7-dimethoxyfluoren-9-yl)(3-tert-butyl-5-dimethylamino-2-phenoxy)titanium dichloride, diethylsilylene(2,7-dimethoxyfluoren-9-yl)(3-tert-butyl-2-phenoxy)titanium dichloride, diethylsilylene(2,7-dimethoxyfluoren-9-yl)(3-tert-butyl-5-chloro-2-phenoxy)titanium dichloride, diethylsilylene(2,7-dimethoxyfluoren-9-yl)(3-phenyl-2-phenoxy)titanium dichloride, diethylsilylene(2,7-dimethoxyfluoren-9-yl)(3-tert-butyldimethylsilyl-5-methyl-2-phenoxy)titanium dichloride, diethylsilylene(2,7-dimethoxyfluoren-9-yl)(3-trimethylsilyl-5-methyl-2-phenoxy)titanium dichloride, diethylsilylene(2,7-dimethoxyfluoren-9-yl)(2-naphthoxy)titanium dichloride, diethylsilylene(2,7-dichlorofluoren-9-yl)(2-phenoxy)titanium dichloride, diethylsilylene(2,7-dichlorofluoren-9-yl)(3,4-dimethyl-2-phenoxy)titanium dichloride, diethylsilylene(2,7-dichlorofluoren-9-yl)(3-tert-butyl-5-methyl-2-phenoxy)titanium dichloride, diethylsilylene(2,7-dichlorofluoren-9-yl)(3-tert-butyl-5-methoxy-2-phenoxy)titanium dichloride, diethylsilylene(2,7-dichlorofluoren-9-yl)(3-tert-butyl-5-dimethylamino-2-phenoxy)titanium dichloride, diethylsilylene(2,7-dichlorofluoren-9-yl)(3-tert-butyl-2-phenoxy)titanium dichloride, diethylsilylene(2,7-dichlorofluoren-9-yl)(3-tert-butyl-5-chloro-2-phenoxy)titanium dichloride, diethylsilylene(2,7-dichlorofluoren-9-yl)(3-phenyl-2-phenoxy)titanium dichloride, diethylsilylene(2,7-dichlorofluoren-9-yl)(3-tert-butyldimethylsilyl-5-methyl-2-phenoxy)titanium dichloride, diethylsilylene(2,7-dichlorofluoren-9-yl)(3-trimethylsilyl-5-methyl-2-phenoxy)titanium dichloride, diethylsilylene(2,7-dichlorofluoren-9-yl)(2-naphthoxy)titanium dichloride, diethylsilylene(3,6-di-tert-butylfluoren-9-yl)(2-phenoxy)titanium dichloride, diethylsilylene(3,6-di-tert-butylfluoren-9-yl)(3,4-dimethyl-2-phenoxy)titanium dichloride, diethylsilylene(3,6-di-tert-butylfluoren-9-yl)(3-tert-butyl-5-methyl-2-phenoxy)titanium dichloride, diethylsilylene(3,6-di-tert-butylfluoren-9-yl)(3-tert-butyl-5-methoxy-2-phenoxy)titanium dichloride, diethylsilylene(3,6-di-tert-butylfluoren-9-yl)(3-tert-butyl-5-dimethylamino-2-phenoxy)titanium dichloride, diethylsilylene(3,6-di-tert-butylfluoren-9-yl)(3-tert-butyl-2-phenoxy)titanium dichloride, diethylsilylene(3,6-di-tert-butylfluoren-9-yl)(3-tert-butyl-5-chloro-2-phenoxy)titanium dichloride, diethylsilylene(3,6-di-tert-butylfluoren-9-yl)(3-phenyl-2-phenoxy)titanium dichloride, diethylsilylene(3,6-di-tert-butylfluoren-9-yl)(3-tert-butyldimethylsilyl-5-methyl-2-phenoxy)titanium dichloride, diethylsilylene(3,6-di-tert-butylfluoren-9-yl)(3-trimethylsilyl-5-methyl-2-phenoxy)titanium dichloride, diethylsilylene(3,6-di-tert-butylfluoren-9-yl)(2-naphthoxy)titanium dichloride, diethylsilylene(3,6-diphenylfluoren-9-yl)(2-phenoxy)titanium dichloride, diethylsilylene(3,6-diphenylfluoren-9-yl)(3,4-dimethyl-2-phenoxy)titanium dichloride, diethylsilylene(3,6-diphenylfluoren-9-yl)(3-tert-butyl-5-methyl-2-phenoxy)titanium dichloride, diethylsilylene(3,6-diphenylfluoren-9-yl)(3-tert-butyl-5-methoxy-2-phenoxy)titanium dichloride, diethylsilylene(3,6-diphenylfluoren-9-yl)(3-tert-butyl-5-dimethylamino-2-phenoxy)titanium dichloride, diethylsilylene(3,6-diphenylfluoren-9-yl)(3-tert-butyl-2-phenoxy)titanium dichloride, diethylsilylene(3,6-diphenylfluoren-9-yl)(3-tert-butyl-5-chloro-2-phenoxy)titanium dichloride, diethylsilylene(3,6-diphenylfluoren-9-yl)(3-phenyl-2-phenoxy)titanium dichloride, diethylsilylene(3,6-diphenylfluoren-9-yl)(3-tert-butyldimethylsilyl-5-methyl-2-phenoxy)titanium dichloride, diethylsilylene(3,6-diphenylfluoren-9-yl)(3-trimethylsilyl-5-methyl-2-phenoxy)titanium dichloride, diethylsilylene(3,6-diphenylfluoren-9-yl)(2-naphthoxy)titanium dichloride, diethylsilylene{3,6-bis(trimethylsilyl)fluoren-9-yl}(2-phenoxy)titanium dichloride, diethylsilylene{3,6-bis(trimethylsilyl)fluoren-9-yl}(3,4-dimethyl-2-phenoxy)titanium dichloride, diethylsilylene{3,6-bis(trimethylsilyl)fluoren-9-yl}(3-tert-butyl-5-methyl-2-phenoxy)titanium dichloride, diethylsilylene{3,6-bis(trimethylsilyl)fluoren-9-yl}(3-tert-butyl-5-methoxy-2-phenoxy)titanium dichloride, diethylsilylene{3,6-bis(trimethylsilyl)fluoren-9-yl}(3-tert-butyl-5-dimethylamino-2-phenoxy)titanium dichloride, diethylsilylene{3,6-bis(trimethylsilyl)fluoren-9-yl}(3-tert-butyl-2-phenoxy)titanium dichloride, diethylsilylene{3,6-bis(trimethylsilyl)fluoren-9-yl}(3-tert-butyl-5-chloro-2-phenoxy)titanium dichloride, diethylsilylene{3,6-bis(trimethylsilyl)fluoren-9-yl}(3-phenyl-2-phenoxy)titanium dichloride, diethylsilylene{3,6-bis(trimethylsilyl)fluoren-9-yl}(3-tert-butyldimethylsilyl-5-methyl-2-phenoxy)titanium dichloride, diethylsilylene{3,6-bis(trimethylsilyl)fluoren-9-yl}(3-trimethylsilyl-5-methyl-2-phenoxy)titanium dichloride, diethylsilylene{3,6-bis(trimethylsilyl)fluoren-9-yl}(2-naphthoxy)titanium dichloride, diethylsilylene{3,6-bis(dimethylamino)fluoren-9-yl}(2-phenoxy)titanium dichloride, diethylsilylene{3,6-bis(dimethylamino)fluoren-9-yl}(3,4-dimethyl-2-phenoxy)titanium dichloride, diethylsilylene{3,6-bis(dimethylamino)fluoren-9-yl}(3-tert-butyl-5-methyl-2-phenoxy)titanium dichloride, diethylsilylene{3,6-bis(dimethylamino)fluoren-9-yl}(3-tert-butyl-5-methoxy-2-phenoxy)titanium dichloride, diethylsilylene{3,6-bis(dimethylamino)fluoren-9-yl}(3-tert-butyl-5-dimethylamino-2-phenoxy)titanium dichloride, diethylsilylene{3,6-bis(dimethylamino)fluoren-9-yl}(3-tert-butyl-2-phenoxy)titanium dichloride, diethylsilylene{3,6-bis(dimethylamino)fluoren-9-yl}(3-tert-butyl-5-chloro-2-phenoxy)titanium dichloride, diethylsilylene{3,6-bis(dimethylamino)fluoren-9-yl}(3-phenyl-2-phenoxy)titanium dichloride, diethylsilylene{3,6-bis(dimethylamino)fluoren-9-yl}(3-tert-butyldimethylsilyl-5-methyl-2-phenoxy)titanium dichloride, diethylsilylene{3,6-bis(dimethylamino)fluoren-9-yl}(3-trimethylsilyl-5-methyl-2-phenoxy)titanium dichloride, diethylsilylene(3,6-bis(dimethylamino)fluoren-9-yl)(2-naphthoxy)titanium dichloride, diethylsilylene{3,6-dimethoxyfluoren-9-yl}(2- phenoxy)titanium dichloride, diethylsilylene(3,6-dimethoxyfluoren-9-yl)(3,4-dimethyl-2-phenoxy)titanium dichloride, diethylsilylene(3,6-dimethoxyfluoren-9-yl)(3-tert-butyl-5-methyl-2-phenoxy)titanium dichloride, diethylsilylene(3,6-dimethoxyfluoren-9-yl)(3-tert-butyl-5-methoxy-2-phenoxy)titanium dichloride, diethylsilylene(3,6-dimethoxyfluoren-9-yl)(3-tert-butyl-5-dimethylamino-2-phenoxy)titanium dichloride, diethylsilylene(3,6-dimethoxyfluoren-9-yl)(3-tert-butyl-2-phenoxy)titanium dichloride, diethylsilylene(3,6-dimethoxyfluoren-9-yl)(3-tert-butyl-5-chloro-2-phenoxy)titanium dichloride, diethylsilylene(3,6-dimethoxyfluoren-9-yl)(3-phenyl-2-phenoxy) titanium dichloride, diethylsilylene(3,6-dimethoxyfluoren-9-yl)(3-tert-butyldimethylsilyl-5-methyl-2-phenoxy) titanium dichloride, diethylsilylene(3,6-dimethoxyfluoren-9-yl)(3-trimethylsilyl-5-methyl-2-phenoxy)titanium dichloride, diethylsilylene(3,6-dimethoxyfluoren-9-yl)(2-naphthoxy)titanium dichloride, diethylsilylene(3,6-dichlorofluoren-9-yl)(2-phenoxy)titanium dichloride, diethylsilylene(3,6-dichlorofluoren-9-yl)(3,4-dimethyl-2-phenoxy) titanium dichloride, diethylsilylene(3,6-dichlorofluoren-9-yl)(3-tert-butyl-5-methyl-2-phenoxy)titanium dichloride, diethylsilylene(3,6-dichlorofluoren-9-yl)(3-tert-butyl-5-methoxy-2-phenoxy)titanium dichloride, diethylsilylene(3,6-dichlorofluoren-9-yl)(3-tert-butyl-5-dimethylamino-2-phenoxy)titanium dichloride, diethylsilylene(3,6-dichlorofluoren-9-yl)(3-tert-butyl-2-phenoxy) titanium dichloride, diethylsilylene(3,6-dichlorofluoren-9-yl)(3-tert-butyl-5-chloro-2-phenoxy)titanium dichloride, diethylsilylene(3,6-dichlorofluoren-9-yl)(3-phenyl-2-phenoxy)titanium dichloride, diethylsilylene(3,6-dichlorofluoren-9-yl) (3-tert-butyldimethylsilyl-5-methyl-2-phenoxy)titanium dichloride, diethylsilylene(3,6-dichlorofluoren-9-yl)(3-trimethylsilyl-5-methyl-2-phenoxy)titanium dichloride, diethylsilylene(3,6-dichlorofluoren-9-yl)(2-naphthoxy)titanium dichloride, diethylsilylene(6,6,9,9-tetramethyl-6,7,8,9-tetrahydrobenzofluoren-11-yl)(2-phenoxy)titanium dichloride, diethylsilylene(6,6,9,9-tetramethyl-6,7,8,9-tetrahydrobenzofluoren-11-yl)(3,4-dimethyl-2-phenoxy)titanium dichloride, diethylsilylene(6,6,9,9-tetramethyl-6,7,8,9-tetrahydrobenzofluoren-11-yl)(3-tert-butyl-5-methyl-2-phenoxy) titanium dichloride, diethylsilylene(6,6,9,9-tetramethyl-6,7,8,9-tetrahydrobenzofluoren-11-yl)(3-tert-butyl-5-methoxy-2-phenoxy)titanium dichloride, diethylsilylene(6,6,9,9-tetramethyl-6,7,8,9-tetrahydrobenzofluoren-11-yl)(3-tert-butyl-5-dimethylamino-2-phenoxy)titanium dichloride, diethylsilylene(6,6,9,9-tetramethyl-6,7,8,9-tetrahydrobenzofluoren-11-yl)(3-tert-butyl-2-phenoxy)titanium dichloride, diethylsilylene(6,6,9,9-tetramethyl-6,7,8,9-tetrahydrobenzofluoren-11-yl)(3-tert-butyl-5-chloro-2-phenoxy) titanium dichloride, diethylsilylene(6,6,9,9-tetramethyl-6,7,8,9-tetrahydrobenzofluoren-11-yl)(3-phenyl-2-phenoxy) titanium dichloride, diethylsilylene(6,6,9,9-tetramethyl-6,7,8,9-tetrahydrobenzofluoren-11-yl)(3-tert-butyldimethylsilyl-5-methyl-2-phenoxy)titanium dichloride, diethylsilylene(6,6,9,9-tetramethyl-6,7,8,9-tetrahydrobenzofluoren-11-yl)(3-trimethylsilyl-5-methyl-2-phenoxy)titanium dichloride, diethylsilylene(6,6,9,9-tetramethyl-6,7,8,9-tetrahydrobenzofluoren-11-yl)(2-naphthoxy)titanium dichloride, diethylsilylene(2-tert-butyl-6,6,9,9-tetramethyl-6,7,8,9-tetrahydrobenzofluoren-11-yl)(2-phenoxy)titanium dichloride, diethylsilylene(2-tert-butyl-6,6,9,9-tetramethyl-6,7,8,9-tetrahydrobenzofluoren-11-yl)(3,4-dimethyl-2-phenoxy)titanium dichloride, diethylsilylene(2-tert-butyl-6,6,9,9-tetramethyl-6,7,8,9-tetrahydrobenzofluoren-11-yl)(3-tert-butyl-5-methyl-2-phenoxy)titanium dichloride, diethylsilylene(2-tert-butyl-6,6,9,9-tetramethyl-6,7,8,9-tetrahydrobenzofluoren-11-yl)(3-tert-butyl-5-methoxy-2-phenoxy)titanium dichloride, diethylsilylene(2-tert-butyl-6,6,9,9-tetramethyl-6,7,8,9-tetrahydrobenzofluoren-11-yl)(3-tert-butyl-5-dimethylamino-2-phenoxy)titanium dichloride, diethylsilylene(2-tert-butyl-6,6,9,9-tetramethyl-6,7,8,9-tetrahydrobenzofluoren-11-yl)(3-tert-butyl-2-phenoxy)titanium dichloride, diethylsilylene(2-tert-butyl-6,6,9,9-tetramethyl-6,7,8,9-tetrahydrobenzofluoren-11-yl)(3-tert-butyl-5-chloro-2-phenoxy)titanium dichloride, diethylsilylene(2-tert-butyl-6,6,9,9-tetramethyl-6,7,8,9-tetrahydrobenzofluoren-11-yl)(3-phenyl-2-phenoxy) titanium dichloride, diethylsilylene(2-tert-butyl-6,6,9,9-tetramethyl-6,7,8,9-tetrahydrobenzofluoren-11-yl)(3-tert-butyldimethylsilyl-5-methyl-2-phenoxy)titanium dichloride, diethylsilylene(2-tert-butyl-6,6,9,9-tetramethyl-6,7,8,9-tetrahydrobenzofluoren-11-yl)(3-trimethylsilyl-5-methyl-2-phenoxy)titanium dichloride, diethylsilylene(2-tert-butyl-6,6,9,9-tetramethyl-6,7,8,9-tetrahydrobenzofluoren-11-yl)(2-naphthoxy)titanium dichloride, diethylsilylene(3-tert-butyl-6,6,9,9-tetramethyl-6,7,8,9-tetrahydrobenzofluoren-11-yl) (2-phenoxy)titanium dichloride, diethylsilylene(3-tert-butyl-6,6,9,9-tetramethyl-6,7,8,9-tetrahydrobenzofluoren-11-yl) (3,4-dimethyl-2-phenoxy)titanium dichloride, diethylsilylene(3-tert-butyl-6,6,9,9-tetramethyl-6,7,8,9-tetrahydrobenzofluoren-11-yl)(3-tert-butyl-5-methyl-2-phenoxy)titanium dichloride, diethylsilylene(3-tert-butyl-6,6,9,9-tetramethyl-6,7,8,9-tetrahydrobenzofluoren-11-yl)(3-tert-butyl-5-methoxy-2-phenoxy)titanium dichloride, diethylsilylene(3-tert-butyl-6,6,9,9-tetramethyl-6,7,8,9-tetrahydrobenzofluoren-11-yl)(3-tert-butyl-5-dimethylamino-2-phenoxy)titanium dichloride, diethylsilylene(3-tert-butyl-6,6,9,9-tetramethyl-6,7,8,9-tetrahydrobenzofluoren-11-yl) (3-tert-butyl-2-phenoxy)titanium dichloride, diethylsilylene (3-tert-butyl-6,6,9,9-tetramethyl-6,7,8,9-tetrahydrobenzofluoren-11-yl)(3-tert-butyl-5-chloro-2-phenoxy)titanium dichloride, diethylsilylene(3-tert-butyl-6,6,9,9-tetramethyl-6,7,8,9-tetrahydrobenzofluoren-11-yl)(3-phenyl-2-phenoxy)titanium dichloride, diethylsilylene(3-tert-butyl-6,6,9,9-tetramethyl-6,7,8,9-tetrahydrobenzofluoren-11-yl)(3-tert-butyldimethylsilyl-5-methyl-2-phenoxy)titanium dichloride, diethylsilylene(3-tert-butyl-6,6,9,9-tetramethyl-6,7,8,9-tetrahydrobenzofluoren-11-yl)(3-trimethylsilyl-5-methyl-2-phenoxy)titanium dichloride, diethylsilylene(3-tert-butyl-6,6,9,9-tetramethyl-6,7,8,9-tetrahydrobenzofluoren-11-yl)(2-naphthoxy)titanium dichloride, diethylsilylene(2,2,5,5,8,8,11,11-octamethyl-2,3,4,5,8,9,10,11-octahydrodibenzofluoren-13-yl)(2-phenoxy)titanium dichloride, diethylsilylene(2,2,5,5,8,8,11,11-octamethyl-2,3,4,5,8,9,10,11-octahydrodibenzofluoren-13-yl)(3,4-dimethyl-2-phenoxy)titanium dichloride, diethylsilylene(2,2,5,5,8,8,11,11-octamethyl-2,3,4,5,8,9,10,11-octahydrodibenzofluoren-13-yl)(3-tert-butyl-5-methyl-2-phenoxy)titanium dichloride, diethylsilylene(2,2,5,5,8,8,11,11-octamethyl-2,3,4,5,8,9,10,11-octahydrodibenzofluoren-13-yl)(3-tert-butyl-5-methoxy-2-phenoxy)titanium dichloride, diethylsilylene(2,2,5,5,8,8,11,11-octamethyl-2,3,4,5,8,9,10,11-octahydrodibenzofluoren-13-yl)(3-tert-butyl-5-dimethylamino-2-phenoxy)titanium dichloride, diethylsilylene(2,2,5,5,8,8,11,11-octamethyl-2,3,4,5,8,9,10,11-octahydrodibenzofluoren-13-yl)(3-tert-butyl-2-phenoxy) titanium dichloride, diethylsilylene(2,2,5,5,8,8,11,11-octamethyl-2,3,4,5,8,9,10,11-octahydrodibenzofluoren-13-yl)(3-tert-butyl-5-chloro-2-phenoxy)titanium dichloride, diethylsilylene(2,2,5,5,8,8,11,11-octamethyl-2,3,4,5,8,9,10,11-octahydrodibenzofluoren-13-yl)(3-phenyl-2-phenoxy)titanium dichloride, diethylsilylene(2,2,5,5,8,8,11,11-octamethyl-2,3,4,5,8,9,10,11-octahydrodibenzofluoren-13-yl)(3-tert-butyldimethylsilyl-5-methyl-2-phenoxy)titanium dichloride, diethylsilylene(2,2,5,5,8,8,11,11-octamethyl-2,3,4,5,8,9,10,11-octahydrodibenzofluoren-13-yl)(3-trimethylsilyl-5-methyl-2-phenoxy)titanium dichloride, and diethylsilylene(2,2,5,5,8,8,11,11-octamethyl-2,3,4,5,8,9,10,11-octahydrodibenzofluoren-13-yl)(2-naphthoxy)titanium dichloride; and compounds obtained by replacing the term of "diethylsilylene" contained in the above-exemplified compounds with respective terms of "dimethylsilylene", "diphenylsilylene", "ethylmethylsilylene", "methylphenylsilylene", "dimethylgermilene", and "isopropylidene".

Also, there can be exemplified compounds obtained by replacing the term of "chloride" contained in the above-exemplified compounds with respective terms of "fluoride", "bromide", "iodide", "methyl", "benzyl", "methoxide", "ethoxide", "n-butoxide", "isopropoxide", "phenoxide", "dimethylamido", and "diethylamido".

Further, there can be exemplified compounds obtained by replacing the term of "titanium" contained in the above-exemplified compounds with respective terms of "zirconium" and "hafnium".

[Process for Producing Transition Metal Complex]

An example of a process for producing the transition metal complex represented by the above-mentioned general formula [1] is a process comprising the steps of:

(1) reacting the substituent-carrying fluorene compound represented by the following general formula [2] with a base; and (2) reacting with the transition metal compound represented by the following general formula [3]:

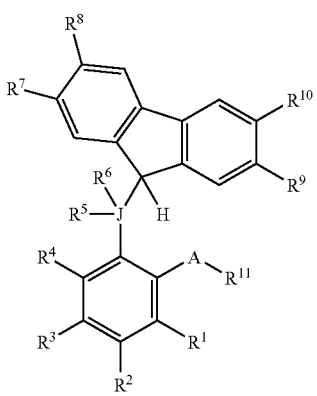

[2]

wherein A is the group 16 atom in the periodic table of elements; J is the group 14 atom therein; $R^1$, $R^2$, $R^3$, $R^4$, $R^5$ and $R^6$ are independently of one another (1) a substituent selected from the group consisting of (1-1) an alkyl group having 1 to 20 carbon atoms, (1-2) an aralkyl group having 7 to 20 carbon atoms, (1-3) an aryl group having 6 to 20 carbon atoms, (1-4) a substituent-carrying silyl group having 1 to 20 carbon atoms, which substituent is a hydrocarbyl group, (1-5) a disubstituent-carrying amino group having 2 to 20 carbon atoms, which substituent is a hydrocarbyl group, (1-6) an alkoxy group having 1 to 20 carbon atoms, (1-7) an aralkyloxy group having 7 to 20 carbon atoms, and (1-8) an aryloxy group having 6 to 20 carbon atoms, (2) a halogen atom or (3) a hydrogen atom; $R^1$ and $R^2$, $R^2$ and $R^3$, and $R^3$ and $R^4$ may be linked to each other, respectively, to form respective rings; $R^5$ and $R^6$ may be linked to each other to form a ring; $R^7$, $R^8$, $R^9$ and $R^{10}$ are independently of one another (1) a substituent selected from the group consisting of (1-1) an alkyl group having 1 to 20 carbon atoms, (1-2) an aralkyl group having 7 to 20 carbon atoms, (1-3) an aryl group having 6 to 20 carbon atoms, (1-4) a substituent-carrying silyl group having 1 to 20 carbon atoms, which substituent is a hydrocarbyl group, (1-5) a disubstituent-carrying amino group having 2 to 20 carbon atoms, which substituent is a hydrocarbyl group, (1-6) an alkoxy group having 1 to 20 carbon atoms, (1-7) an aralkyloxy group having 7 to 20 carbon atoms, and (1-8) an aryloxy group having 6 to 20 carbon atoms, (2) a halogen atom or (3) a hydrogen atom; at least two of $R^7$, $R^8$, $R^9$ and $R^1$ are the substituent selected from the above-mentioned group or a halogen atom; $R^7$ and $R^8$ may be linked to each other to form a ring; $R^9$ and $R^{10}$ may be linked to each other to form a ring; and $R^{11}$ is a hydrocarbyl group or a three substituent-carrying silyl group, and $$M\text{-}X^3_n$$ [3], wherein M is the group 4 transition metal atom in the periodic table of elements; n is an integer of 3 or 4; $X^3$ is (1) a substituent selected from the group consisting of (1-1) an alkyl group having 1 to 20 carbon atoms, (1-2) an aralkyl group having 7 to 20 carbon atoms, (1-3) an aryl group having 6 to 20 carbon atoms, (1-4) a substituent-carrying amino group having 1 to 20 carbon atoms, which substituent is a hydrocarbyl group, (1-5) an alkoxy group having 1 to 20 carbon atoms, (1-6) an aralkyloxy group having 7 to 20 carbon atoms, and (1-7) an aryloxy group having 6 to 20 carbon atoms, (2) a halogen atom or (3) a hydrogen atom; and plural $X^3$s are the same as, or different from one another.

A, J, $R^1$, $R^2$, $R^3$, $R^4$, $R^5$, $R^6$, $R^7$, $R^8$, $R^9$ and $R^{10}$ in the general formula [2] are the same as those in the general formula [1], respectively.

$R^{11}$ in the general formula [2] is a hydrocarbyl group or a trisubstituent-carrying silyl group.

Examples of the hydrocarbyl group in $R^{11}$ are an alkyl group having 1 to 10 carbon atoms such as a methyl group, an ethyl group, a propyl group, a butyl group, a pentyl group, a hexyl group, a heptyl group, an octyl group, a nonyl group, and a decyl group; an alkenyl group having 2 to 10 carbon atoms such as a vinyl group, an allyl group, a propenyl group, a 2-methyl-2-propenyl group, a homoally group, a pentenyl group, a hexenyl group, a heptenyl group, an octenyl group a nonenyl group, and a decenyl group; an aralkyl group having 7 to 12 carbon atoms such as a benzyl group, a (4-methylphenyl)methyl group, and a (2,4,6-trimethylphenyl)methyl group; and an alkoxyalkyl group such as a methoxymethyl group and a methoxyethoxymethyl group. Each of those hydrocarbyl groups may be substituted by a halogen atom such as a fluorine atom, a chlorine atom, a bromine atom and an iodine atom, and an example thereof is a 2-chloro-2-propenyl group.

Examples of the trisubstituent-carrying silyl group in $R^{11}$ are a trimethylsilyl group, a triethylsilyl group, a tri-n-propylsilyl group, a triisopropylsilyl group, a tri-n-butylsilyl group, a tri-sec-butylsilyl group, a tri-tert-butylsilyl group, a triisobutylsilyl group, a tert-butyl-dimethylsilyl group, a tri-n-pentylsilyl group, a tri-n-hexylsilyl group, a tricyclohexylsilyl group, and a triphenylsilyl group.

$R^{11}$ is preferably an alkenyl group, and more preferably an allyl group in order to produce the transition metal complex represented by the general formula [1] in a good yield.

Examples of the substituent-carrying fluorene compound represented by the general formula [2] are the following compounds: (2-allyloxyphenyl)(2,7-di-tert-butylfluoren-9-yl)diethylsilane, (2-allyloxy-3-methylphenyl)(2,7-di-tert-butylfluoren-9-yl)diethylsilane, (2-allyloxy-3,5-dimethylphenyl)(2,7-di-tert-butylfluoren-9-yl)diethylsilane, (2-allyloxy-3-tert-butylphenyl)(2,7-di-tert-butylfluoren-9-yl)diethylsilane, (2-allyloxy-3-tert-butyl-5-methylphenyl)(2,7-di-tert-butylfluoren-9-yl)diethylsilane, (2-allyloxy-3,5-di-tert-butylphenyl)(2,7-di-tert-butylfluoren-9-yl)diethylsilane, (2-allyloxy-5-methyl-3-phenylphenyl)(2,7-di-tert-butylfluoren-9-yl)diethylsilane, (2-allyloxy-5-methyl-3-trimethylsilylphenyl)(2,7-di-tert-butylfluoren-9-yl)diethylsilane, (2-allyloxy-3-tert-butyldimethylsilyl-5-methylphenyl)(2,7-di-tert-butylfluoren-9-yl)diethylsilane, (2-allyloxy-3,5-diamylphenyl)(2,7-di-tert-butylfluoren-9-yl)diethylsilane, (2-allyloxy-3-tert-butyl-5-methoxyphenyl)(2,7-di-tert-butylfluoren-9-yl)diethylsilane, (2-allyloxy-5-tert-butyl-3-chlorophenyl)(2,7-di-tert-butylfluoren-9-yl)diethylsilane, (1-allyloxynaphthalen-2-yl)(2,7-di-tert-butylfluoren-9-yl)diethylsilane, (2-allyloxy-3-tert-butyl-5-methoxyphenyl)(2,7-di-tert-butylfluoren-9-yl)diethylsilane, (2-allyloxyphenyl)(2,7-diphenylfluoren-9-yl)diethylsilane, (2-allyloxy-3-methylphenyl)(2,7-diphenylfluoren-9-yl)diethylsilane, (2-allyloxy-3,5-dimethylphenyl)(2,7-diphenylfluoren-9-yl)diethylsilane, (2-allyloxy-3-tert-butylphenyl)(2,7-diphenylfluoren-9-yl)diethylsilane, (2-allyloxy-3-tert-butyl-5-methylphenyl)(2,7-diphenylfluoren-9-yl)diethylsilane, (2-allyloxy-3,5-di-tert-butylphenyl)(2,7-diphenylfluoren-9-yl)diethylsilane, (2-allyloxy-5-methyl-3-phenylphenyl)(2,7-diphenylfluoren-9-yl)diethylsilane, (2-allyloxy-5-methyl-3-trimethylsilylphenyl)(2,7-diphenylfluoren-9-yl)diethylsilane, (2-allyloxy-3-tert-butyldimethylsilyl-5-methylphenyl)(2,7-diphenylfluoren-9-yl)diethylsilane, (2-allyloxy-3,5-diamylphenyl)(2,7-diphenylfluoren-9-yl)diethylsilane, (2-allyloxy-3-tert-butyl-5-methoxyphenyl)(2,7-diphenylfluoren-9-yl)diethylsilane, (2-allyloxy-5-tert-butyl-3-chlorophenyl)(2,7-diphenylfluoren-9-yl)diethylsilane, (1-allyloxynaphthalen-2-yl)(2,7-diphenylfluoren-9-yl)diethylsilane, (2-allyloxy-3-tert-butyl-5-methoxyphenyl)(2,7-diphenylfluoren-9-yl)diethylsilane, (2-allyloxyphenyl)(2,7-dichlorofluoren-9-yl)diethylsilane, (2-allyloxy-3-methylphenyl)(2,7-dichlorofluoren-9-yl)diethylsilane, (2-allyloxy-3,5-dimethylphenyl)(2,7-dichlorofluoren-9-yl)diethylsilane, (2-allyloxy-3-tert-butylphenyl)(2,7-dichlorofluoren-9-yl)diethylsilane, (2-allyloxy-3-tert-butyl-5-methylphenyl)(2,7-dichlorofluoren-9-yl)diethylsilane, (2-allyloxy-3,5-di-tert-butylphenyl)(2,7-dichlorofluoren-9-yl)diethylsilane, (2-allyloxy-5-methyl-3-phenylphenyl)(2,7-dichlorofluoren-9-yl)diethylsilane, (2-allyloxy-5-methyl-3-trimethylsilylphenyl)(2,7-dichlorofluoren-9-yl)diethylsilane, (2-allyloxy-3-tert-butyldimethylsilyl-5-methylphenyl)(2,7-dichlorofluoren-9-yl)diethylsilane, (2-allyloxy-3,5-diamylphenyl)(2,7-dichlorofluoren-9-yl)diethylsilane, (2-allyloxy-3-tert-butyl-5-methoxyphenyl)(2,7-dichlorofluoren-9-yl)diethylsilane, (2-allyloxy-5-tert-butyl-3-chlorophenyl)(2,7-dichlorofluoren-9-yl)diethylsilane, (1-allyloxynaphthalen-2-yl)(2,7-dichlorofluoren-9-yl)diethylsilane, (2-allyloxy-3-tert-butyl-5-methoxyphenyl)(2,7-dichlorofluoren-9-yl)diethylsilane, (2-allyloxyphenyl)(3,6-di-tert-butylfluoren-9-yl)diethylsilane, (2-allyloxy-3-methylphenyl)(3,6-di-tert-butylfluoren-9-yl)diethylsilane, (2-allyloxy-3,5-dimethylphenyl)(3,6-di-tert-butylfluoren-9-yl)diethylsilane, (2-allyloxy-3-tert-butylphenyl)(3,6-di-tert-butylfluoren-9-yl)diethylsilane, (2-allyloxy-3-tert-butyl-5-methylphenyl)(3,6-di-tert-butylfluoren-9-yl)diethylsilane, (2-allyloxy-3,5-di-tert-butylphenyl)(3,6-di-tert-butylfluoren-9-yl)diethylsilane, (2-allyloxy-5-methyl-3-phenylphenyl)(3,6-di-tert-butylfluoren-9-yl)diethylsilane, (2-allyloxy-5-methyl-3-trimethylsilylphenyl)(3,6-di-tert-butylfluoren-9-yl)diethylsilane, (2-allyloxy-3-tert-butyldimethylsilyl-5-methylphenyl)(3,6-di-tert-butylfluoren-9-yl)diethylsilane, (2-allyloxy-3,5-diamylphenyl)(3,6-di-tert-butylfluoren-9-yl)diethylsilane, (2-allyloxy-3-tert-butyl-5-methoxyphenyl)(3,6-di-tert-butylfluoren-9-yl)diethylsilane, (2-allyloxy-5-tert-butyl-3-chlorophenyl)(3,6-di-tert-butylfluoren-9-yl)diethylsilane, (1-allyloxynaphthalen-2-yl)(3,6-di-tert-butylfluoren-9-yl)diethylsilane, (2-allyloxy-3-tert-butyl-5-methoxyphenyl)(3,6-di-tert-butylfluoren-9-yl)diethylsilane, (2-allyloxyphenyl)(6,6,9,9-tetramethyl-6,7,8,9-tetrahydrobenzofluoren-11-yl)diethylsilane, (2-allyloxy-3-methylphenyl)(6,6,9,9-tetramethyl-6,7,8,9-tetrahydrobenzofluoren-11-yl)diethylsilane, (2-allyloxy-3,5-dimethylphenyl)(6,6,9,9-tetramethyl-6,7,8,9-tetrahydrobenzofluoren-11-yl)diethylsilane, (2-allyloxy-3-tert-butylphenyl)(6,6,9,9-tetramethyl-6,7,8,9-tetrahydrobenzofluoren-11-yl)diethylsilane, (2-allyloxy-3-tert-butyl-5-methylphenyl)(6,6,9,9-tetramethyl-6,7,8,9-tetrahydrobenzofluoren-11-yl)diethylsilane, (2-allyloxy-3,5-di-tert-butylphenyl)(6,6,9,9-tetramethyl-6,7,8,9-tetrahydrobenzofluoren-11-yl)diethylsilane, (2-allyloxy-5-methyl-3-phenylphenyl)(6,6,9,9-tetramethyl-6,7,8,9-tetrahydrobenzofluoren-11-yl)diethylsilane, (2-allyloxy-5-methyl-3-trimethylsilylphenyl)(6,6,9,9-tetramethyl-6,7,8,9-tetrahydrobenzofluoren-11-yl)diethylsilane, (2-allyloxy-3-tert-butyldimethylsilyl-5-methylphenyl)(6,6,9,9-tetramethyl-6,7,8,9-tetrahydrobenzofluoren-11-yl)diethylsilane, (2-allyloxy-3,5-diamylphenyl)(6,6,9,9-tetramethyl-6,7,8,9-tetrahydrobenzofluoren-11-yl)diethylsilane, (2-allyloxy-3-tert-butyl-5-methoxyphenyl)(6,6,9,9-tetramethyl-6,7,8,9-tetrahydrobenzofluoren-11-yl)diethylsilane, (2-allyloxy-5-tert-butyl-3-chlorophenyl)(6,6,9,9-tetramethyl-6,7,8,9-tetrahydrobenzofluoren-11-yl)diethylsilane, (1-allyloxynaphthalen-2-yl)(6,6,9,9-tetramethyl-6,7,8,9-tetrahydrobenzofluoren-11-yl)diethylsilane, (2-allyloxy-3-tert-butyl-5-methoxyphenyl)(6,6,9,9-tetramethyl-6,7,8,9-tetrahydrobenzofluoren-11-yl)diethylsilane, (2-allyloxyphenyl)(2-tert-butyl-6,6,9,9-tetramethyl-6,7,8,9-tetrahydrobenzofluoren-11-yl)diethylsilane, (2-allyloxy-3-methylphenyl)(2-tert-butyl-6,6,9,9-tetramethyl-6,7,8,9-tetrahydrobenzofluoren-11-yl)diethylsilane, (2-allyloxy-3,5-dimethylphenyl)(2-tert-butyl-6,6,9,9-tetramethyl-6,7,8,9-tetrahydrobenzofluoren-11-yl)diethylsilane, (2-allyloxy-3-tert-butylphenyl)(2-tert-butyl-6,6,9,9-tetramethyl-6,7,8,9-tetrahydrobenzofluoren-11-yl)diethylsilane, (2-allyloxy-3-tert-butyl-5-methylphenyl)(2-tert-butyl-6,6,9,9-tetramethyl-6,7,8,9-tetrahydrobenzofluoren-11-yl)diethylsilane, (2-allyloxy-3,5-di-tert-butylphenyl)(2-tert-butyl-6,6,9,9-tetramethyl-6,7,8,9-tetrahydrobenzofluoren-11-yl)diethylsilane, (2-allyloxy-5-methyl-3-phenylphenyl)(2-tert-butyl-6,6,9,9-tetramethyl-6,7,8,9-tetrahydrobenzofluoren-11-yl)diethylsilane, (2-allyloxy-5-methyl-3-trimethylsilylphenyl)(2-tert-butyl-6,6,9,9-tetramethyl-6,7,8,9-tetrahydrobenzofluoren-11-yl)diethylsilane, (2-allyloxy-3-tert-butyldimethylsilyl-5-methylphenyl)(2-tert-butyl-6,6,9,9-tetramethyl-6,7,8,9-tetrahydrobenzofluoren-11-yl)diethylsilane, (2-allyloxy-3,5-diamylphenyl)(2-tert-butyl-6,6,9,9-tetramethyl-6,7,8,9-tetrahydrobenzofluoren-11-yl)diethylsilane, (2-allyloxy-3-tert-butyl-5-methoxyphenyl)(2-tert-butyl-6,6,9,9-tetramethyl-6,7,8,9-tetrahydrobenzofluoren-11-yl)diethylsilane, (2-allyloxy-5-tert-butyl-3-chlorophenyl)(2-tert-butyl-6,6,9,9-tetramethyl-6,7,8,9-tetrahydrobenzofluoren-11-yl)diethylsilane, (1-allyloxynaphthalen-2-yl)(2-tert-butyl-6,6,9,9-tetramethyl-6,7,8,9-tetrahydrobenzofluoren-11-yl)diethylsilane, (2-allyloxy-3-tert-butyl-5-methoxyphenyl)(2-tert-butyl-6,6,9,9-tetramethyl-6,7,8,9-tetrahydrobenzofluoren-11-yl)diethylsilane, (2-allyloxyphenyl)(3-tert-butyl-6,6,9,9-tetramethyl-6,7,8,9-tetrahydrobenzofluoren-11-yl)diethylsilane, (2-allyloxy-3-methylphenyl)(3-tert-butyl-6,6,9,9-tetramethyl-6,7,8,9-tetrahydrobenzofluoren-11-yl)diethylsilane, (2-allyloxy-3,5-dimethylphenyl)(3-tert-butyl-6,6,9,9-tetramethyl-6,7,8,9-tetrahydrobenzofluoren-11-yl)diethylsilane, (2-allyloxy-3-tert-butylphenyl)(3-tert-butyl-6,6,9,9-tetramethyl-6,7,8,9-tetrahydrobenzofluoren-11-yl) diethylsilane, (2-allyloxy-3-tert-butyl-5-methylphenyl)(3-tert-butyl-6,6,9,9-tetramethyl-6,7,8,9-tetrahydrobenzofluoren-11-yl)diethylsilane, (2-allyloxy-3,5-di-tert-butylphenyl)(3-tert-butyl-6,6,9,9-tetramethyl-6,7,8,9-tetrahydrobenzofluoren-11-yl)diethylsilane, (2-allyloxy-5-methyl-3-phenylphenyl)(3-tert-butyl-6,6,9,9-tetramethyl-6,7,8,9-tetrahydrobenzofluoren-11-yl)diethylsilane, (2-allyloxy-5-methyl-3-trimethylsilylphenyl)(3-tert-butyl-6,6,9,9-tetramethyl-6,7,8,9-tetrahydrobenzofluoren-11-yl)diethylsilane, (2-allyloxy-3-tert-butyldimethylsilyl-5-methylphenyl)(3-tert-butyl-6,6,9,9-tetramethyl-6,7,8,9-tetrahydrobenzofluoren-11-yl)diethylsilane, (2-allyloxy-3,5-diamylphenyl)(3-tert-butyl-6,6,9,9-tetramethyl-6,7,8,9-tetrahydrobenzofluoren-11-yl)diethylsilane, (2-allyloxy-3-tert-butyl-5-methoxyphenyl)(3-tert-butyl-6,6,9,9-tetramethyl-6,7,8,9-tetrahydrobenzofluoren-11-yl) diethylsilane, (2-allyloxy-5-tert-butyl-3-chlorophenyl)(3-tert-butyl-6,6,9,9-tetramethyl-6,7,8,9-tetrahydrobenzofluoren-11-yl)diethylsilane, (1-allyloxynaphthalen-2-yl)(3-tert-butyl-6,6,9,9-tetramethyl-6,7,8,9-tetrahydrobenzofluoren-11-yl)diethylsilane, (2-allyloxy-3-tert-butyl-5-methoxyphenyl)(3-tert-butyl-6,6,9,9-tetramethyl-6,7,8,9-tetrahydrobenzofluoren-11-yl)diethylsilane, (2-allyloxyphenyl)(2,2,5,5,8,8,11,11-octamethyl-2,3,4,5,8,9,10,11-octahydrodibenzofluoren-13-yl) diethylsilane, (2-allyloxy-3-methylphenyl)(2,2,5,5,8,8,11,11-octamethyl-2,3,4,5,8,9,10,11-octahydrodibenzofluoren-13-yl)diethylsilane, (2-allyloxy-3,5-dimethylphenyl)(2,7-di-tert-butylfluoren-9-yl)diethylsilane, (2-allyloxy-3-tert-butylphenyl)(2,2,5,5,8,8,11,11-octamethyl-2,3,4,5,8,9,10,11-octahydrodibenzofluoren-13-yl)diethylsilane, (2-allyloxy-3-tert-butyl-5-methylphenyl)(2,2,5,5,8,8,11,11-octamethyl-2,3,4,5,8,9,10,11-octahydrodibenzofluoren-13-yl)diethylsilane, (2-allyloxy-3,5-di-tert-butylphenyl)(2,2,5,5,8,8,11,11-octamethyl-2,3,4,5,8,9,10,11-octahydrodibenzofluoren-13-yl)diethylsilane, (2-allyloxy-5-methyl-3-phenylphenyl)(2,2,5,5,8,8,11,11-octamethyl-2,3,4,5,8,9,10,11-octahydrodibenzofluoren-13-yl)diethylsilane, (2-allyloxy-5-methyl-3-trimethylsilylphenyl)(2,2,5,5,8,8,11,11-octamethyl-2,3,4,5,8,9,10,11-octahydrodibenzofluoren-13-yl)diethylsilane, (2-allyloxy-3-tert-butyldimethylsilyl-5-methylphenyl)(2,2,5,5,8,8,11,11-octamethyl-2,3,4,5,8,9,10,11-octahydrodibenzofluoren-13-yl)diethylsilane, (2-allyloxy-3,5-diamylphenyl)(2,2,5,5,8,8,11,11-octamethyl-2,3,4,5,8,9,10,11-octahydrodibenzofluoren-13-yl)diethylsilane, (2-allyloxy-3-tert-butyl-5-methoxyphenyl)(2,2,5,5,8,8,11,11-octamethyl-2,3,4,5,8,9,10,11-octahydrodibenzofluoren-13-yl)diethylsilane, (2-allyloxy-5-tert-butyl-3-chlorophenyl)(2,2,5,5,8,8,11,11-octamethyl-2,3,4,5,8,9,10,11-octahydrodibenzofluoren-13-yl) diethylsilane, (1-allyloxynaphthalen-2-yl)(2,2,5,5,8,8,11,11-octamethyl-2,3,4,5,8,9,10,11-octahydrodibenzofluoren-13-yl)diethylsilane, and (2-allyloxy-3-tert-butyl-5-methoxyphenyl)(2,2,5,5,8,8,11,11-octamethyl-2,3,4,5,8,9,10,11-octahydrodibenzofluoren-13-yl)diethylsilane; and compounds obtained by replacing the term of "diethylsilane" contained in the above-exemplified compounds with respective terms of "dimethylsilane", "diphenylsilane", "ethylmethylsilane", "methylphenylsilane", and "dimethylgermanium".

M in the general formula [3] is the same as that in the general formula [1].

$X^3$ in the general formula [3] is a substituent selected from the group consisting of (1-1) an alkyl group having 1 to 20 carbon atoms, (1-2) an aralkyl group having 7 to 20 carbon atoms, (1-3) an aryl group having 6 to 20 carbon atoms, (1-4) a substituent-carrying amino group having 1 to 20 carbon atoms, which substituent is a hydrocarbyl group, (1-5) an alkoxy group having 1 to 20 carbon atoms, (1-6) an aralkyloxy group having 7 to 20 carbon atoms, and (1-7) an aryloxy group having 6 to 20 carbon atoms, (2) a halogen atom or (3) a hydrogen atom; n is an integer of 3 or 4; and plural $X^3$s are the same as, or different from one another.

Examples of the alkyl group having 1 to 20 carbon atoms in $X^3$ are a methyl group, an ethyl group, a n-propyl group, an isopropyl group, a n-butyl group, a sec-butyl group, a tert-butyl group, a n-pentyl group, a neopentyl group, an isopentyl group, a n-hexyl group, a n-heptyl group, a n-octyl group, a n-decyl group, a n-nonyl group, a n-decyl group, a n-dodecyl group, a n-tridecyl group, a n-tetradecyl group, a n-pentadecyl group, a n-hexadecyl group, a n-heptadecyl group, a n-octadecyl group, a n-nonadecyl group, and a n-eicosyl group. Among them, preferred is a methyl group, an ethyl group, an isopropyl group, a tert-butyl group, a n-pentyl group, a neopentyl group or an isopentyl group.

Each of those alkyl groups may be substituted by a halogen atom such as a fluorine atom, a chlorine atom, a bromine atom and an iodine atom. Examples of an alkyl group substituted by a halogen atom and having 1 to 20 carbon atoms are a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, and a perbromoeicosyl group.

Examples of the aralkyl group having 7 to 20 carbon atoms in $X^3$ are a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (4,6-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)

methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-tetradecylphenyl)methyl group, a naphthylmethyl group and an anthracenylmethyl group. Among them, preferred is a benzyl group. Each of those aralkyl groups may be substituted by a halogen atom such as a fluorine atom, a chlorine atom, a bromine atom and an iodine atom.

Examples of the aryl group having 6 to 20 carbon atoms in $X^3$ are a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group. Among them, preferred is a phenyl group. Each of those aryl groups may be substituted by a halogen atom such as a fluorine atom, a chlorine atom, a bromine atom and an iodine atom.

Examples of the substituent-carrying amino group having 1 to 20 carbon atoms, which substituent is a hydrocarbyl group, in $X^3$ are a methylamino group, an ethylamino group, a n-propylamino group, an isopropylamino group, a n-butylamino group, a sec-butylamino group, a tert-butylamino group, an isobutylamino group, a n-hexylamino group, a n-octylamino group, a n-decylamino group, a dimethylamino group, a diethylamino group, a di-n-propylamino group, a diisopropylamino group, a di-n-butylamino group, a di-sec-butylamino group, a di-tert-butylamino group, a diisobutylamino group, a diphenylamino group, an ethylmethylamino group, an ethylisopropylamino group, a methylphenylamino group, and an ethylphenylamino group. Among them, preferred is a dimethylamino group or a diethylamino group.

Examples of the alkoxy group having 1 to 20 carbon atoms in $X^3$ are a methoxy group, an ethoxy group, a n-propoxy group, an isopropoxy group, a n-butoxy group, a sec-butoxy group, a tert-butoxy group, a n-pentyloxy group, a neopentyloxy group, a n-hexyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group, and a n-eicosoxy group. Among them, preferred is a methoxy group, an ethoxy group, an isopropoxy group, or a tert-butoxy group. Each of those alkoxy groups may be substituted by a halogen atom such as a fluorine atom, a chlorine atom, a bromine atom and an iodine atom.

Examples of the aralkyloxy group having 7 to 20 carbon atoms in $X^3$ are a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a (n-tetradecylphenyl)methoxy group, a naphthylmethoxy group, and an anthracenylmethoxy group. Among them, preferred is a benzyloxy group. Each of those aralkyloxy groups may be substituted by a halogen atom such as a fluorine atom, a chlorine atom, a bromine atom and an iodine atom.

Examples of the aryloxy group having 6 to 20 carbon atoms in $X^3$ are a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxy group, a n-octylphenoxy group, a n-decylphenoxy group, a n-tetradecylphenoxy group, a naphthoxy group and an anthracenoxy group. Among them, preferred is a phenoxy group. Each of those aryloxy groups may be substituted by a halogen atom such as a fluorine atom, a chlorine atom, a bromine atom and an iodine atom.

Examples of the halogen atom in $X^3$ are a fluorine atom, a chlorine atom, a bromine atom and an iodine atom. Among them, preferred is a fluorine atom, a chlorine atom, or a bromine atom, and more preferred is a chlorine atom.

$X^3$ in the general formula [3] is preferably a halogen atom; an alkyl group having 1 to 20 carbon atoms; an aralkyl group having 7 to 20 carbon atoms; a substituent-carrying amino group having 1 to 20 carbon atoms, which substituent is a hydrocarbyl group; an alkoxy group having 1 to 20 carbon atoms; or an aryloxy group having 6 to 20 carbon atoms; and more preferably a methyl group, a tert-butyl group, a benzyl group, a dimethylamino group, a diethylamino group, a methoxy group, an ethoxy group, an isopropoxy group, a tert-butoxy group, a phenoxy group, a fluorine atom, a chlorine atom or a bromine atom.

Examples of the transition metal compound represented by the general formula [3] are a titanium halide such as titanium tetrachloride, titanium trichloride, titanium tetrabromide, and titanium tetraiodide; an amidotitanium such as tetrakis(dimethylamino)titanium, dichlorobis(dimethylamino)titanium, trichloro(dimethylamino)titanium, and tetrakis(diethylamino)titanium; and an alkoxytitanium such as tetraisopropoxytitanium, tetra-n-butoxytitanium, dichlorodiisopropoxytitanium, and trichloroisopropoxytitanium; and compounds obtained by replacing the term of "titanium" contained in the above-exemplified compounds with respective terms of "zirconium" and "hafnium". Among them, preferred is titanium tetrachloride.

An example of the base, which is reacted with the substituent-carrying fluorene compound represented by the general formula [2], is an organic alkali metal compound such as an organic lithium compound, for example, methyllithium, ethyllithium, n-butyllithium, sec-butyllithium, tert-butyllithium, lithiumtrimethylsilyl acetylide, lithium acetylide, trimethylsilylmethyllithium, vinyllithium, phenyllithium, and allyllithium.

The base is used in an amount of generally 0.5 to 5 mol per one mol of the substituent-carrying fluorene compound represented by the general formula [2].

The base may be combined with an amine compound in the reaction of the base with the substituent-carrying fluorene compound represented by the general formula [2]. Examples of the amine compound are a primary amine such as methylamine, ethylamine, n-propylamine, isopropylamine, n-butylamine, tert-butylamine, n-octylamine, n-decylamine, aniline, and ethylene diamine; a secondary amine such as dimethylamine, diethylamine, di-n-propylamine, di-n-butylamine, di-tert-butylamine, di-n-octylamine, di-n-decylamine, pyrrolidine, hexamethyldisilazane, and diphenylamine; and a tertiary amine such as trimethylamine, triethylamine, tri-n-propylamine, tri-n-butylamine, diisopropylethylamine, tri-n-octylamine, tri-n-decylamine, triphenylamine, N,N-dimethylaniline, N,N,N',N'-tetramethylethylene diamine, N-methylpyrrolidine, and 4-dimethylaminopyridine. The amine compound is used in an amount of generally 10 mol or smaller, preferably 0.5 to 10 mol, and further preferably 1 to 3 mol per one mol of the base.

A process, which comprises the steps of (1) reacting the substituent-carrying fluorene compound represented by the general formula [2] with the base, and (2) reacting with the transition metal compound represented by the general formula [3], may be generally carried out according to a method comprising the steps of (i) adding the substituent-carrying fluorene compound represented by the general formula [2] and the base to a solvent, and (ii) adding thereto the transition metal compound represented by the general formula [3]. A solid may be precipitated after the step (i). In that case, there may be carried out a method comprising the steps of (i) adding the solid removed from the reaction system to a similar solvent to the above-mentioned solvent, and (ii) adding thereto the transition metal compound represented by the general formula [3]. Another method comprises the step of adding simultaneously the substituent-carrying fluorene compound represented by the general formula [2], the base, and the transition metal compound represented by the general formula [3] to a solvent.

The transition metal compound represented by the general formula [3] is used in an amount of generally 0.5 to 3 mol, and preferably 0.7 to 1.5 mol per one mol of the substituent-carrying fluorene compound represented by the general formula [2].

The reaction temperature is generally −100° C. to a boiling point of a solvent, and preferably −80 to 100° C. It is preferable from a viewpoint of a yield of the transition metal complex to shield the reaction system from light.

The reaction is carried out generally in a solvent inactive to the reaction. An example s of the solvent is a non-proton solvent such as an aromatic hydrocarbon solvent (for example, benzene and toluene); an aliphatic hydrocarbon solvent (for example, hexane and heptane); an ether solvent (for example, diethyl ether, tetrahydrofuran and 1,4-dioxane); an amide solvent (for example, hexamethylphosphoric amide and dimethylformamide); a polar solvent (for example, acetonitrile, propionitrile, acetone, diethyl ketone, methyl isobutyl ketone, and cyclohexanone); and a halogenated solvent (for example, dichloromethane, dichloroethane, chlorobenzene, and dichlorobenzene). Those solvents are used respectively or in combination of two or more thereof. The solvent is used in an amount of generally 1 to 200 parts by weight, and preferably 3 to 50 parts by weight per one part by weight of the substituent-carrying fluorene compound represented by the general formula [2].

An example of a method for obtaining the objective transition metal complex from the obtained reaction mixture is a conventional method comprising the steps of (1) filtering off a precipitated product, thereby obtaining a filtrate, (2) concentrating the filtrate, thereby obtaining a precipitated transition metal complex, and (3) filtering off the transition metal complex.

An example of a process for producing the substituent-carrying fluorene compound represented by the above general formula [2] is a process comprising the steps of (1) reacting the substituent-carrying fluorene compound represented by the following general formula [4] with a base, and (2) reacting with the compound represented by the general formula [5]:

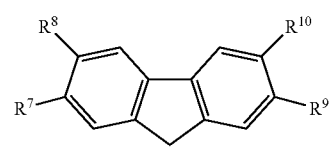

[4]

wherein $R^7$, $R^8$, $R^9$ and $R^{10}$ are independently of one another (1) a substituent selected from the group consisting of (1-1) an alkyl group having 1 to 20 carbon atoms, (1-2) an aralkyl group having 7 to 20 carbon atoms, (1-3) an aryl group having 6 to 20 carbon atoms, (1-4) a substituent-carrying silyl group having 1 to 20 carbon atoms, which substituent is a hydrocarbyl group, (1-5) a disubstituent-carrying amino group having 2 to 20 carbon atoms, which substituent is a hydrocarbyl group, (1-6) an alkoxy group having 1 to 20 carbon atoms, (1-7) an aralkyloxy group having 7 to 20 carbon atoms, and (1-8) an aryloxy group having 6 to 20 carbon atoms, (2) a halogen atom or (3) a hydrogen atom; at least two of $R^7$, $R^8$, $R^9$ and $R^{10}$ are the substituent selected from the above-mentioned group or a halogen atom; $R^7$ and $R^8$ may be linked to each other to form a ring; and $R^9$ and $R^{10}$ may be linked to each other to form a ring, and

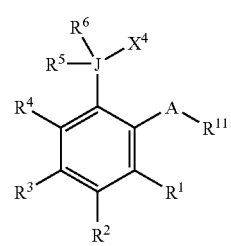

[5]

wherein A is the group 16 atom in the periodic table of elements; J is the group 14 atom therein; $R^1$, $R^2$, $R^3$, $R^4$, $R^5$ and $R^6$ are independently of one another (1) a substituent selected from the group consisting of (1-1) an alkyl group having 1 to 20 carbon atoms, (1-2) an aralkyl group having 7 to 20 carbon atoms, (1-3) an aryl group having 6 to 20 carbon atoms, (1-4) a substituent-carrying silyl group having 1 to 20 carbon atoms, which substituent is a hydrocarbyl group, (1-5) a disubstituent-carrying amino group having 2 to 20 carbon atoms, which substituent is a hydrocarbyl group, (1-6) an alkoxy group having 1 to 20 carbon atoms, (1-7) an aralkyloxy group having 7 to 20 carbon atoms, and (1-8) an aryloxy group having 6 to 20 carbon atoms, (2) a halogen atom or (3) a hydrogen atom; $R^1$ and $R^2$, $R^2$ and $R^3$, and $R^3$ and $R^4$ may be linked to each other, respectively, to form respective rings; $R^5$ and $R^6$ may be linked to each other to form a ring; $R^{11}$ is a hydrocarbyl group or a three substituent-carrying silyl group; and $X^4$ is a halogen atom.

$R^7$, $R^8$, $R^9$ and $R^{10}$ in the general formula [4] are the same as $R^7$, $R^8$, $R^9$ and $R^{10}$ in the general formula [1], respectively.

$X^4$ in the general formula [5] is a halogen atom. Examples thereof are a fluorine atom, a chlorine atom, a bromine atom and an iodine atom. Among them, preferred is a chlorine atom.

Examples of the substituent-carrying fluorene compound represented by the general formula [4] are the following compounds: 2,7-difluorofluorene, 2,7-dichlorofluorene, 2,7-dibromofluorene, 2,7-diiodofluorene, 2,7-dimethylfluorene, 2,7-diethylfluorene, 2,7-di-n-propylfluorene, 2,7-diisopropylfluorene, 2,7-di-n-butylfluorene, 2,7-di-sec-butylfluorene, 2,7-di-tert-butylfluorene, 2,7-di-n-pentylfluorene, 2,7-di-neopentylfluorene, 2,7-di-n-hexylfluorene, 2,7-di-n-octylfluorene, 2,7-di-n-decylfluorene, 2,7-di-n-dodecylfluorene, 2,7-diphenylfluorene, 2,7-di(methylphenyl)fluorene, 2,7-dinaphthylfluorene, 2,7-bis(trimethylsilyl)fluorene, 2,7-bis(triethylsilyl)fluorene, 2,7-bis(tert-butyldimethylsilyl)fluorene, 2,7-dimethoxyfluorene, 2,7-diethoxyfluorene, 2,7-di-n-propoxyfluorene, 2,7-diisopropoxyfluorene, 2,7-di-n-butoxyfluorene, 2,7-di-tert-butoxyfluorene, 2,7-di-sec-butoxyfluorene, 2,7-bis(dimethylamino)fluorene, 2,7-bis(diethylamino)fluorene, 3,6-difluorofluorene, 3,6-dichlorofluorene, 3,6-dibromofluorene, 3,6-diiodofluorene, 3,6-dimethylfluorene, 3,6-diethylfluorene, 3,6-di-n-propylfluorene, 3,6-diisopropylfluorene, 3,6-di-n-butylfluorene, 3,6-di-sec-butylfluorene, 3,6-di-tert-butylfluorene, 3,6-di-n-pentylfluorene, 3,6-di-neopentylfluorene, 3,6-di-n-hexylfluorene, 3,6-di-n-octylfluorene, 3,6-di-n-decylfluorene, 3,6-di-n-dodecylfluorene, 3,6-diphenylfluorene, 3,6-di(methylphenyl)fluorene, 3,6-dinaphthylfluorene, 3,6-bis(trimethylsilyl)fluorene, 3,6-bis(triethylsilyl)fluorene, 3,6-bis(tert-butyldimethylsilyl)fluorene, 3,6-dimethoxyfluorene, 3,6-diethoxyfluorene, 3,6-di-n-propoxyfluorene, 3,6-diisopropoxyfluorene, 3,6-di-n-butoxyfluorene, 3,6-di-sec-butoxyfluorene, 3,6-di-tert-butoxyfluorene, 3,6-bis(dimethylamino)fluorene, and 3,6-bis(diethylamino)fluorene.

An example of a process for producing the substituent-carrying fluorene compound represented by the general formula [4] is a process disclosed in Organometallics, 23, 1777 (2004). The substituent-carrying fluorene compound represented by the general formula [4] may be a commercially available compound.

A, J, $R^1$, $R^2$, $R^3$, $R^4$, $R^5$ and $R^6$ in the general formula [5] are the same as A, J, $R^1$, $R^2$, $R^3$, $R^4$, $R^5$ and $R^6$ in the general formula [1], respectively.

$R^{11}$ in the general formula [5] is the same as $R^{11}$ in the general formula [2].

An example of a process for producing the compound represented by the general formula [5] is a process disclosed in JP 9-87313A.

An example of the base, which is reacted with the substituent-carrying fluorene compound represented by the general formula [4], is an organic alkali metal compound such as methyllithium, ethyllithium, n-butyllithium, sec-butyllithium, tert-butyllithium, lithiumtrimethylsilyl acetylide, lithium acetylide, trimethylsilylmethyllithium, vinyllithium, phenyllithium, and allyllithium; a metal hydride such as sodium hydride and potassium hydride; and a metal alkoxide such as sodium methoxide and potassium butoxide.

The base is used in an amount of generally 0.5 to 5 mol per one mol of the substituent-carrying fluorene compound represented by the general formula [4].

A process, which comprises the steps of (1) reacting the substituent-carrying fluorene compound represented by the general formula [4] with the base, and (2) reacting with the compound represented by the general formula [5], may be generally carried out according to a method comprising the steps of (i) adding the substituent-carrying fluorene compound represented by the general formula [4] and the base to a solvent, and (ii) adding thereto the compound represented by the general formula [5].

The compound represented by the general formula [5] is used in an amount of generally 1 to 200 parts by weight, and preferably 3 to 50 parts by weight per one part by weight of the substituent-carrying fluorene compound represented by the general formula [4].

The reaction temperature is generally $-100°$ C. to a boiling point of a solvent, and when using an organic alkali metal compound as the base, it is preferably $-80°$ C. to $40°$ C.

The reaction is carried out generally in a solvent inactive to the reaction. An example s of the solvent is a non-proton solvent such as an aromatic hydrocarbon solvent (for example, benzene and toluene); an aliphatic hydrocarbon solvent (for example, hexane and heptane); an ether solvent (for example, diethyl ether, tetrahydrofuran and 1,4-dioxane); an amide solvent (for example, hexamethylphosphoric amide and dimethylformamide); a polar solvent (for example, acetonitrile, propionitrile, acetone, diethyl ketone, methyl isobutyl ketone, and cyclohexanone); and a halogenated solvent (for example, dichloromethane, dichloroethane, chlorobenzene, and dichlorobenzene). Those solvents are used respectively or in combination of two or more thereof.

The obtained solution-state reaction mixture containing the substituent-carrying fluorene compound represented by the general formula [2] may be used directly in the next step, or may be treated according to a method comprising the steps of (1) adding thereto water or an acid aqueous solution, (2) separating an organic layer, (3) drying the organic layer, and (4) distilling away a solvent contained therein. A preferable method comprises the steps of (1) vacuum-distilling away a solvent contained in the obtained reaction mixture under a reduced pressure, (2) filtering off impurities using a hydrocarbon solvent, thereby obtaining a filtrate, (3) vacuum-concentrating the filtrate. Thus obtained the substituent-carrying fluorene compound represented by the general formula [2] may further be purified according to a method such as recrystallization, distillation, and column chromatography.

[Catalyst for Olefin Polymerization]

The catalyst for olefin polymerization of the present invention is a catalyst for olefin polymerization using the transition metal complex represented by the above general formula [1] as a catalyst component for olefin polymerization. Said catalyst is produced according to a process comprising the step of contacting the transition metal complex represented by the above general formula [1] with other co-catalyst component. Examples of said catalyst for olefin polymerization are those obtained by contacting the transition metal complex represented by the above general formula [1] with the following compound (A) and/or compound (B):

(A) one or more kinds of aluminum compounds selected from the group consisting of the following (A1) to (A3), (A1) an organoaluminum compound represented by the general formula, $E^1{}_a AlZ_{3-a}$, (A2) a cyclic aluminoxane having a structure represented by the general formula, $\{Al(E^2)\text{-O---}\}_b$, and (A3) a linear aluminoxane having a structure represented by the general formula, $E^3\{\text{-Al}(E^3)\text{-O---}\}_c AlE^3{}_2$ wherein a is a number satisfying $0<a\leqq 3$; b is an integer of 2 or more; c is an integer of 1 or more; $E^1$, $E^2$ and $E^3$ are independently of one another a hydrocarbyl group having 1 to 20 carbon atoms, and plural $E^1$s, $E^2$s and $E^3$s are the same as or different from one another, respectively; and Z is a hydrogen atom or a halogen atom, and plural Zs are the same as or different from one another, (B) one or more kinds of boron compounds selected from the group consisting of the following (B1) to (B3), (B1) a boron compound represented by the general formula, $BQ^1Q^2Q^3$, (B2) a boron compound represented by the general formula, $G^+(BQ^1Q^2Q^3Q^4)^-$, and (B3) a boron compound represented by the general formula, $(L^1\text{-H})^+(BQ^1Q^2Q^3Q^4)^-$, wherein B is a trivalent boron atom; $Q^1$, $Q^2$, $Q^3$ and $Q^4$ are independently of one another a halogen atom, a hydrocarbyl group, a halogenated hydrocarbyl group, a substituent-carrying silyl group, an alkoxy group, or a di-substituent-carrying amino group; $G^+$ is an inorganic or organic cation; and $L^1$ is a neutral Lewis base.

Examples of the organoaluminum compound (A1) represented by the general formula, $E^1{}_aAlZ_{3-a}$, are a trialkylaluminum such as trimethylaluminum, triethylaluminum, tripropylaluminum, triisobutylaluminum, and trihexylaluminum; a dialkylaluminum chloride such as dimethylaluminum chloride, diethylaluminum chloride, dipropylaluminum chloride, diisobutylaluminum chloride and dihexylaluminum chloride; an alkylaluminum dichloride such as methylaluminum dichloride, ethylaluminum dichloride, propylaluminum dichloride, isobutylaluminum dichloride and hexylaluminum dichloride; and a dialkylaluminum hydride such as dimethylaluminum hydride, diethylaluminum hydride, dipropylaluminum hydride, diisobutylaluminum hydride and dihexylaluminum hydride. Among them, preferred is a trialkylaluminum, and more preferred is triethylaluminum or triisobutylaluminum.

An example of $E^2$ in the cyclic aluminoxane (A2) having a structure represented by the general formula, $\{Al(E^2)\text{-O---}\}_b$, or an example of $E^3$ in the linear aluminoxane (A3) having a structure represented by the general formula, $E^3\{\text{-Al}(E^3)\text{-O---}\}_c AlE^3{}_2$, is an alkyl group such as are a methyl group, an ethyl group, a n-propyl group, an isopropyl group, a n-butyl group, an isobutyl group, a n-pentyl group, and a neopentyl group. b is an integer of 2 or more, and c is an integer of 1 or more. It is preferable that $E^2$ and $E^3$ are independently of each other a methyl group or an isobutyl group; b is 2 to 40; and c is 1 to 40.

The above-mentioned aluminoxanes can be produced according to any of many different processes. Those processes are not particularly limited, and may be those known in the art. Examples thereof are (1) a process comprising the step of contacting a solution of a trialkylaluminum (for example, trimethylaluminum) in a suitable organic solvent (for example, benzene and aliphatic hydrocarbon) with water, and (2) a process comprising the step of contacting a trialkylaluminum (for example, trimethylaluminum) with a crystal water-containing metal salt (for example, copper sulfate hydrate).

In the boron compound (B1) represented by the general formula, $BQ^1Q^2Q^3$, B is a trivalent boron atom. $Q^1$ to $Q^3$ are preferably, independently of one another, a halogen atom, a hydrocarbyl group having 1 to 20 carbon atoms, a halogenated hydrocarbyl group having 1 to 20 carbon atoms, a substituent-carrying silyl group having 1 to 20 carbon atoms, an alkoxy group having 1 to 20 carbon atoms, or a di-substituent-carrying amino group having 2 to 20 carbon atoms, and more preferably, independently of one another, a halogen atom, a hydrocarbyl group having 1 to 20-carbon atoms, or a halogenated hydrocarbyl group having 1 to 20 carbon atoms.

Examples of the boron compound (B1) represented by the general formula, $BQ^1Q^2Q^3$, are tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane and phenylbis(pentafluorophenyl)borane. Among them, preferred is tris(pentafluorophenyl)borane.

In the boron compound (B2) represented by the general formula, $G^+(BQ^1Q^2Q^3Q^4)^-$, $G^+$ is an inorganic or organic cation; B is a trivalent boron atom; and $Q^1$ to $Q^4$ are similar to and $Q^1$ to $Q^3$ in the above (B1).

In the boron compound (B2) represented by the general formula, $G^+(BQ^1Q^2Q^3Q^4)^-$, examples of the inorganic cation of $G^+$ are a ferrocenium cation, an alkyl substituent-carrying ferrocenium cation and a silver, cation, and an example of the organic cation of $G^+$ is a triphenylmethyl cation. Examples of $(BQ^1Q^2Q^3Q^4)^-$ are terakis(pentafluorophenyl)borate, terakis (2,3,5,6-teraafluorophenyl)borate, terakis(2,3,4,5-tetrafluorophenyl)borate, terakis(3,4,5-trifluorophenyl)borate, terakis (2,2,4-trifluorophenyl)borate, phenylbis(pentafluorophenyl) borate, and -terakis(3,5-bistrifluoromethylphenyl)borate.

Examples of the boron compound (B2) represented by the general formula, $G^+(BQ^1Q^2Q^3Q^4)^-$, are ferroceniumterakis (pentafluorophenyl)borate, 1,1'-dimethylferroceniumterakis (pentafluorophenyl)borate, silver terakis(pentafluorophenyl) borate, triphenylmethylterakis(pentafluorophenyl)borate, and triphenylmethylterakis(3,5-bistrifluoromethylphenyl) borate. Among them, preferred is triphenylmethylterakis (pentafluorophenyl)borate.

In the boron compound (B3) represented by the general formula, $(L^1\text{-H})^+(BQ^1Q^2Q^3Q^4)^-$, $L^1$ is a neutral Lewis base; $(L^1\text{-H})^+$ is a Broensted acid; B is a trivalent boron atom; and $Q^1$ to $Q^4$ are similar to and $Q^1$ to $Q^3$ in the above (B1).

In the boron compound (B3) represented by the general formula, $(L^1\text{-H})^+(BQ^1Q^2Q^3Q^4)^-$, examples of $(L^1\text{-H})^+$ are a trialkyl substituent-carrying ammonium, an N,N-dialkylanilinium, a dialkylammonium and a triarylphosphonium. Examples of the $(BQ^1Q^2Q^3Q^4)^-$ are the same as those mentioned above.

Examples of the boron compound (B3) represented by the general formula, $(L^1\text{-H})^+(BQ^1Q^2Q^3Q^4)^-$, are triethylammonium terakis(pentafluorophenyl)borate, tripropylammonium terakis(pentafluorophenyl)borate, tri(n-butyl)ammonium terakis(pentafluorophenyl)borate, tri(n-butyl)ammonium terakis(3,5-bistrifluoromethylphenyl)borate, N,N-dimethylanilinium terakis(pentafluorophenyl)borate, N,N-diethylanilinium terakis(pentafluorophenyl)borate, N,N-2,4, 6-pentamethylanilinium terakis(pentafluorophenyl)borate, N,N-dimethylanilinium terakis(3,5-bistrifluoromethylphenyl)borate, diisopropylammonium terakis(pentafluorophenyl)borate, dicyclohexylammonium terakis(pentafluorophenyl)borate, triphenylphosphonium terakis (pentafluorophenyl)borate, tri(methylphenyl)phosphonium terakis(pentafluorophenyl)borate, and tri(dimethylphenyl) phosphonium terakis(pentafluorophenyl)borate. Among the, preferred is tri(n-butyl)ammonium terakis(pentafluorophenyl)borate or N,N-dimethylanilinium terakis(pentafluorophenyl)borate.

As the compound (B), there is generally used any of the boron compounds (B1) represented by the general formula, BQ$^1$Q$^2$Q$^3$, (B2) represented by the general formula, G$^+$(BQ$^1$Q$^2$Q$^3$Q$^4$)$^-$, and (B3) represented by the general formula, (L$^1$-H)$^+$(BQ$^1$Q$^2$Q$^3$Q$^4$)$^-$.

A method for contacting respective catalyst components in a process for producing a catalyst for olefin polymerization may comprise the steps of (1) contacting any two catalyst components with each other in advance, and then (2) contacting with a remaining catalyst component. Respective catalyst components may be contacted with one another in a polymerization reactor; respective catalyst components may be added separately to a polymerization reactor in any order; or a preliminary contact product of any two or more of respective catalyst components may be added to a polymerization reactor. From a viewpoint of producing a higher molecular weight-carrying polymer, it is preferable to (i) contact preliminary the transition metal complex represented by the general formula [1] and the organoaluminum compound (A1) with each other, and (ii) contact preliminary the transition metal complex represented by the general formula [1] and the organoaluminum compound (A1) with each other, in the absence of a monomer.

The compound (A) is used in an amount of generally 0.1 to 10,000 mol (as an amount of an aluminum atom contained in the compound (A)), and preferably 5 to 2,000 mol (same as above), per one mol of the transition metal complex. When using the organoaluminum compound (A1) as the compound (A), the compound (A) is used in an amount of more preferably 0.3 to 500 mol (as an amount of an aluminum atom contained in the compound (A)), and further preferably 0.5 to 100 mol (same as above), per one mol of the transition metal complex. The compound (B) is used in an amount of generally 0.01 to 100, and preferably 0.5 to 10 mol per one mol of the transition metal complex.

When using respective catalyst components as respective solutions thereof, a concentration of the transition metal complex represented by the general formula [1] is generally 0.0001 to 5 mmol/liter, and preferably 0.001 to 1 mmol/liter; a concentration of the compound (A) is generally 0.01 to 500 mmol/liter (as an amount of an aluminum atom contained in the compound (A)), and preferably 0.1 to 100 mmol/liter (same as above); and a concentration of the compound (B) is generally 0.0001 to 5 mmol/liter, and preferably 0.001 to 1 mmol/liter.

A further example of a catalyst for olefin polymerization of the present invention is a catalyst produced according to a process comprising the step of contacting the transition metal complex represented by the above general formula [1], the above-mentioned compound (A) and the following compound (C) with one another:

(C) a compound produced by contacting the following compounds (C1) to (C3) with one another, (C1) a compound represented by the following general formula [6],

$$BiL^2_r \qquad [6],$$

(C2) a compound represented by the following general formula [7],

$$R^{12}_{s-1}T^1H \qquad [7], \text{and}$$

(C3) a compound represented by the following general formula [8],

$$R^{13}_{t-2}T^2H_2 \qquad [8]$$

wherein r is a number corresponding to a valence of Bi; L$^2$ is a halogen atom, a hydrocarbyl group, or a hydrocarbyloxy group, and when plural L$^2$s exist, they are the same as or different from one another; T$^1$ and T$^2$ are independently of each other the group 15 or 16 nonmetal atom in the periodic table of elements; S is a number corresponding to a valence of T$^1$; t is a number corresponding to a valence of T$^2$; R$^{12}$ is an electron-withdrawing group-containing group or an electron-withdrawing group, and when plural R$^{12}$s exist, they are the same as or different from one another; and R$^{13}$ is a hydrocarbyl group, and when plural R$^{13}$s exist, they are the same as or different from one another.

Bi in the general formula [6] is a bismuth atom; and r therein is a number corresponding to a valence of Bi, and is specifically 3 or 5, and preferably 3.

L$^2$ in the general formula [6] is a halogen atom, a hydrocarbyl group, or a hydrocarbyloxy group, and when plural L$^2$s exist, they are the same as or different from one another. Examples of the halogen atom in L$^2$ are a fluorine atom, a chlorine atom, a bromine atom and an iodine atom. The hydrocarbyl group in L$^2$ is preferably an alkyl group, an aryl group or an aralkyl group. The hydrocarbyloxy group in L$^2$ is preferably an alkoxy group or an aryloxy group.

Examples of the alkyl group in L$^2$ are a methyl group, an ethyl group, a n-propyl group, an isopropyl group, a n-butyl group, a sec-butyl group, a tert-butyl group, an isobutyl group, a n-pentyl group, a neopentyl group, a n-hexyl group, a n-octyl group, a n-decyl group, a n-dodecyl group, a n-pentadecyl group, and a n-eicosyl group.

Any of alkyl groups in L$^2$ may contain a substituent of a halogen atom such as a fluorine atom, a chlorine atom, a bromine atom and an iodine atom. Examples of the alkyl group containing a substituent of a halogen atom are a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, a perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group, and a perbromoeicosyl group.

Any of the alkyl groups as L may be substituted by an alkoxy group such as a methoxy group and an ethoxy group; an aryloxy group such as a phenoxy group; or an aralkyloxy group such as a benzyloxy group.

An alkyl group in L$^2$ is preferably an alkyl group having 1 to 20 carbon atoms; and more preferably a methyl group, an ethyl group, an isopropyl group, a n-butyl group, a tert-butyl group, or an isobutyl group.

Examples of the aryl group in L$^2$ are a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group.

Any of those aryl groups may be substituted by a halogen atom such as a fluorine atom, a chlorine atom, a bromine atom and an iodine atom; an alkyl group such as a methyl group, an ethyl group and an isopropyl group; an alkoxy group such as a methoxy group and an ethoxy group; an aryloxy group such as a phenoxy group; or an aralkyloxy group such as a benzyloxy group.

An aryl group in $L^2$ is preferably an aryl group having 6 to 20 carbon atoms, and more preferably a phenyl group or a tolyl group.

Examples of the aralkyl group in $L^2$ are a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-trimethylphenyl)methyl group, a (2,3,5-trimethylphenyl)methyl group, a (2,3,6-trimethylphenyl)methyl group, a (3,4,5-trimethylphenyl)methyl group, a (2,4,6-trimethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (n-tetradecylphenyl)methyl group, a naphthylmethyl group and an anthracenylmethyl group.

Any of those aralkyl groups may be substituted by a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

An aralkyl group in $L^2$ is preferably an aralkyl group having 7 to 20 carbon atoms, and more preferably a benzyl group.

Examples of the alkoxy group in $L^2$ are a methoxy group, an ethoxy group, a n-propoxy group, an isopropoxy group, a n-butoxy group, a sec-butoxy group, a tert-butoxy group, an isobutoxy group, a n-pentyloxy group, a neopentyloxy group, a tert-pentyloxy group, a n-hexyloxy group, a n-heptyloxy group, a n-octyloxy group, a n-decyloxy group, a n-dodecyloxy group, n-pentadecyloxy group, and a n-eicosoxy group.

Any of those alkoxy groups may be substituted by a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

An alkoxy group as $L^2$ is preferably an alkoxy group having 1 to 20 carbon atoms, and more preferably a methoxy group, an ethoxy group, an isopropoxy group, a tert-butoxy group, an isobutoxy group, a neopentyloxy group, or a tert-pentyloxy group.

Examples of the aryloxy group in $L^2$ are a phenoxy group, a 2-tolyloxy group, a 3-tolyloxy group, a 4-tolyloxy group, a 2,3-xylyloxy group, a 2,4-xylyloxy group, a 2,5-xylyloxy group, a 2,6-xylyloxy group, a 3,4-xylyloxy group, a 3,5-xylyloxy group, a 2,3,4-trimethylphenoxy group, 2,3,5-trimethylphenoxy group, a 2,3,6-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, an isobutylphenoxy group, a n-pentylphenoxy group, a neopentylphenoxy group, a n-hexylphenoxy group, a n-octylphenoxy group, a n-decylphenoxy group, a n-dodecylphenoxy group, a n-tetradecylphenoxy group, a naphthyloxy group, and an anthracenyloxy group.

Any of those aryl groups may be substituted by a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

An aryloxy group as $L^2$ is preferably an aryloxy group having 6 to 20 carbon atoms, and more preferably a phenoxy group.

$L^2$ is preferably a halogen atom, an alkyl group, an aryl group, an alkoxy group, or an aryloxy group; further preferably a halogen atom, an aryl group, an alkoxy group, or an aryloxy group; and particularly preferably an aryl group.

Examples of the compound (C1) represented by the above general formula [6] are a halogenated bismuth(III) such as bismuth(III) fluoride, bismuth(III) chloride, bismuth(III) bromide and bismuth(III) iodide; a trialkyl bismuth such as trimethylbismuth; a triarylbismuth such as triphenylbismuth; a trialkoxybismuth such as trimethoxybismuth, triethoxybismuth, triisoprpoxybismuth, tri(tert-butoxy)bismuth, triisobutoxybismuth, trineopentyloxybismuth and tri(tert-pentyloxy)bismuth; a triaryloxybismuth such as triphenoxybismuth, tri(2-tolyloxy)bismuth, tri(3-tolyloxy)bismuth, tri(4-tolyloxy)bismuth, tri(2,3-xylyloxy)bismuth, tri(2,4-xylyloxy)bismuth, tri(2,5-xylyloxy)bismuth, tri(2,6-xylyloxy)bismuth, tri(3,4-xylyloxy)bismuth, tri(3,5-xylyloxy)bismuth, tri(2,3,4-trimethylphenoxy)bismuth, tri(2,3,5-trimethylphenoxy)bismuth, tri(2,3,6-trimethylphenoxy)bismuth, tri(2,4,6-trimethylphenoxy)bismuth, tri(3,4,5-trimethylphenoxy)bismuth, tri(2,3,4,5-tetramethylphenoxy)bismuth, tri(2,3,4,6-tetramethylphenoxy)bismuth, tri(2,3,5,6-tetramethylphenoxy)bismuth, tri(pentamethylphenoxy)bismuth, tri(ethylphenoxy)bismuth, tri(n-propylphenoxy)bismuth, tri(isopropylphenoxy)bismuth, tri(n-butylphenoxy)bismuth, tri(sec-butylphenoxy)bismuth, tri(tert-butylphenoxy)bismuth, tri(isobutylphenoxy)bismuth, tri(n-pentylphenoxy)bismuth, tri(neopentylphenoxy)bismuth, tri(n-hexylphenoxy)bismuth, tri(n-octylphenoxy)bismuth, tri(n-decylphenoxy)bismuth, tri(n-dodecylphenoxy)bismuth, tri(n-tetradecylethylphenoxy)bismuth, trinaphtyloxybismuth, and trianthracenyloxybismuth; a halogenated bismuth (V) such as bismuth(V) fluoride, bismuth(V) chloride, bismuth(V) bromide, and bismuth(V) iodide; a pentaalkylbismuth such as pentamethylbismuth; a pentaalkoxybismuth such as pentamethoxybismuth and pentaethoxybismuth; and a pentaaryloxybismuth such as pentaphenoxybismuth.

(C1) is preferably a halogenated bismuth(III), a trialkyl bismuth, a triarylbismuth, a trialkoxybismuth, or a triaryloxybismuth; further preferably a halogenated bismuth(III), a triarylbismuth, a trialkoxybismuth, or a triaryloxybismuth; and particularly a triarylbismuth such as triphenylbismuth.

$T^1$ in the general formula [7] is the group 15 or 16 nonmetal atom in the periodic table of elements. Examples of the group 15 nonmetal atom are a nitrogen atom and a phosphorous atom, and examples of the group 16 nonmetal atom are an oxygen atom and a sulfur atom. $T^1$ is preferably a nitrogen atom or an oxygen atom, and more preferably an oxygen atom.

In the general formula [7], s is a number corresponding to a valence of $T^1$, and when $T^1$ is the group 15 atom, s is 3, and when $T^1$ is the group 16 atom, s is 2.

$R^{12}$ in the general formula [7] is an electron-withdrawing group-containing group or an electron-withdrawing group, and when plural $R^{12}$s exist, they are the same as or different from one another. An example of an index of an electron-withdrawing property is a substituent constant, σ, of Hammett's rule known in the art, and an example of the electron-withdrawing group is a functional group having a positive substituent constant, σ, of Hammett's rule.

Examples of the electron-withdrawing group are a fluorine atom, a chlorine atom, a bromine atom, an iodine atom, a cyano group, a nitro group, a carbonyl group, a sulfonyl group, and a phenyl group. Examples of the electron-withdrawing group-containing group are a halogenated hydrocarbyl group such as a halogenated alkyl group and a halogenated aryl group; a cyanated hydrocarbyl group such as a cyanated aryl group; a nitrated hydrocarbyl group such as a nitrated aryl group; a hydrocarbyloxycarbonyl group such as an alkoxycarbonyl group, an aralkyloxycarbonyl group, and an aryloxycarbonyl group; and an acyloxy group.

Examples of the halogenated alkyl group in $R^{12}$ are a fluoromethyl group, a chloromethyl group, a bromomethyl group, an iodomethyl group, a difluoromethyl group, a dichloromethyl group, a dibromomethyl group, a diiodomethyl group, a trifluoromethyl group, a trichloromethyl group, a tribromomethyl group, a triiodomethyl group, a 2,2,2-trifluoroethyl group, a 2,2,2-trichloroethyl group, a 2,2,2-tribromoethyl group, a 2,2,2-triiodoethyl group, a 2,2,3,3,3-pentafluoropropyl group, a 2,2,3,3,3-pentachloropropyl group, a 2,2,3,3,3-pentabromopropyl group, a 2,2,3,3,3-pentaiodopropyl group, a 2,2,2-trifluoro-1-trifluoromethylethyl group, a 2,2,2-trichloro-1-trichloromethylethyl group, a 2,2,2-tribromo-1-tribromomethylethyl group, a 2,2,2-triiodo-1-triiodomethylethyl group, a 1,1-bis(trifluoromethyl)-2,2,2-trifluoroethyl group, a 1,1-bis(trichloromethyl)-2,2,2-trichloroethyl group, a 1,1-bis(tribromomethyl)-2,2,2-tribromoethyl group, and a 1,1-bis(triiodomethyl)-2,2,2-triiodoethyl group.

An example of the halogenated aryl group in $R^{12}$ is an aryl group whose hydrogen atom in its aromatic ring is substituted by a halogen atom, such as a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,6-difluorophenyl group, a 3,5-difluorophenyl group, a 2,6-dichlorophenyl group, a 3,5-dichlorophenyl group, a 2,6-dibromophenyl group, a 3,5-dibromophenyl group, a 2,6-diiodophenyl group, a 3,5-diiodophenyl group, a 2,4,6-trifluorophenyl group, a 3,4,5-trifluorophenyl group, a 2,4,6-trichlorophenyl group, a 2,4,6-tribromophenyl group, a 2,4,6-triiodophenyl group, a pentafluorophenyl group, a pentachlorophenyl group, a pentabromophenyl group, and a pentaiodophenyl group.

An example of the halogenated aryl group in $R^{12}$ is an aryl group whose hydrogen atom in its aromatic ring is substituted by a halogenated aryl group, such as a 2-(trifluoromethyl) phenyl group, a 3-(trifluoromethyl)phenyl group, a 4-(trifluoromethyl)phenyl group, a 2,6-bis(trifluoromethyl)phenyl group, a 3,5-bis(trifluoromethyl)phenyl group, and a 2,4,6-tris(trifluoromethyl)phenyl group.

Examples of the cyanated aryl group in $R^{12}$ are a 2-cyanophenyl group, a 3-cyanophenyl group and a 4-cyanophenyl group.

Examples of the nitrated aryl group in $R^{12}$ are a 2-nitrophenyl group, a 3-nitrophenyl group and a 4-nitrophenyl group.

Examples of the alkoxycarbonyl group in $R^{12}$ are a methoxycarbonyl group, an ethoxycarbonyl group, a n-propoxycarbonyl group, an isopropoxycarbonyl group and a trifluoromethoxycarbonyl group.

An example of the aralkyloxycarbonyl group in $R^{12}$ is a benzyloxycarbonyl group.

Examples of the aryloxycarbonyl group in $R^{12}$ are a phenoxycarbonyl group and a pentafluorophenoxycarbonyl group.

Examples of the acyloxycarbonyl group in $R^{12}$ are a methylcarbonyloxy group and an ethylcarbonyloxy group.

$R^{12}$ is preferably a halogenated hydrocarbyl group; more preferably a halogenated alkyl group or a halogenated aryl group; further preferably a fluoroalkyl group, a fluoroaryl group, a chloroalkyl group, or a chloroaryl group; further more preferably a fluoroalkyl group or a fluoroaryl group; particularly preferably a fluoromethyl group, a difluoromethyl group, a trifluoromethyl group, a 2,2,2-trifluoroethyl group, a 2,2,3,3,3-pentafluoropropyl group, a 2,2,2-trifluoro-1-trifluoromethylethyl group, a 1,1-bis(trifluoromethyl)-2,2,2-trifluoroethyl group, a 4-fluorophenyl group, a 2,6-difluorophenyl group, a 3,5-difluorophenyl group, a 2,4,6-trifluorophenyl group, a 3,4,5-trifluorophenyl group, or a pentafluorophenyl group; and most preferably a fluoromethyl group, a 2,2,2-trifluoro-1-trifluoromethylethyl group, a 1,1-bis(trifluoromethyl)-2,2,2-trifluoroethyl group, a 3,4,5-trifluorophenyl group, or a pentafluorophenyl group.

Examples of amines in the compound (C2) represented by the above general formula [7] are di(fluoromethyl)amine, di(chloromethyl)amine, di(bromomethyl)amine, di(iodomethyl)amine, bis(difluoromethyl)amine, bis(dichloromethyl)amine, bis(dibromomethyl)amine, bis(diiodomethyl)amine, bis(trifluoromethyl)amine, bis(trichloromethyl)amine, bis(tribromomethyl)anine, bis(triiodomethyl)amine, bis(2,2,2-trifluoroethyl)amine, bis(2,2,2-trichloroethyl)amine, bis(2,2,2-tribromoethyl)amine, bis(2,2,2-triiodoethyl)amine, bis(2,2,3,3,3-pentafluoropropyl)amine, bis(2,2,3,3,3-pentachloropropyl)amine, bis(2,2,3,3,3-pentabromopropyl)amine, bis(2,2,3,3,3-pentaiodopropyl)amine, bis(2,2,2-trifluoro-1-trifluoromethylethyl)amine, bis(2,2,2-trichloro-1-trichloromethylethyl)amine, bis(2,2,2-tribromo-1-tribromomethylethyl)amine, bis(2,2,2-triiodo-1-triiodomethylethyl)amine, bis(1,1-bis(trifluoromethyl)-2,2,2-trifluoroethyl)amine, bis(1,1-bis(trichloromethyl)-2,2,2-trichloroethyl)amine, bis(1,1-bis(tribromomethyl)-2,2,2-tribromoethyl)amine, bis(1,1-bis(triiodomethyl)-2,2,2-triiodoethyl)amine, bis(2-fluorophenyl)amine, bis(3-fluorophenyl)amine, bis(4-fluorophenyl)amine, bis(2-chlorophenyl)amine, bis(3-chlorophenyl)amine, bis(4-chlorophenyl)amine, bis(2-bromophenyl)amine, bis(3-bromophenyl)amine, bis(4-bromophenyl)amine, bis(2-iodophenyl)amine, bis(3-iodophenyl)amine, bis(4-iodophenyl)amine, bis(2,6-difluorophenyl)amine, bis(3,5-difluorophenyl)amine, bis(2,6-dichlorophenyl)amine, bis(3,5-dichlorophenyl)amine, bis(2,6-dibromophenyl)amine, bis(3,5-dibromophenyl)amine, bis(2,6-diiodophenyl)amine, bis(3,5-diiodophenyl)amine, bis(2,4,6-trifluorophenyl)amine, bis(2,4,6-trichlorophenyl)amine, bis(2,4,6-tribromophenyl)amine, bis(2,4,6-triiodophenyl)amine, bis(pentafluorophenyl)amine, bis(pentachlorophenyl)amine, bis(pentabromophenyl)amine, bis(pentaiodophenyl)amine, bis(2-(trifluoromethyl)phenyl)amine, bis(3-(trifluoromethyl)phenyl)amine, bis(4-(trifluoromethyl)phenyl)amine, bis(2,6-di(trifluoromethyl)phenyl)amine, bis(3,5-di(trifluoromethyl)phenyl)amine, bis(2,4,6-tri(trifluoromethyl)phenyl)amine, bis(2-cyanophenyl)amine, bis(3-cyanophenyl)amine, bis(4-cyanophenyl)amine, bis(2-nitrophenyl)amine, bis(3-nitrophenyl)amine, and bis(4-nitrophenyl)amine.

Examples of phosphines in the compound (C2) represented by the above general formula [7] are those obtained by replacing respective nitrogen atoms contained in the above-exemplified amines with a phosphor atom.

Examples of alcohols in the compound (C2) represented by the above general formula [7] are fluoromethanol, chloromethanol, bromomethanol, iodomethanol, difluoromethanol, dichloromethanol, dibromomethanol, diiodomethanol, trifluoromethanol, trichloromethanol, tribromomethanol, triiodomethanol, 2,2,2-trifluoroethanol, 2,2,2-trichloroethanol, 2,2,2-tribromoethanol, 2,2,2-triiodoethanol, 2,2,3,3,3-pentafluoropropanol, 2,2,3,3,3-pentachloropropanol, 2,2,3,3,3-pentabromopropanol, 2,2,3,3,3-pentaiodopropanol, 2,2,2-trifluoro-1-trichloromethylethanol, 2,2,2-trichloro-1-trichloromethylethanol, 2,2,2-tribromo-1-tribromomethylethanol, 2,2,2-triiodo-1-triiodomethylethanol, 1,1-bis(trifluoromethyl)-2,2,2-trifluoroethanol, 1,1-bis(trichloromethyl)-2,2,2-trichloroethanol, 1,1-bis(tribromomethyl)-2,2,2-tribromoethanol, and 1,1-bis(triiodomethyl)-2,2,2-triiodoethanol.

Examples of thiols in the compound (C2) represented by the above general formula [7] are those obtained by replacing respective oxygen atoms contained in the above-exemplified alcohols with a sulfur atom; namely, those represented by replacing the terms of "methanol", "ethanol" and "propanol" contained in the above-exemplified alcohols with terms of "methanethiol", "ethanethiol" and "propanethiol", respectively.

Examples of phenols in the compound (C2) represented by the above general formula [7] are 2-fluorophenol, 3-fluorophenol, 4-fluorophenol, 2-chlorophenol, 3-chlorophenol, 4-chlorophenol, 2-bromophenol, 3-bromophenol, 4-bromophenol, 2-iodophenol, 3-iodophenol, 4-iodophenol, 2,6-difluorophenol, 3,5-difluorophenol, 2,6-dichlorophenol, 3,5-dichlorophenol, 2,6-dibromophenol, 3,5-dibromophenol, 2,6-diiodophenol, 3,5-diiodophenol, 2,4,6-trifluorophenol, 3,4,5-trifluorophenol, 2,4,6-trichlorophenol, 2,4,6-tribromophenol, 2,4,6-triiodophenol, pentafluorophenol, pentachlorophenol, pentabromophenol, pentaiodophenol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol, 2,4,6-tris(trifluoromethyl)phenol, 2-cyanophenol, 3-cyanophenol, 4-cyanophenol, 2-nitrophenol, 3-nitrophenol, and 4-nitrophenol.

Examples of thiophenols in the compound (C2) represented by the above general formula [7] are those obtained by replacing respective oxygen atoms contained in the above-exemplified phenols with a sulfur atom; namely, those represented by replacing the term of "phenol" contained in the above-exemplified phenols with a term of "thiophenol".

Examples of carboxylic acids in the compound (C2) represented by the above general formula [7] are 2-fluorobenzoic acid, 3-fluorobenzoic acid, 4-fluorobenzoic acid, 2,3-difluorobenzoic acid, 2,4-difluorobenzoic acid, 2,5-difluorobenzoic acid, 2,6-difluorobenzoic acid, 2,3,4-trifluorobenzoic acid, 2,3,5-trifluorobenzoic acid, 2,3,6-trifluorobenzoic acid, 2,4,5-trifluorobenzoic acid, 2,4,6-trifluorobenzoic acid, 2,3,4,5-tetrafluorobenzoic acid, 2,3,4,6-tetrafluorobenzoic acid, pentafluorobenzoic acid, fluoroacetic acid, difluoroacetic acid, trifluoroacetic acid, pentafluoropropanoic acid, heptafluorobutanoic acid, and 1,1-bis(trifluoromethyl)-2,2,2-trifluoroehtanoic acid.

Examples of sulfonic acids in the compound (C2) represented by the above general formula [7] are fluoromethanesulfonic acid, difluoromethanesulfonic acid, trifluoromethanesulfonic acid, pentafluoroethanesulfonic acid, heptafluoropropanesulfonic acid, and 1,1-bis(trifluoromethyl)-2,2,2-trifluoroehtane sulfonic acid.

An amine in the compound (C2) is preferably bis(trifluoromethyl)amine, bis(2,2,2-trifluoroethyl)amine, bis(2,2,3,3,3-pentafluoropropyl)amine, bis(2,2,2-trifluoro-1-trifluoromethylethyl)amine, bis(1,1-bis(trifluoromethyl)-2,2,2-trifluoroethyl)amine, or bis(pentafluorophenyl)amine; an alcohol therein is preferably trifluoromethanol, 2,2,2-trifluoroethanol, 2,2,3,3,3-pentafluoropropanol, 2,2,2-trifluoro-1-trifluoromethylethanol, or 1,1-bis(trifluoromethyl)-2,2,2-trifluoroethanol; a phenol therein is preferably 2-fluorophenol, 3-fluorophenol, 4-fluorophenol, 2,6-difluorophenol, 3,5-difluorophenol, 2,4,6-trifluorophenol, 3,4,5-trifluorophenol, pentafluorophenol, 2-(trifluoromethyl)phenol, 3-(trifluoromethyl)phenol, 4-(trifluoromethyl)phenol, 2,6-bis(trifluoromethyl)phenol, 5-bis(trifluoromethyl)phenol, or 2,4,6-tris(trifluoromethyl)phenol; a carboxylic acid therein is preferably pentafluorobenzoic acid or trifluoroacetic acid; and a sulfonic acid therein is preferably trifluoromethanesulfonic acid.

The compound (C2) is more preferably bis(trifluoromethyl)amine, bis(pentafluorophenyl)amine, trifluoromethanol, 2,2,2-trifluoro-1-trifluoromethylethanol, 1,1-bis(trifluoromethyl)-2,2,2-trifluoroethanol, 4-fluorophenol, 2,6-difluorophenol, 2,4,6-trifluorophenol, 3,4,5-trifluorophenol, pentafluorophenol, 4-(trifluoromethyl)phenol, 2,6-bis(trifluoromethyl)phenol, or 2,4,6-tris(trifluoromethyl)phenol; and further preferably 3,4,5-trifluorophenol, pentafluorophenol, or 1,1-bis(trifluoromethyl)-2,2,2-trifluoroethanol.

$T^2$ in the general formula [8] is the group 15 or 16 nonmetal atom in the periodic table of elements according to the revised IUPAC nomenclature of inorganic chemistry (1989). Examples of the group 15 nonmetal atom are a nitrogen atom and a phosphorous atom, and examples of the group 16 nonmetal atom are an oxygen atom and a sulfur atom. $T^2$ is preferably a nitrogen atom or an oxygen atom, and particularly preferably an oxygen atom.

In the general formula [8], t is a number corresponding to a valence of $T^2$, and when $T^2$ is the group 15 atom, t is 3, and when $T^2$ is the group 16 atom, t is 2.

$R^{13}$ in the general formula [8] is a hydrocarbyl group, and when plural $R^{13}$s exist, they are the same as or different from one another. The hydrocarbyl group in $R^{13}$ is preferably an alkyl group, an aryl group, or an aralkyl group. Examples of the hydrocarbyl group are the hydrocarbyl groups explained as the $L^2$ in the general formula [6], and the halogenated hydrocarbyl groups explained as the $R^{12}$ in the general formula [7].

$R^{11}$ is preferably a halogenated hydrocarbyl group, and further preferably a fluorinated hydrocarbyl group.

The compound (C3) represented by the above general formula [8] is preferably water, hydrogen sulfide, an alkylamine, an arylamine, or an aralkylamine; and further preferably water, hydrogen sulfide, methylamine, ethylamine, n-propylamine, isopropylamine, n-butylamine, sec-butylamine, tert-butylamine, isobutyl amine, n-pentylamine, neopentylamine, isopentylamine, n-hexylamine, n-octylamine, n-decylamine, n-dodecylamine, n-pentadecylamine, n-eicosylamine, allylamine, cyclopentadienylamine, aniline, 2-tolylamine, 3-tolylamine, 4-tolylamine, 2,3-xylylamine, 2,4-xylylamine, 2,5-xylylamine, 2,6-xylylamine, 3,4-xylylamine, 3,5-xylylamine, 2,3,4-trimethylaniline, 2,3,5-trimethylaniline, 2,3,6-trimethylaniline, 2,4,6-trimethylaniline, 3,4,5-trimethylaniline, 2,3,4,5-tetramethylaniline, 2,3,4,6-tetramethylaniline, 2,3,5,6-tetramethylaniline, pentamethylaniline, ethylaniline, n-propylaniline, isopropylaniline, n-butylaniline, sec-butylaniline, tert-butylaniline, n-pentylaniline, neopentylaniline, n-hexylaniline, n-octylaniline, n-decylaniline, n-dodecylaniline, n-tetradecylaniline, naphthylamine, anthracenylamine, benzylamine, (2-methylphenyl)methylamine, (3-methylphenyl)methylamine, (4-methylphenyl)methylamine, (2,3-dimethylphenyl)methylamine, (2,4-dimethylphenyl)methylamine, (2,5-dimethylphenyl)methylamine, (2,6-dimethylphenyl)methylamine, (3,4-dimethylphenyl)methylamine, (3,5-dimethylphenyl)methylamine, (2,3,4-trimethylphenyl)methylamine, (2,3,5-trimethylphenyl)methylamine, (2,3,6-trimethylphenyl)methylamine, (3,4,5-trimethylphenyl)methylamine, (2,4,6-trimethylphenyl)methylamine, (2,3,4,5-tetramethylphenyl)methylamine, (2,3,4,6-tetramethylphenyl)methylamine, (2,3,5,6-tetramethylphenyl)methylamine, (pentamethylphenyl)methylamine, (ethylphenyl)methylamine, (n-propylphenyl)methylamine, (isopropylphenyl)methylamine, (n-butylphenyl)methylamine, (sec-butylphenyl)methylamine, (tert-butylphenyl)methylamine, (n-pentylphenyl)methylamine, (neopentylphenyl)methylamine, (n-hexylphenyl)methylamine, (n-octylphenyl)methylamine, (n-decylphenyl)methylamine, (n-tetradecylphenyl)methylamine, naphtylmethylamine, anthracenylmethylamine, fluoromethylamine, chloromethylamine, bromomethylamine, iodomethylamine, difluoromethylamine, dichloromethylamine, dibromomethylamine, diiodomethylamine, trifluoromethylamine, trichloromethylamine, tribromomethylamine, triiodomethylamine, 2,2,2-trifluoroethylamine, 2,2,2-trichloroethylamine, 2,2,2-tribromoethylamine, 2,2,2-triiodoethylamine, 2,2,3,3,3-pentafluoropropylamine, 2,2,3,3,3-pentachloropropylamine, 2,2,3,3,3-pentabromopropylamine, 2,2,3,3,3-pentaiodopropylamine, 2,2,2-trifluoro-1-trifluoromethylethylamine, 2,2,2-trichloro-1-trichloromethylethylamine, 2,2,2-tribromo-1-tribromomethylethylamine, 2,2,2-triiodo-1-triiodomethylethylamine, 1,1-bis(trifluoromethyl)-2,2,2-trifluoroethylamine, 1,1-bis(trichloromethyl)-2,2,2-trichloroethylamine, 1,1-bis(tribromomethyl)-2,2,2-tribromoethylamine, 1,1-bis(triiodomethyl)-2,2,2-triiodoethylamine, 2-fluoroaniline, 3-fluoroaniline, 4-fluoroaniline, 2-chloroaniline, 3-chloroaniline, 4-chloroaniline, 2-bromoaniline, 3-bromoaniline, 4-bromoaniline, 2-iodoaniline, 3-iodoaniline, 4-iodoaniline, 2,6-difluoroaniline, 3,5-difluoroaniline, 2,6-dichloroaniline, 3,5-dichloroaniline, 2,6-dibromoaniline, 3,5-dibromoaniline, 2,6-diiodoaniline, 3,5-diiodoaniline, 2,4,6-trifluoroaniline, 2,4,6-trichloroaniline, 2,4,6-tribromoaniline, 2,4,6-triiodoaniline, pentafluoroaniline, pentachloroaniline, pentabromoaniline, pentaiodoaniline, 2-(trifluoromethyl)aniline, 3-(trifluoromethyl)aniline, 4-(trifluoromethyl)aniline, 2,6-di(trifluoromethyl)aniline, 3,5-di(trifluoromethyl)aniline, or 2,4,6-tri(trifluoromethyl)aniline.

The compound (C3) is more preferably water, hydrogen sulfide, methylamine, ethylamine, n-propylamine, isopropylamine, n-butylamine, sec-butylamine, tert-butylamine, isobutyl amine, n-octylamine, aniline, 2,6-xylylamine, 2,4,6-trimethylaniline, naphthylamine, anthracenylamine, benzylamine, trifluoromethylamine, pentafluoroethylamine, perfluoropropylamine, perfluorobutylamine, perfluoropentylamine, perfluorohexylamine, perfluorooctylamine, perfluorododecylamine, perfluoropentadecylamine, perfluoroeicosylamine, 2-fluoroaniline, 3-fluoroaniline, 4-fluoroaniline, 2,6-difluoroaniline, 3,5-difluoroaniline, 2,4,6-trifluoroaniline, pentafluoroaniline, 2-(trifluoromethyl)aniline, 3-(trifluoromethyl)aniline, 4-(trifluoromethyl)aniline, 2,6-bis(trifluoromethyl)aniline, 3,5-bis(trifluoromethyl)aniline, or 2,4,6-tris(trifluoromethyl)aniline.

The compound (C3) is particularly preferably water, trifluoromethylamine, perfluorobutylamine, perfluorooctylamine, perfluoropentadecylamine, 2-fluoroaniline, 3-fluoroaniline, 4-fluoroaniline, 2,6-difluoroaniline, 3,5-difluoroaniline, 2,4,6-trifluoroaniline, pentafluoroaniline, 2-(trifluoromethyl)aniline, 3-(trifluoromethyl)aniline, 4-(trifluoromethyl)aniline, 2,6-bis(trifluoromethyl)aniline, 3,5-bis(trifluoromethyl)aniline, or 2,4,6-tris(trifluoromethyl)aniline; and most preferably water or pentafluoroaniline.

The compound (C) is a compound obtained by contacting the above-mentioned compounds (C1), (C2) and (C3) with one another. Contacting the compounds (C1), (C2) and (C3) with one another is preferably carried out in an inactive gas atmosphere. Its contact temperature is generally −100 to 200° C., preferably −80 to 150° C., more preferably 10 to 150° C., and further preferably 40 to 100° C. Its contact time is generally 1 minute to 36 hours, and preferably 10 minutes to 24 hours.

Contacting the compounds (C1), (C2) and (C3) with one another is carried out with or without a solvent, and preferably with a solvent. Examples of the solvent are a non-polar solvent such as an aliphatic hydrocarbon solvent and an aromatic hydrocarbon solvent; and a polar solvent such as a halogenated compound solvent and an ether solvent. Specific examples of the solvent are an aliphatic hydrocarbon solvent such as butane, pentane, hexane, heptane, octane, 2,2,4-trimethylpentane, and cyclohexane; an aromatic hydrocarbon solvent such as benzene, toluene, and xylene; a halogenated compound solvent such as dichloromethane, difluoromethane, chloroform, 1,2-dichloroethane, 1,2-dibromoethane, 1,1,2-trichloro-1,2,2-trifluoroethane, tetrachloroethylene, chlorobenzene, bromobenzene and o-dichlorobenzene; and an ether solvent such as dimethyl ether, diethyl ether, diisopropyl ether, di-n-butyl ether, methyl-tert-butyl ether, anisole, 1,4-dioxane, 1,2-dimethoxyethane, bis(2-methoxyethyl)ether, tetrahydrofuran and tetrahydropyran. Among them, preferred is an aliphatic hydrocarbon solvent, an aromatic hydrocarbon solvent, or an ether solvent; more preferred is an aromatic hydrocarbon solvent; and further preferred is toluene.

A method for contacting the above-mentioned compounds (C1), (C2) and (C3) with one another is not particularly limited. Examples thereof are the following methods (1) to (3)

(1) a method comprising the steps of (1-1) contacting the compound (C1) with the compound (C2), and then (1-2) contacting with the compound (C3), (2) a method comprising the steps of (2-1) contacting the compound (C1) with the compound (C3), and then (2-2) contacting with the compound (C2), and (3) a method comprising the steps of (3-1) contacting the compound (C2) with the compound (C3), and then (3-2) contacting with the compound (C1).

Among them, preferred is the method (1) or (2), and more preferred is the method (1). Regarding the method (1), it preferably comprises the steps of (1-1) contacting the compound (C1) with the compound (C2), thereby obtaining a contact product, and then (1-2) contacting a solution of the contact product in a solvent with the compound (C3). The contact products obtained in the above-mentioned respective first steps (1-1), (2-1) and (3-1) may be purified before the above-mentioned respective second steps (1-2), (2-2) and (3-2).

In order to improve a catalyst activity, each of the compounds (C1) to (C3) is used in an amount satisfying the following condition: when a molar ratio of (C1):(C2):(C3) is 1:y:z, y is preferably 0.7×r to 1.3×r, more preferably 0.8×r to 1.2×r, and further preferably 0.9×r to 1.1×r, wherein r is a number corresponding to a valence of Bi, and z is preferably 0.1 to 2, more preferably 0.4 to 1.8, further preferably 0.6 to 1.6, particularly preferably 0.8 to 1.4, and most preferably 0.9 to 1.3.

The compound (C), which is obtained by contacting the compounds (C1), (C2) and (C3) with one another, may contain one or more of the compounds (C1), (C2) and (C3) as starting materials.

[Process for Producing Olefin Polymer]

A process for producing an olefin polymer of the present invention comprises the step of polymerizing an olefin in the presence of a catalyst for olefin polymerization using the transition metal complex represented by the above general formula [1] as a catalyst component for olefin polymerization.

Examples of the olefin are linear olefins and cyclic olefins, and those olefins may be used for homopolymerization, respectively, or may be used in combination of two or more thereof for copolymerization. There are generally used an olefin having 2 to 20 carbon atoms.

Examples of the linear olefin are ethylene; an α-olefin having 3 to carbon atoms such as propylene, 1-butene, 1-pentene, 1-hexene, 1-heptene, 1-octene, 1-nonene, 1-decene, 3-methyl-1-pentene, 4-methyl-1-pentene, 3,3-dimethyl-1-butene, 5-methyl-1-hexene, and 3,3-dimethyl-1-pentene; a non-conjugated diene such as 1,5-hexadiene, 1,4-hexadiene, 1,4-pentadiene, 1,5-heptadiene, 1,6-heptadiene, 1,6-octadiene, 1,7-octadiene, 1,7-nonadiene, 1,8-nonadiene, 1,8-decadiene, 1,9-decadiene, 1,12-tetradecadiene, 1,13-tetradecadiene, 4-methyl-1,4-hexadiene, 5-methyl-1,4-hexadiene, 7-methyl-1,6-octadiene, 3-methyl-1,4-hexadiene, 3-methyl-1,5-hexadiene, 3-ethyl-1,4-hexadiene, 3-ethyl-1,5-hexadiene, and 3,3-dimethyl-1,4-hexadiene, 3,3-dimethyl-1,5-hexadiene; and a conjugated diene such as 1,3-butadiene, isoprene, 1,3-hexadiene, and 1,3-octadiene.

Regarding examples of the cyclic olefin, examples of an aliphatic cyclic olefin are a monoolefin such as vinylcyclopentane, vinylcyclohexane, vinylcycloheptane, norbornene, 5-methyl-2-norbornene, 5-ethyl-2-norbornene, 5-butyl-2-norbornene, tetracyclododecene, tricyclodecene, tricycloundecene, pentacyclopentadecene, pentacyclohexadecene, and 8-methyltetracyclododecene, 8-ethyltetracyclododecene; a non-conjugated diene such as 5-ethylidene-2-norbornene, dicyclopentadiene, 5-vinyl-2-norbornene, norbornadiene, 5-methyl-2-norbornene, 1,5-cyclooctadiene, 7-methyl-2,5-norbornadiene, 7-ethyl-2,5-norbornadiene, 7-propyl-2,5-norbornadiene, 7-butyl-2,5-norbornadiene, 7-pentyl-2,5-norbornadiene, 7-hexyl-2,5-norbornadiene, 7,7-dimethyl-2,5-norbornadiene, 7,7-methylethyl-2,5-norbornadiene, 7-chloro-2,5-norbornadiene, 7-bromo-2,5-norbornadiene, 7-fluoro-2,5-norbornadiene, 7,7-dichloro-2,5-norbornadiene, 1-methyl-2,5-norbornadiene, 1-ethyl-2,5-norbornadiene, 1-propyl-2,5-norbornadiene, 1-butyl-2,5-norbornadiene, 1-chloro-2,5-norbornadiene, 1-bromo-2,5-norbornadiene, 5,8-endomethylenehexahydronaphthalene, and vinylcyclohexene; and a conjugated diene such as 1,3-cyclooctadiene and 1,3-cyclohexadiene. Examples of an aromatic cyclic olefin are styrene, o-methylstyrene, m-methylstyrene, p-methylstyrene, o,p-dimethylstyrene, o-ethylstyrene, m-ethylstyrene, p-ethylstyrene, α-methylstyrene, and divinylbenzene.

Examples of a combination of olefins for copolymerizing olefins are a linear olefin/linear olefin-combination such as ethylene/propylene, ethylene/1-butene, ethylene/1-hexene, ethylene/propylene/1-butene, ethylene/propylene/1-hexene, propylene/1-butene, and propylene/1-hexene; and a linear olefin/cyclic olefin-combination such as ethylene/vinylcyclohexane, ethylene/norbornene, ethylene/tetracyclododecene, ethylene/5-ethylidene-2-norbornene, propylene/vinylcyclohexane, propylene/norbornene, propylene/tetracyclododecene, propylene/5-ethylidene-2-norbornene, and ethylene/propylene/5-ethylidene-2-norbornene.

As the transition metal complex represented by the above general formula [1] used as a catalyst component for olefin polymerization of a catalyst for olefin polymerization, it is preferable that $R^7$ and $R^9$ among $R^7$, $R^8$, $R^9$ and $R^{10}$ in the general formula [1] are a substituent selected from the above-mentioned group or a halogen atom in case of homopolymerization of a linear olefin or in case of copolymerization of a linear olefin/linear olefin-combination, particularly in case of copolymerization of an ethylene/α-olefin-combination. Further, it is more preferable that both $R^8$ and $R^{10}$ are a substituent selected from the above-mentioned group or a halogen, or both $R^8$ and $R^{10}$ are a hydrogen atom. In case of copolymerization of a linear olefin/cyclic olefin-combination, particularly in case of copolymerization of an ethylene/cyclic olefin-combination, it is preferable that at least one of $R^8$ and $R^{10}$ among $R^7$, $R^8$, $R^9$ and $R^{10}$ in the general formula [1] is a substituent selected from the above-mentioned group or a halogen atom, and is more preferable that $R^8$ and $R^{10}$ are a substituent selected from the above-mentioned group or a halogen atom. It is preferable that at least one of $R^7$ and $R^9$ is a hydrogen atom, and more preferable that $R^7$ and $R^9$ are a hydrogen atom.

A polymerization method is not particularly limited. Examples thereof are a solvent-polymerization method and a slurry-polymerization method, which use a solvent of an aliphatic hydrocarbon (for example, butane, pentane, hexane, heptane and octane), an aromatic hydrocarbon (for example, benzene and toluene) or a halogenated hydrocarbon (for example, methylene dichloride); and a gas phase-polymerization method carried out in a gaseous monomer. Those polymerization methods are a continuous polymerization method or a batch-wise polymerization method.

A polymerization temperature may be in a range of −50° C. to 300° C., and particularly preferably in a range of −20° C. to 250° C. A polymerization pressure is preferably an atmospheric pressure to 90 MPa. A polymerization time is suitably determined generally according to a kind of a target polymer and a polymerization reactor, and may be in a range of 1 minute to 20 hours. In the present invention, a chain transfer agent such as hydrogen can be added to a polymerization reactor in order to control a molecular weight of a polymer.

EXAMPLE

The present invention is explained in more detail with reference to the following Examples.

<Production of Substituent-Carrying Fluorene Compound and Transition Metal Complex>

The following measurement methods were used to identify a chemical structure.

(1) Proton Nuclear Magnetic Resonance Spectrum ($^1$H-NMR)
  Apparatus: EX270 manufactured by JEOL LTD, or DPX-300 manufactured by Bruker
  Sample cell: 5 mmΦ tube
  Measurement solvent: $CDCl_3$ or $C_6D_6$
  Sample concentration: 10 mg/0.5 mL ($CDCl_3$ or $C_6D_6$)
  Measurement temperature: room temperature (about 25° C.)
  Measurement parameter: 5 mmΦ probe, MENUF NON, OBNUC H, and integrating number of 16
  Pulse angle: 45°
  Repetition time: three seconds for ACQTM, and four seconds for PD
  Internal standard: $CDCl_3$ (7.26 ppm) or $C_6D_6$ (7.15 ppm)
(2) Carbon Nuclear Magnetic Resonance Spectrum ($^{13}$C-NMR)
  Apparatus: EX270 manufactured by JEOL LTD
  Sample cell: 5 mmΦ tube
  Measurement solvent: $CDCl_3$
  Sample concentration: 30 mg/0.5 mL ($CDCl_3$)
  Measurement temperature: room temperature (about 25° C.)
  Measurement parameter: 5 mmΦ probe, MENUF BCM, OBNUC $^{13}$C, and integrating number of 256
  Pulse angle: 45°
  Repetition time: 1.8 second for ACQTM, and 1.2 second for PD
  Internal standard: $CDCl_3$ (77.47, 77.00 and 76.53 ppm)
(3) Mass Spectrum
[Electron Ionization Mass Analysis (EI-MS)]
  Apparatus: JMS-AX505W manufactured by JEOL LTD
  Ionization voltage: 70 eV
  Ionization source temperature: 230° C.
  Data handling equipment: MS-MP8020D
  Mass range: m/z 35-1000
[Field Desorption Ionization Mass Analysis (FD-MS)]
  Apparatus: JMS-SX102 manufactured by JEOL LTD
  Accelerating voltage: 8 kV
  Carbon Emitter
  Data handling equipment: MS-MP8020D
  Cathode: 0 kV
  Mass range: m/z 10-2000

Example 1

Synthesis of (2-allyloxy-3-tert-butyl-5-methylphenyl)chlorodimethylsilane

There was obtained (2-allyloxy-3-tert-butyl-5-methylphenyl)chlorodimethylsilane according to the method disclosed in JP 9-87313A, Example 21.

Synthesis of (2-allyloxy-3-tert-butyl-5-methylphenyl)(2,7-di-tert-butylfluoren-9-yl)dimethylsilane There was washed 3.00 g (22.45 mmol) of potassium hydride having a purity of 30% by weight with each 6 mL of hexane three times in an atmosphere of nitrogen, and 32 mL of tetrahydrofuran (referred to as "THF" hereinafter) was added thereto. To the obtained THF slurry of potassium hydride, 5.00 g (17.96 mml) of 2,7-di-tert-butylfluorene was added dropwise at 0° C. using 32 mL of a THF solution thereof. The obtained mixture was stirred for 2.5 hours at a room temperature, and then 5.33 g (17.96 mmol) of (2-allyloxy-3-tert-butyl-5-methylphenyl)chlorodimethylsilane was added dropwise at −78° C. using 6 mL of a toluene solution thereof. The temperature of the obtained liquid reaction mixture was raised up to a room temperature, and the mixture was stirred for 2.5 hours. The mixture was added dropwise at 0° C. to a mixture of 32 mL of a 10% aqueous solution of sodium hydrogen carbonate and 32 mL of a 10% aqueous solution of sodium carbonate, and the resultant mixture was extracted with 20 mL of toluene. The obtained extract was dried over sodium sulfate, and the solvent contained therein was distilled away under a reduced pressure, thereby obtaining quantitatively (2-allyloxy-3-tert-butyl-5-methylphenyl)(2,7-di-tert-butylfluoren-9-yl)dimethylsilane.

Its $^1$H-NMR ($CDCl_3$, δ (ppm)) showed the results: −0.02 (s, 6H), 1.23 (s, 18H), 1.45 (s, 9H), 2.28 (s, 3H), 4.32 to 4.40 (m, 3H), 5.33 (d, J=10.8 Hz, 1H), 5.62 (d, J=17.3 Hz, 1H), 6.00 to 6.15 (m, 1H), 6.97 (s, 1H), 7.10 to 7.30 (m, 5H), and 7.67 (d, J=8.0 Hz, 2H).

Its mass spectrum (EI, m/z) showed 538 ($M^+$) and 261.

Example 2

Synthesis of dimethylsilylene(2,7-di-tert-butylfluoren-9-yl)(3-tert-butyl-5-methyl-2-phenoxy)titanium dichloride (Referred to as "Complex (1)" Hereinafter)

There was added dropwise at −78° C. 9.11 mmol of n-butyllithium using 5.77 mL of its hexane solution having a concentration of 1.58 mol/L to 48 mL of a toluene solution containing 2.18 g (4.05 mmol) of (2-allyloxy-3-tert-butyl-5-methylphenyl)(2,7-di-tert-butyl fluoren-9-yl)dimethylsilane and 1.84 g (18.23 mmol) of triethylamine, and the resultant mixture was stirred for 10 minutes, and then for 2 hours at a room temperature. To the obtained reaction mixture solution, 1.15 g (6.08 mmol) of titanium tetrachloride was added dropwise at −78° C. using 6.0 mL of its toluene solution, and the temperature of the resultant mixture was raised up to a room temperature, and then the mixture was stirred at 90° C. for 3 hours. The obtained mixture was concentrated, and the solid contained in the concentrated product was filtered off. The resultant solid was washed with hexane in order to remove impurities, and the solvent contained in the washed solid was distilled away under a reduced pressure, thereby obtaining the solid. The solid was recrystallized from pentane, thereby obtaining 0.09 g (yield: 3.7%) of the complex (1) as a brown solid.

Its $^1$H-NMR($C_6D_6$, δ (ppm)) showed the results: 0.08 (s, 6H), 1.19 (s, 18H), 1.35 (s, 9H), 2.25 (s, 3H), 7.19 (s, 1H), 7.34 (s, 1H), 7.45 (d, J=9.0 Hz, 2H), 7.76 (s, 2H), and 8.01 (d, J=9.0 Hz, 2H).

Its mass spectrum (EI, m/z) showed 614 ($M^+$).

Example 3

Synthesis of dimethylsilylene(2,7-di-tert-butylfluoren-9-yl)(3-tert-butyl-5-methyl-2-phenoxy)zirconium dichloride (Referred to as "Complex (2)" Hereinafter)

There was added dropwise at −78° C. 9.11 mmol of n-butyllithium using 5.81 mL of its hexane solution having a concentration of 1.57 mol/L to 48 mL of a toluene solution containing 2.18 g (4.05 mmol) of (2-allyloxy-3-tert-butyl-5-methylphenyl)(2,7-di-tert-butyl fluoren-9-yl)dimethylsilane and 1.84 g (18.23 mmol) of triethylamine, and the resultant mixture was stirred for 10 minutes, and then for 2 hours at a room temperature. The obtained reaction mixture solution was dropped at −78° C. to 6.0 mL of a toluene suspension containing 1.42 g (6.08 mmol) of zirconium tetrachloride, and the temperature of the resultant mixture was raised up to a room temperature, and then the mixture was stirred at 90° C. for 3 hours. The obtained mixture was concentrated, and the solid contained in the concentrated product was filtered off. The resultant solid was washed with hexane in order to remove impurities, and the solvent contained in the washed solid was distilled away under a reduced pressure, thereby obtaining the solid. The solid was recrystallized from pentane, thereby obtaining the complex (2) as a pale yellow solid.

Its $^1$H-NMR($C_6D_6$, δ (ppm)) showed the results: 0.82 (s, 6H), 1.19 (s, 18H), 1.36 (s, 9H), 2.27 (s, 3H), 7.22 (s, 1H), 7.38 (s, 1H), 7.39 (d, J=8.8 Hz, 2H), 7.82 (s, 2H), and 7.93 (d, J=8.8 Hz, 2H).

Its mass spectrum (EI, m/z) showed 658 ($M^+$).

Example 4

Synthesis of dimethylsilylene(2,7-di-tert-butylfluoren-9-yl)(3-tert-butyl-5-methyl-2-phenoxy)hafnium dichloride (Referred to as "Complex (3)" Hereinafter)

There was added dropwise at −78° C. 9.11 mmol of n-butyllithium using 5.81 mL of its hexane solution having a concentration of 1.57 mol/L to 48 mL of a toluene solution containing 2.18 g (4.05 mmol) of (2-allyloxy-3-tert-butyl-5-methylphenyl)(2,7-di-tert-butyl fluoren-9-yl)dimethylsilane and 1.84 g (18.23 mmol) of triethylamine, and the resultant mixture was stirred for 10 minutes, and then for 2 hours at a room temperature. The obtained reaction mixture solution was dropped at −78° C. to 6.0 mL of a toluene suspension containing 1.95 g (6.08 mmol) of hafnium tetrachloride, and the temperature of the resultant mixture was raised up to a room temperature, and then the mixture was stirred at 90° C. for 3 hours. The obtained mixture was concentrated, and the solid contained in the concentrated product was filtered off. The resultant solid was washed with hexane in order to remove impurities, and the solvent contained in the washed solid was distilled away under a reduced pressure, thereby obtaining the solid. The solid was recrystallized from pentane, thereby obtaining 0.16 g (yield: 5.4%) of the complex (3) as a pale yellow solid.

Its $^1$H-NMR($C_6D_6$, δ (ppm)) showed the results: 0.83 (s, 6H), 1.20 (s, 18H), 1.36 (s, 9H), 2.29 (s, 3H), 7.26 (s, 1H), 7.38 (d, J=8.9 Hz, 2H), 7.39 (s, 1H), 7.85 (s, 2H), and 7.93 (d, J=8.9 Hz, 2H).

Its mass spectrum (EI, m/z) showed 746 ($M^+$).

Example 5

Synthesis of (2-allyloxy-3-tert-butyl-5-methylphenyl)chlorodiethylsilane

There was obtained (2-allyloxy-3-tert-butyl-5-methylphenyl)chlorodiethylsilane using dichlorodiethylsilane according to a method similar to that of Example 1.

Synthesis of (2-allyloxy-3-tert-butyl-5-methylphenyl)(2,7-di-tert-butylfluoren-9-yl)diethylsilane There was washed 3.00 g (22.45 mmol) of potassium hydride having a purity of 30% by weight with each 6 mL of hexane three times in an atmosphere of nitrogen, and 37 mL of THF was added thereto. To the obtained THF slurry of potassium hydride, 5.00 g (17.96 mml) of 2,7-di-tert-butylfluorene was added dropwise at 0° C. using 32 mL of a THF solution thereof. The obtained mixture was stirred for 2.5 hours at a room temperature, and then 5.84 g (17.96 mmol) of (2-allyloxy-3-tert-butyl-5-methylphenyl)chlorodiethylsilane was added dropwise at −78° C. using 7 mL of a toluene solution thereof. The temperature of the obtained liquid reaction mixture was raised up to a room temperature, and the mixture was stirred for 2.5 hours. The mixture was added dropwise at 0° C. to a mixture of 32 mL of a 10% aqueous solution of sodium hydrogen carbonate and 32 mL of a 10% aqueous solution of sodium carbonate, and the resultant mixture was extracted with 20 mL of toluene. The obtained extract was dried over sodium sulfate, and the solvent contained therein was distilled away under a reduced pressure, thereby obtaining quantitatively (2-allyloxy-3-tert-butyl-5-methylphenyl)(2,7-di-tert-butyl fluoren-9-yl)diethylsilane.

Its $^1$H-NMR (CDCl$_3$, δ (ppm)) showed the results: 0.42 to 0.64 (m, 6H), 0.72 to 1.00 (m, 4H), 1.25 (s, 18H), 1.43 (s, 9H), 2.28 (s, 3H), 4.39 (br s, 2H), 4.46 (s, 1H), 5.30 (d, J=10.4 Hz, 1H), 5.57 (d, J=17.3 Hz, 1H), 5.99 to 6.11 (m, 1H), 6.96 (s, 1H), 7.09 to 7.32 (m, 5H), and 7.67 (d, J=8.0 Hz, 2H).

Example 6

Synthesis of diethylsilylene(2,7-di-tert-butylfluoren-9-yl)(3-tert-butyl-5-methyl-2-phenoxy)titanium dichloride (Referred to as "Complex (4)" Hereinafter)

There was added dropwise at −78° C. 9.76 mmol of n-butyllithium using 6.22 mL of its hexane solution having a concentration of 1.57 mol/L to 45 mL of a toluene solution containing 2.46 g (4.34 mmol) of (2-allyloxy-3-tert-butyl-5-methylphenyl)(2,7-di-tert-butylfluoren-9-yl)diethylsilane and 1.98 g (19.53 mmol) of triethylamine, and the resultant mixture was stirred for 10 minutes, and then for 2 hours at a room temperature. To the obtained reaction mixture solution, 1.23 g (6.51 mmol) of titanium tetrachloride was added dropwise at −78° C. using 7 mL of its toluene solution, and the temperature of the resultant mixture was raised up to a room temperature, and then the mixture was stirred at 95° C. for 3 hours. The obtained mixture was cooled, and concentrated, and then the solid contained in the concentrated product was filtered off. The resultant solid was washed with hexane in order to remove impurities. The solvent contained in the washed solid was distilled away under a reduced pressure, and the resultant solid was washed with pentane, thereby obtaining 0.129 g (yield: 4.8%) of the complex (4) as a bronzed solid.

Its $^1$H-NMR ($C_6D_6$, δ (ppm)) showed the results: 1.06 to 1.13 (m, 6H), 1.20 (s, 18H), 1.29 to 1.51 (m, 4H), 1.37 (s, 9H), 2.26 (s, 3), 7.21 (s, 1H), 7.37 (s, 1H), 7.45 (d, J=9.0 Hz, 2H), 7.80 (s, 2H), and 8.00 (d, J=9.0 Hz, 2H).

Its mass spectrum (EI, m/z) showed 642 ($M^+$).

Example 7

Synthesis of diethylsilylene(2,7-di-tert-butylfluoren-9-yl)(3-tert-butyl-5-methyl-2-phenoxy)dimethyltitanium (Referred to as "Complex (5)" Hereinafter)

There was put 4 mL of a diethyl ether solution of diethylsilylene(2,7-di-tert-butylfluoren-9-yl)(3-tert-butyl-5-methyl-2-phenoxy)titanium dichloride in a Schlenk tube, 4 mL of said diethyl ether solution containing 248.7 mg (0.39 mmol) of said dichloride compound. To said Schlenk tube, 0.85 mmol of methyllithium was dropped at −78° C. using 0.74 mL of its diethyl ether solution having a concentration of 0.92 mol/L, and the temperature of the resultant mixture was raised up to a room temperature. Then, the mixture was stirred for 1 hour. The obtained mixture was concentrated, and the solid contained in the concentrated product was filtered off. The resultant solid was washed with pentane in order to remove impurities, and the solvent contained in the washed solid was distilled away under a reduced pressure. The obtained solid was dried, thereby obtaining 210.4 mg (yield: 90.3%) of the complex (5) as a yellow solid.

Its $^1$H-NMR (CDCl$_3$, δ (ppm)) showed the results: −0.35 (s, 6H), 0.75 to 0.84 (m, 4H), 0.90 to 1.00 (m, 6H), 1.11 (s, 18H), 1.28 (s, 9H), 2.29 (s, 3H), 7.05 (s, 1H), 7.09 (s, 1H), 7.20 (s, 2H), 7.40 (d, J=8.6 Hz, 2H), and 8.11 (d, J=8.6 Hz, 2H).

Example 8

Synthesis of diethylsilylene(2,7-di-tert-butylfluoren-9-yl)(3-tert-butyl-5-methyl-2-phenoxy)titanium diethoxide (Referred to as "Complex (6)" Hereinafter)

There was added at a room temperature 44.6 mg (0.39 mmol) of magnesium diethoxide to 4 mL of a THF solution of diethylsilylene(2,7-di-tert-butylfluoren-9-yl)(3-tert-butyl-5-methyl-2-phenoxy)titanium dichloride present in a Schlenk tube, 4 mL of said THF solution containing 248.7 mg (0.39 mmol) of said dichloride compound. The resultant mixture was stirred for 24 hours at a room temperature, and then the mixture was concentrated. Hexane was added to the concentrated mixture, and the obtained mixture was filtered in order to remove impurities. The filtrate was concentrated, and pentane was added thereto, thereby obtaining a precipitate. The precipitate was filtered off, and dried, thereby obtaining 180.1 mg (yield: 70.3%) of the complex (6) as a yellow solid.

Its $^1$H-NMR (CDCl$_3$, δ (ppm)) showed the results: 0.59 (t, J=7.6 Hz, 6H), 0.82 (t, J=6.9 Hz, 6H), 0.83 to 1.28 (m, 4H), 1.27 (s, 18H), 1.39 (s, 9H), 2.34 (s, 3H), 3.81 (q, J=6.9 Hz, 4H), 7.04 (s, 1H), 7.18 (s, 1H), 7.25 (d, J=8.2 Hz, 2H), 7.62 (s, 2H), and 7.80 (d, J=8.2 Hz, 2H).

Its mass spectrum (EI, m/z) showed 663 (M$^+$), 634, 590, 278, 263 and 221.

Example 9

Synthesis of diethylsilylene(2,7-di-tert-butylfluoren-9-yl)(3-tert-butyl-5-methyl-2-phenoxy)titanium diphenoxide (Referred to as "Complex (7)" Hereinafter)

There was added dropwise 2.05 mmol of methylmagnesium chloride using 683.6 mL of its solution having a concentration of 3.00 mol/L to 12 mL of a THF solution of phenol present in a Schlenk tube, 12 mL of said THF solution containing 193.0 mg (2.05 mmol) of phenol, and the resultant mixture was stirred for 3 hours at a room temperature. To the mixture, 3 mL of a THF solution of diethylsilylene(2,7-di-tert-butylfluoren-9-yl)(3-tert-butyl-5-methyl-2-phenoxy)titanium dichloride was added dropwise at −20° C., 3 mL of said THF solution containing 600.0 mg (0.93 mmol) of said dichloride compound. The obtained mixture was stirred for 20 hours at a room temperature. The mixture was concentrated, and pentane was added to the concentrated mixture. The obtained mixture was filtered in order to remove impurities. The filtrate was concentrated, and pentane was added thereto, thereby obtaining a precipitate. The precipitate was filtered off, and dried, thereby obtaining 599.9 mg (yield: 84.5%) of the complex (7) as an orange solid.

Its $^1$H-NMR (CDCl$_3$, δ (ppm)) showed the results: 0.81 to 1.43 (m, 10H), 1.16 (s, 18H), 1.17 (s, 9H), 2.41 (s, 3H), 6.39 (d, J=9.9 Hz, 4H), 6.70 to 6.80 (m, 2H), 7.00 to 7.34 (m, 8H), 7.57 (s, 2H), and 7.71 (d, J=8.6 Hz, 2H).

Its mass spectrum (EI, m/z) showed 758 (M$^+$).

Example 10

Synthesis of (2-allyloxy-3-tert-butyl-5-methylphenyl)chloroethylmethylsilane

There was obtained (2-allyloxy-3-tert-butyl-5-methylphenyl)chloroethylmethylsilane using dichloroethylmethylsilane according to a method similar to that of Example 1.

Synthesis of (2-allyloxy-3-tert-butyl-5-methylphenyl)(2,7-di-tert-butylfluoren-9-yl)ethylmethylsilane There was dissolved 2.00 g (7.18 mmol) of 2,7-di-tert-butylfluorene in 45 mL of THF, and the obtained solution was cooled down to −78° C. To the solution, 4.49 mL of a 1.60 M-concentration hexane solution of n-butyllithium was added slowly, 4.49 mL of said hexane solution containing 7.18 mmol of n-butyllithium. Temperature of the resultant mixture was raised up to a room temperature, and the mixture was stirred for 3 hours at a room temperature. The mixture was cooled down to −78° C., and a solution of 2.23 g (7.18 mmol) of (2-allyloxy-3-tert-butyl-5-methyl phenyl)chloroethylmethylsilane in 9 mL of toluene was added to the mixture. Temperature of the resultant mixture was raised up to a room temperature, and the mixture was stirred for 3 hours, thereby obtaining a reaction solution. A mixture of 20 mL of a 10% aqueous solution of sodium hydrogen carbonate and 20 mL of a 10% aqueous solution of sodium carbonate was added to the reaction solution at 0° C. To the obtained mixture, 23 mL of toluene was added, and the mixture was separated to the toluene solution and the aqueous solution. The toluene solution was dried over sodium sulfate, and the mixture was filtered. The obtained filtrate was concentrated under a reduced pressure, thereby obtaining quantitatively (2-allyloxy-3-tert-butyl-5-methylphenyl)(2,7-di-tert-butyl fluoren-9-yl)ethylmethylsilane.

Its $^1$H-NMR (CDCl$_3$, δ (ppm)) showed the results: −0.14 (s, 3H), 0.70 (t, J=7.3 Hz, 3H), 1.18 to 1.38 (m, 2H), 1.21 (s, 9H), 1.27 (s, 9H), 1.44 (s, 9H), 2.28 (s, 3H), 4.39 to 4.43 (m, 3H), 5.32 (d, J=10.9 Hz, 1H), 5.59 (d, 17.2 Hz, 1H), 6.03 to 6.15 (m, 1H), 6.95 (s, 1H), 7.00 (s, 1H), 7.13 to 7.32 (m, 4H), and 7.67 (dd, J=3.0 Hz and 7.9 Hz, 2H).

Its mass spectrum (ED, m/z) showed 552 (M$^+$).

Example 11

Synthesis of ethylmethylsilylene(2,7-di-tert-butylfluoren-9-yl)(3-tert-butyl-5-methyl-2-phenoxy)titanium dichloride (Referred to as "Complex (8)" Hereinafter)

There was dissolved 3.97 g (7.18 mmol) of (2-allyloxy-3-tert-butyl-5-methylphenyl)(2,7-di-tert-butylfluoren-9-yl)ethylmethylsilane in 80 mL of heptane, and 3.05 g (30.14 mmol) of triethylamine was added thereto. Temperature of the obtained mixture was cooled down to −78° C., and 9.42 mL of a 1.60 M-concentration hexane solution of n-butyllithium was added dropwise to the mixture, 9.42 mL of said hexane solution containing 15.07 mmol of n-butyllithium.

Temperature of the resultant mixture was raised up to a room temperature, and the mixture was stirred for 3 hours at a room temperature. The mixture was cooled down to −78° C., and a solution of 1.50 g (7.89 mmol) of titanium tetrachloride in 8 mL of heptane was dropped to the mixture. Temperature of the resultant mixture was raised up to a room temperature, and the mixture was stirred for 2 hours at 60° C. The obtained mixture was filtered with celite under a nitrogen atmosphere to remove impurities, and the filtrate was concentrated. The concentrated product was recrystallized from pentane, thereby obtaining 0.66 g (yield: 14.6%) of the complex (8) as a brown solid.

Its $^1$H-NMR (CDCl$_3$, δ (ppm)) showed the results: 0.80 (s, 3H), 0.86 to 1.45 (m, 5H), 1.18 (s, 9H), 1.21 (s, 9H), 1.29 (s, 9H), 2.43 (s, 3H), 7.16 (s, 1H), 7.32 (s, 1H), 7.50 (s, 1H), 7.61 to 7.69 (m, 3H), and 8.19 (dd, J=5.3 Hz and 8.9 Hz, 2H).

Its mass spectrum (EI, m/z) showed 628 (M$^+$) and 599.

Example 12

Synthesis of (2-allyloxy-3-tert-butyl-5-methylphenyl)chloromethylphenylsilane

There was obtained (2-allyloxy-3-tert-butyl-5-methylphenyl)chloromethylphenylsilane using dichloromethylphenylsilane according to a method similar to that of Example 1.

Synthesis of (2-allyloxy-3-tert-butyl-5-methylphenyl)(2,7-di-tert-butylfluoren-9-yl)methylphenylsilane There was dissolved 3.51 g (12.61 mmol) of 2,7-di-tert-butylfluorene in 79 mL of THF, and the obtained solution was cooled down to −78° C. To the solution, 8.19 mL of a 1.54 M-concentration hexane solution of n-butyllithium was added slowly, 8.19 mL of said hexane solution containing 12.61 mmol of n-butyllithium. Temperature of the resultant mixture was raised up to a room temperature, and the mixture was stirred for 3 hours at a room temperature. The mixture was cooled down to −78° C., and a solution of 4.53 g (12.61 mmol) of (2-allyloxy-3-tert-butyl-5-methyl phenyl)chloromethylphenylsilane in 16 mL of toluene was added to the mixture. Temperature of the resultant mixture was raised up to a room temperature, and the mixture was stirred for 3.5 hours, thereby obtaining a reaction solution. A mixture of 35 mL of a 10% aqueous solution of sodium hydrogen carbonate and 35 mL of a 10% aqueous solution of sodium carbonate was added to the reaction solution at 0° C. To the obtained mixture, 41 mL of toluene was added, and the mixture was separated to the toluene solution and the aqueous solution. The toluene solution was dried over sodium sulfate, and the mixture was filtered. The obtained filtrate was concentrated under a reduced pressure, thereby obtaining quantitatively (2-allyloxy-3-tert-butyl-5-methylphenyl)(2,7-di-tert-butyl fluoren-9-yl)methylphenylsilane.

Its $^1$H-NMR (CDCl$_3$, δ (ppm)) showed the results: −0.13 (s, 3H), 1.13 (s, 9H), 1.15 (s, 9H), 1.40 (s, 9H), 2.49 (s, 3H), 3.91 to 3.99 (m, 1H), 4.03 to 4.15 (m, 1H), 4.52 (s, 1H), 5.11 (d, J=10.9 Hz, 1H), 5.25 (d, J=17.2 Hz, 1H), 5.71 to 5.85 (m, 1H), 6.69 (s, 1H), 6.92 (s, 1H), and 7.27 to 7.78 (m, 11H).

Its mass spectrum (FD, m/z) showed 600 (M$^+$) and 454.

Example 13

Synthesis of methylphenylsilylene(2,7-di-tert-butylfluoren-9-yl)(3-tert-butyl-5-methyl-2-phenoxy) titanium dichloride (Referred to as "Complex (9)" Hereinafter)

There was dissolved 3.00 g (4.99 mmol) of (2-allyloxy-3-tert-butyl-5-methylphenyl)(2,7-di-tert-butylfluoren-9-yl) methylphenylsilane in 54 mL of heptane, and 2.27 g (22.46 mmol) of triethylamine was added thereto. Temperature of the obtained mixture was cooled down to −78° C., and 7.29 mL of a 1.54 M-concentration hexane solution of n-butyllithium was added dropwise to the mixture, 7.29 mL of said hexane solution containing 11.23 mmol of n-butyllithium. Temperature of the resultant mixture was raised up to a room temperature, and the mixture was stirred for 3 hours at a room temperature. The mixture was cooled down to −78° C., and a solution of 1.42 g (7.49 mmol) of titanium tetrachloride in 8 mL of heptane was dropped to the mixture. Temperature of the resultant mixture was raised up to a room temperature, and the mixture was stirred for 3 hours at 90° C. The obtained mixture was filtered with celite under a nitrogen atmosphere to remove impurities, and the filtrate was concentrated. Pentane was added to the concentrated filtrate, and the mixture was allowed to stand at −20° C., thereby obtaining 0.35 g (yield: 10.5%) of the complex (9) as a brown solid.

Its $^1$H-NMR (CDCl$_3$, δ (ppm)) showed the results: 1.04 (s, 9H), 1.12 (s, 3H), 1.23 (s, 9H), 1.25 (s, 9H), 2.35 (s, 3H), 6.96 (s, 1H), 7.19 to 7.26 (m, 3H), 7.46 to 7.66 (m, 5H), 7.69 to 7.79 (m, 2H), and 8.12 to 8.18 (m, 2H).

Its mass spectrum (EI, m/z) showed 676 (M$^+$) and 625.

Example 14

Synthesis of (2-allyloxy-3-tert-butyl-5-methylphenyl)chlorodi-n-propylsilane

There was obtained (2-allyloxy-3-tert-butyl-5-methylphenyl)chlorodi-n-propylsilane using dichlorodi-n-propylsilane according to a method similar to that of Example 1.

Synthesis of (2-allyloxy-3-tert-butyl-5-methylphenyl)(2,7-di-tert-butylfluoren-9-yl)di-n-propylsilane There was dissolved 2.28 g (8.19 mmol) of 2,7-di-tert-butylfluorene in 37 mL of THF, and the obtained solution was cooled down to 0° C. To the solution, 5.19 mL of a 1.58 M-concentration hexane solution of n-butyllithium was added slowly, 5.19 mL of said hexane solution containing 8.20 mmol of n-butyllithium. Temperature of the resultant mixture was raised up to a room temperature, and the mixture was stirred for 1 hour at a room temperature. The mixture was cooled down to 0° C., and a solution of 2.89 g (8.17 mmol) of (2-allyloxy-3-tert-butyl-5-methyl phenyl)chlorodi-n-propylsilane in 9 mL of THF was added to the mixture. Temperature of the resultant mixture was raised up to a room temperature, and the mixture was stirred for 3 hours, thereby obtaining a reaction solution. A mixture of 50 mL of a 10% aqueous solution of sodium hydrogen carbonate and 50 mL of a 10% aqueous solution of sodium carbonate was added to the reaction solution at 0° C. To the obtained mixture, 58 mL of toluene was added, and the mixture was separated to the toluene solution and the aqueous solution. The toluene solution was dried over sodium sulfate, and the mixture was filtered. The obtained filtrate was concentrated under a reduced pressure. The concentrated filtrate was treated according to silica gel-column chromatography using, as a developing solvent, a 0.5% concentration-solution of triethylamine in a mixed solvent of 10 parts by volume of hexane and 1 part by volume of ethyl acetate, thereby obtaining 1.01 g (yield: 20.7%) of (2-allyloxy-3-tert-butyl-5-methylphenyl) (2,7-di-tert-butylfluoren-9-yl)di-n-propylsilane.

Its $^1$H-NMR (CDCl$_3$, δ (ppm)) showed the results: 0.48 to 1.01 (m, 14H), 1.25 (s, 18H), 1.41 (s, 9H), 2.28 (s, 3H), 4.35 (br s, 2H), 4.43 (s, 1H), 5.30 (d, J=10.9 Hz, 1H), 5.55 (d, J=17.5 Hz, 1H), 5.97 to 6.11 (m, 1H), 6.96 (s, 1H), 7.12 (s, 2H), 7.25 (s, 1H), 7.28 (d, J=7.9 Hz, 2H), and 7.66 (d, J=7.9 Hz, 2H).

Its mass spectrum (FD, m/z) showed 594 (M+).

Example 15

Synthesis of di-n-propylsilylene(2,7-di-tert-butylfluoren-9-yl)(3-tert-butyl-5-methyl-2-phenoxy) titanium dichloride (Referred to as "Complex (10)" Hereinafter)

There was dissolved 1.01 g (1.70 mmol) of (2-allyloxy-3-tert-butyl-5-methylphenyl)(2,7-di-tert-butylfluoren-9-yl)di-n-propylsilane in 17 mL of heptane, and 0.77 g (7.65 mmol) of triethylamine was added thereto. Temperature of the obtained mixture was cooled down to −78° C., and 2.41 mL of a 1.59 M-concentration hexane solution of n-butyllithium was added dropwise to the mixture, 2.41 mL of said hexane solution containing 3.83 mmol of n-butyllithium. Temperature of the resultant mixture was raised up to a room temperature, and the mixture was stirred for 3.5 hours at a room temperature. The mixture was cooled down to −78° C., and a solution of 0.43 g (2.25 mmol) of titanium tetrachloride in 5 mL of heptane was dropped to the mixture. Temperature of the resultant mixture was raised up to a room temperature, and the mixture was stirred for 3 hours at 90° C. The obtained mixture was filtered with celite under a nitrogen atmosphere to remove impurities, and the filtrate was concentrated. Pentane was added to the concentrated filtrate, thereby obtaining 0.09 g (yield: 8.15%) of the complex (10) as a red-brown solid.

Its $^1$H-NMR (CDCl$_3$, δ (ppm)) showed the results: 0.99 (t, J=7.3 Hz, 6H), 1.18 (s, 9H), 1.07 to 1.59 (m, 8H), 1.25 (s, 18H), 2.43 (s, 3H), 7.15 (s, 1H), 7.28 (s, 1H), 7.55 (s, 2H), 7.65 (d, J=8.9 Hz, 2H), and 8.18 (d, J=8.9 Hz, 2H).

Its mass spectrum (EI, m/z) showed 670 (M+).

Example 16

Synthesis of 2,7-diphenyfluorene

There were mixed 10.00 g (30.86 mmol) of 2,7-dibromofluorene, 15.05 g (123.45 mmol) of phenylboronic acid, 29.21 g (92.59 mmol) of barium hydroxide (Ba(OH)$_2$.8H$_2$O) and 0.71 g (0.62 mmol) of tetrakis(priphenylphosphine) palladium in an atmosphere of nitrogen. To the mixture, 200 mL of 1,4-dioxane and 33 mL of water were added at a room temperature. Temperature of the resultant mixture was raised up to 80° C., and the mixture was heated at 80° C. for 6 hours. Temperature of the mixture was cooled down to a room temperature, and 200 mL of toluene and 100 mL of a saturated solution of sodium chloride were added to the mixture. The obtained mixture was filtered, thereby obtaining a white solid. There was extracted 2,7-diphenyfluorene from the white solid with each 400 mL of hot THF three times. THF contained in the extract was distilled away, and the resultant solid was dried under a reduced pressure, thereby obtaining 7.94 g (yield: 80%) of 2,7-diphenyfluorene as a white solid.

Its $^1$H-NMR (CDCl$_3$, δ (ppm)) showed the results: 4.03 (s, 2H), 7.36 (t, J=7.3 Hz, 2H), 7.47 (t, J=7.8 Hz, 4H), 7.62 to 7.69 (m, 6H), 7.80 (s, 2H), and 7.87 (d, J=7.8 Hz, 2H).

Synthesis of (2-allyloxy-3-tert-butyl-5-methylphenyl)chlorodiethylsilane

There was obtained (2-allyloxy-3-tert-butyl-5-methylphenyl)chlorodiethylsilane using dichlorodiethylsilane according to a method similar to that of Example 1.

Synthesis of (2-allyloxy-3-tert-butyl-5-methylphenyl)(2,7-diphenylfluoren-9-yl)diethylsilane There was dissolved 3.00 g (9.42 mmol) of 2,7-diphenylfluorene in 60 mL of THF, and the obtained solution was cooled down to −78° C. To the solution, 6.12 mL of a 1.54 M-concentration hexane solution of n-butyllithium was added slowly, 6.12 mL of said hexane solution containing 9.42 mmol of n-butyllithium. Temperature of the resultant mixture was raised up to a room temperature, and the mixture was stirred for 2 hours at a room temperature. The mixture was cooled down to −78° C., and a solution of 3.06 g (9.42 mmol) of (2-allyloxy-3-tert-butyl-5-methylphenyl)chlorodiethylsilane in 14 mL of toluene was added to the mixture. Temperature of the resultant mixture was raised up to a room temperature, and the mixture was stirred for 3 hours, thereby obtaining a reaction solution. A mixture of 50 mL of a 10% aqueous solution of sodium hydrogen carbonate and 50 mL of a 10% aqueous solution of sodium carbonate was added to the reaction solution at 0° C. To the obtained mixture, 58 mL of toluene was added, and the mixture was separated to the toluene solution and the aqueous solution. The toluene solution was dried over sodium sulfate, and the mixture was filtered. The obtained filtrate was concentrated under a reduced pressure. A small amount of toluene was added the concentrated filtrate to obtain a solution, and hexane was further added thereto, thereby obtaining 3.66 g (yield: 64.0%) of (2-allyloxy-3-tert-butyl-5-methylphenyl)(2,7-diphenyl fluoren-9-yl)diethylsilane as a white solid.

Its $^1$H-NMR (CDCl$_3$, δ (ppm)) showed the results: 0.61 to 0.95 (m, 10H), 1.39 (s, 9H), 2.27 (s, 3H), 4.42 (br s, 2H), 4.64 (s, 1H), 5.27 (d, J=10.6 Hz, 1H), 5.56 (d, J=17.2 Hz, 1H), 5.98 to 6.12 (m, 1H), 6.98 (s, 1H), 7.29 to 7.65 (m, 15H), and 7.87 (d, J=7.9 Hz, 2H).

Its mass spectrum (EI, m/z) showed 606 (M+), 317, 289, 261 and 233.

Example 17

Synthesis of diethylsilylene(2,7-diphenylfluoren-9-yl)(3-tert-butyl-5-methyl-2-phenoxy)titanium dichloride (Referred To as "Complex (11)" Hereinafter)

There was suspended 1.50 g (2.47 mmol) of (2-allyloxy-3-tert-butyl-5-methylphenyl)(2,7-diphenylfluoren-9-yl)diethylsilane in 24 mL of heptane, and 1.13 g (11.12 mmol) of triethylamine was added thereto. Temperature of the obtained mixture was cooled down to −78° C., and 3.61 mL of a 1.54 M-concentration hexane solution of n-butyllithium was added dropwise to the mixture, 3.61 mL of said hexane solution containing 5.56 mmol of n-butyllithium. Temperature of the resultant mixture was raised up to a room temperature, and the mixture was stirred for 4 hours at a room temperature. The mixture was cooled down to −78° C., and a solution of 0.70 g (3.71 mmol) of titanium tetrachloride in 4 mL of heptane was dropped to the mixture. Temperature of the resultant mixture was raised up to a room temperature, and the mixture was stirred for 3 hours at 90° C. The obtained mixture was filtered with celite under a nitrogen atmosphere to remove impurities, and the filtrate was concentrated. Pentane was added to the concentrated filtrate, thereby obtaining 0.05 g (yield: 2.8%) of the complex (11) as a brown solid.

Its $^1$H-NMR (CDCl$_3$, δ (ppm)) showed the results: 0.86 to 1.56 (m, 10H), 1.16 (s, 9H), 2.46 (s, 3H), 7.23 to 7.47 (m, 12H), 7.81 to 7.86 (m, 4H), and 8.39 (d, J=8.6 Hz, 2H).

Its mass spectrum (EI, m/z) showed 683 (M$^+$).

Example 18

Synthesis of (2-allyloxy-3-tert-butyl-5-methylphenyl)chlorodiethylsilane

There was obtained (2-allyloxy-3-tert-butyl-5-methylphenyl)chlorodiethylsilane using dichlorodiethylsilane according to a method similar to that of Example 1.

Synthesis of (2-allyloxy-3-tert-butyl-5-methylphenyl)(3,6-di-tert-butylfluoren-9-yl)diethylsilane There was washed 1.50 g (11.22 mmol) of potassium hydride having a purity of 30% by weight with each 3 mL of hexane three times in an atmosphere of nitrogen, and 18 mL of THF was added thereto. To the obtained THF slurry of potassium hydride, 2.50 g (8.98 mml) of 3,6-di-tert-butylfluorene was added dropwise at 0° C. using 18 mL of a THF solution thereof. The obtained mixture was stirred for 2 hours at a room temperature, and then 2.92 g (8.98 mmol) of (2-allyloxy-3-tert-butyl-5-methylphenyl)chlorodiethylsilane was added dropwise at −78° C. using 4 mL of a toluene solution thereof. The temperature of the obtained liquid reaction mixture was raised up to a room temperature, and the mixture was stirred for 2 hours. The mixture was added dropwise at 0° C. to a mixture of 18 mL of a 10% aqueous solution of sodium hydrogen carbonate and 18 mL of a 10% aqueous solution of sodium carbonate, and the resultant mixture was extracted with 10 mL of toluene. The obtained extract was dried over sodium sulfate, and dried extract was concentrated under a reduced pressure, thereby obtaining quantitatively (2-allyloxy-3-tert-butyl-5-methylphenyl)(3,6-di-tert-butylfluoren-9-yl)diethylsilane.

Its $^1$H-NMR (CDCl$_3$, δ (ppm)) showed the results: 0.60 to 1.11 (m, 10H), 1.39 (s, 18H), 1.41 (s, 9H), 2.35 (s, 3H), 4.18 to 4.21 (m, 2H), 4.32 (s, 1H), 5.15 to 5.20 (m, 1H), 5.40 to 5.50 (m, 1H), 5.85 to 6.09 (m, 1H), 6.80 (s, 1H), 7.15 to 7.28 (m, 5H), and 7.81 (s, 2H).

Example 19

Synthesis of diethylsilylene(3,6-di-tert-butylfluoren-9-yl)(3-tert-butyl-5-methyl-2-phenoxy)titanium dichloride (Referred to as "Complex (12)" Hereinafter)

There was added dropwise at −78° C. 20.20 mmol of n-butyllithium using 12.87 mL of its hexane solution having a concentration of 1.57 mol/L to 97 mL of a toluene solution containing 5.09 g (8.98 mmol) of (2-allyloxy-3-tert-butyl-5-methylphenyl)(3,6-di-tert-butylfluoren-9-yl)diethylsilane and 4.09 g (40.41 mmol) of triethylamine, and the resultant mixture was stirred for 10 minutes, and then for 3 hours at a room temperature. To the obtained reaction mixture solution, 2.56 g (13.47 mmol) of titanium tetrachloride was added dropwise at −78° C. using 13 mL of its toluene solution, and the temperature of the resultant mixture was raised up to a room temperature, and then the mixture was stirred at 90° C. for 3 hours. The obtained mixture was cooled, and then was concentrated. The resultant solid was washed with hexane in order to remove impurities, and the solvent contained in the washed solid was distilled away under a reduced pressure, thereby obtaining the solid. The solid was washed with pentane, thereby obtaining 0.366 g (yield: 6.3%) of the complex (12) as a brown solid.

Its $^1$H-NMR (CDCl$_3$, δ (ppm)) showed the results: 1.00 to 1.10 (m, 6H), 1.16 (s, 9H), 1.26 to 1.45 (m, 4H), 1.45 (s, 18H), 2.43 (s, 3H), 7.17 (s, 1H), 7.26 (s, 1H), 7.50 to 7.60 (m, 4H), and 8.12 (s, 2H).

Its mass spectrum (EI, m/z) showed 642 (M$^+$).

Example 20

Synthesis of 6,6,9,9-tetramethyl-6,7,8,9-tetrahydrobenzofluorene

There was obtained 6,6,9,9-tetramethyl-6,7,8,9-tetrahydrobenzofluorene according to a method similar to that disclosed in Organometallics, 23, 1777 (2004).

Synthesis of (2-allyloxy-3-tert-butyl-5-methylphenyl)chlorodiethylsilane

There was obtained (2-allyloxy-3-tert-butyl-5-methylphenyl)chlorodiethylsilane using dichlorodiethylsilane according to a method similar to that of Example 1.

Synthesis of (2-allyloxy-3-tert-butyl-5-methylphenyl)(6,6,9,9-tetramethyl-6,7,8,9-tetrahydrobenzofluoren-11-yl)diethylsilane There was dissolved 2.50 g (8.98 mmol) of 6,6,9,9-tetramethyl-6,7,8,9-tetrahydrobenzofluorene in 56 mL of THF, and the obtained solution was cooled down to −78° C. To the solution, 5.68 mL of a 1.58 M-concentration hexane solution of n-butyllithium was added slowly, 5.68 mL of said hexane solution containing 8.98 mmol of n-butyllithium. Temperature of the resultant mixture was raised up to a room temperature, and the mixture was stirred for 3.5 hours at a room temperature. The mixture was cooled down to −78° C., and a solution of 2.92 g (8.98 mmol) of (2-allyloxy-3-tert-butyl-5-methylphenyl) chlorodiethylsilane in 12 mL of toluene was added to the mixture. Temperature of the resultant mixture was raised up to a room temperature, and the mixture was stirred for 3 hours, thereby obtaining a reaction solution. A mixture of 25 mL of a 10% aqueous solution of sodium hydrogen carbonate and 25 mL of a 10% aqueous solution of sodium carbonate was added to the reaction solution at 0° C. To the obtained mixture, 29 mL of toluene was added, and the mixture was separated to the toluene solution and the aqueous solution. The toluene solution was dried over sodium sulfate, and the mixture was filtered. The obtained filtrate was concentrated under a reduced pressure, thereby obtaining quantitatively (2-allyloxy-3-tert-butyl-5-methylphenyl)(6,6,9,9-tetramethyl-6,7,8,9-tetrahydrobenzofluoren-11-yl) diethylsilane.

Its $^1$H-NMR (CDCl$_3$, δ (ppm)) showed the results: 0.41 to 0.50 (m, 6H), 0.68 to 0.78 (m, 4H), 1.06 (s, 3H), 1.15 (s, 3H), 1.31 to 1.39 (m, 4H), 1.33 (s, 3H), 1.34 (s, 3H), 1.42 (s, 9H), 2.28 (s, 3H), 4.31 to 4.41 (m, 2H), 4.43 (s, 1H), 5.26 (d, J=10.9 Hz, 1H), 5.52 (d, J=17.2 Hz, 1H), 5.92 to 6.12 (m, 1H), 6.90 (s, 1H), 6.94 (br s, 1H), 7.14 to 7.29 (m, 4H), 7.71 (s, 1H), and 7.77 (d, J=7.3 Hz, 1H).

Its mass spectrum (FD, m/z) showed 564 (M$^+$).

Example 21

Synthesis of diethylsilylene(6,6,9,9-tetramethyl-6,7,8,9-tetrahydrobenzofluoren-11-yl)(3-tert-butyl-5-methyl-2-phenoxy)titanium dichloride (Referred to as "Complex (13)" Hereinafter)

There was dissolved 2.46 g (4.35 mmol) of (2-allyloxy-3-tert-butyl-5-methylphenyl)(6,6,9,9-tetramethyl-6,7,8,9-tetrahydrobenzofluoren-11-yl)diethylsilane in 45 mL of heptane, and 1.98 g (19.58 mmol) of triethylamine was added thereto. Temperature of the obtained mixture was cooled down to −78° C., and 6.19 mL of a 1.58 M-concentration hexane solution of n-butyllithium was added dropwise to the mixture, 6.19 mL of said hexane solution containing 9.79 mmol of n-butyllithium. Temperature of the resultant mixture was raised up to a room temperature, and the mixture was stirred for 1.5 hour at a room temperature. The mixture was cooled down to −78° C., and a solution of 1.24 g (4.46 mmol) of titanium tetrachloride in 5 mL of heptane was dropped to the mixture. Temperature of the resultant mixture was raised up to a room temperature, and the mixture was stirred for 2 hours at 60° C. The obtained mixture was filtered with celite under a nitrogen atmosphere to remove impurities, and the filtrate was concentrated. Pentane was added to the concentrated filtrate, and the mixture was allowed to stand at −20° C., thereby obtaining 0.12 g (yield: 4.3%) of the complex (13) as a brown solid.

Its $^1$H-NMR (CDCl$_3$, δ (ppm)) showed the results: 0.86 to 1.11 (m, 10H), 1.04 (s, 3H), 1.19 (s, 9H), 1.24 (s, 3H), 1.44 (s, 3H), 1.47 (s, 3H), 1.67 to 1.79 (m, 4H), 2.43 (s, 3H), 7.16 (s, 1H), 7.28 (s, 1H), 7.44 to 7.50 (m, 1H), 7.55 to 7.60 (m, 2H), 7.64 (d, J=8.5 Hz, 1H), 8.02 (s, 1H), and 8.28 (d, J=8.5 Hz, 1H).

Its mass spectrum (EI, m/z) showed 640 (M$^+$) and 611.

Example 22

Synthesis of 6,6,9,9-tetramethyl-6,7,8,9-tetrahydrobenzofluorene

There was obtained 6,6,9,9-tetramethyl-6,7,8,9-tetrahydrobenzofluorene according to a method similar to that disclosed in Organometallics, 23, 1777 (2004).

Synthesis of (2-allyloxy-3-tert-butyl-5-methylphenyl)chloromethylphenylsilane

There was obtained (2-allyloxy-3-tert-butyl-5-methylphenyl)chloromethylphenylsilane using dichloromethylphenylsilane according to a method similar to that of Example 1.

Synthesis of (2-allyloxy-3-tert-butyl-5-methylphenyl)(6,6,9,9-tetramethyl-6,7,8,9-tetrahydrobenzofluoren-11-yl)methylphenylsilane There was dissolved 5.00 g (18.09 mmol) of 6,6,9,9-tetramethyl-6,7,8,9-tetrahydrobenzofluorene in 112 mL of THF, and the obtained solution was cooled down to −78° C. To the solution, 11.31 mL of a 1.60 M-concentration hexane solution of n-butyllithium was added slowly, 11.31 mL of said hexane solution containing 18.09 mmol of n-butyllithium. Temperature of the resultant mixture was raised up to a room temperature, and the mixture was stirred for 2 hours at a room temperature. The mixture was cooled down to −78° C., and a solution of 6.49 g (18.09 mmol) of (2-allyloxy-3-tert-butyl-5-methylphenyl)chloromethylphenylsilane in 23 mL of toluene was added to the mixture. Temperature of the resultant mixture was raised up to a room temperature, and the mixture was stirred for 4 hours, thereby obtaining a reaction solution. A mixture of 50 mL of a 10% aqueous solution of sodium hydrogen carbonate and 50 mL of a 10% aqueous solution of sodium carbonate was added to the reaction solution at 0° C. To the obtained mixture, 58 mL of toluene was added, and the mixture was separated to the toluene solution and the aqueous solution. The toluene solution was dried over sodium sulfate, and the mixture was filtered. The obtained filtrate was concentrated under a reduced pressure, thereby obtaining quantitatively a mixture of two kinds of isomers of (2-allyloxy-3-tert-butyl-5-methylphenyl) (6,6,9,9-tetramethyl-6,7,8,9-tetrahydrobenzofluoren-11-yl)methylphenylsilane.

Its $^1$H-NMR (CDCl$_3$, δ (ppm)) showed the results: 0.23 (s, 3H), 0.71 (s, 3H), 0.80 to 1.00 (m, 6H), 1.10 to 1.23 (m, 6H), 1.32 to 1.55 (m, 30H), 1.61 to 1.85 (m, 8H), 2.40 to 2.50 (m, 6H), 3.90 to 4.00 (m, 2H), 4.10 to 4.32 (m, 2H), 4.52 to 4.58 (m, 2H), 5.10 to 5.50 (m, 4H), 5.77 to 6.06 (m, 2H), 6.71 to 6.81 (m, 2H), 6.93 to 7.12 (m, 2H), and 7.20 to 7.85 (m, 22H).

Its mass spectrum (FD, m/z) showed 598 (M$^+$).

Example 23

Synthesis of methylphenylsilylene(6,6,9,9-tetramethyl-6,7,8,9-tetrahydrobenzofluoren-11-yl)(3-tert-butyl-5-methyl-2-phenoxy)titanium dichloride (Referred to as "Complex (14)" Hereinafter)

There was dissolved 6.97 g (11.65 mmol) of (2-allyloxy-3-tert-butyl-5-methylphenyl)(6,6,9,9-tetramethyl-6,7,8,9-tetrahydrobenzofluoren-11-yl)methylphenylsilane in 129 mL of heptane, and 5.30 g (52.40 mmol) of triethylamine was added thereto. Temperature of the obtained mixture was cooled down to −78° C., and 16.38 mL of a 1.60 M-concentration hexane solution of n-butyllithium was added dropwise to the mixture, 16.38 mL of said hexane solution containing 26.20 mmol of n-butyllithium. Temperature of the resultant mixture was raised up to a room temperature, and the mixture was stirred for 3 hours at a room temperature. The solvent contained in the resultant reaction mixture was distilled away under a reduced pressure, thereby obtaining 10.08 g of a yellow solid as a dilithium product. There was added 39 mL of heptane to 3.00 g of the yellow solid, and the mixture was cooled down to −78° C., and a solution of 0.66 g (3.47 mmol) of titanium tetrachloride in 4 mL of heptane was dropped to the mixture. Temperature of the resultant mixture was raised up to a room temperature, and the mixture was stirred for 2 hours at 60° C. The obtained mixture was filtered with celite under a nitrogen atmosphere to remove impurities, and the filtrate was concentrated, thereby obtaining a mixture of isomers of diethylsilylene(6,6,9,9-tetramethyl-6,7,8,9-tetrahydrobenzofluoren-11-yl)(3-tert-butyl-5-methyl-2-phenoxy) titanium dichloride.

Its mass spectrum (EI, m/z) showed 674 (M$^+$).

Example 24

Synthesis of 2-tert-butyl-6,6,9,9-tetramethyl-6,7,8,9-tetrahydrobenzofluorene

Synthesis of 6,6,9,9-tetramethyl-6,7,8,9-tetrahydrobenzofluorene

There was obtained 6,6,9,9-tetramethyl-6,7,8,9-tetrahydrobenzofluorene according to a method similar to that disclosed in Organometallics, 23, 1777 (2004).

There were added 6.92 g (25.05 mmol) of 6,6,9,9-tetramethyl-6,7,8,9-tetrahydrobenzofluorene and 11.04 g (50.09 mmol) of 2,6-di-tert-butylcresol to 123 mL of nitromethane, and the resultant mixture was stirred at 0° C., thereby obtaining a slurry. To the slurry, 7.5 mL of a solution of 5.01 g (37.57 mmol) of aluminum chloride in nitromethane was added dropwise at 0° C., and the mixture was stirred at 0° C. for 1.5 hour. The formed precipitate was filtered off, and the filtrate was subjected to extraction with each 42 mL of hexane seven times. The obtained hexane solution was dried over magnesium sulfate, and the dried solution was filtered to obtain a filtrate, and then, the filtrated was concentrated. The concentrated filtrate was treated according to silica gel-column chromatography to obtain yellow oil. Ethanol was added to the oil to form a precipitate, and the precipitate was filter off. The precipitate was vacuum-dried, thereby obtaining 2.89 g (yield: 34.7%) of 2-tert-butyl-6,6,9,9-tetramethyl-6,7,8,9-tetrahydrobenzofluorene as a white solid.

Its $^1$H-NMR (CDCl$_3$, δ (ppm)) showed the results: 1.32 (s, 9H), 1.36 (s, 12H), 1.72 (s, 4H), 3.81 (s, 2H), 7.36 (d, J=7.9 Hz, 1H), 7.46 (s, 1H), 7.51 (s, 1H), 7.65 (d, J=7.9 Hz, 1H), and 7.67 (s, 1H).

Its $^{13}$C-NMR (CDCl$_3$, δ (ppm)) showed the results: 31.04, 31.62, 32.14, 32.25, 33.00, 34.50, 34.54, 34.77, 35.28, 36.64, 117.27, 118.94, 121.81, 122.80, 123.65, 139.20, 139.36, 140.63, 143.14, 143.36 and 149.38.

Its mass spectrum (EI, m/z) showed 332 (M$^+$) and 317.

Synthesis of (2-allyloxy-3-tert-butyl-5-methylphenyl)chlorodiethylsilane

There was obtained (2-allyloxy-3-tert-butyl-5-methylphenyl)chlorodiethylsilane using dichlorodiethylsilane according to a method similar to that of Example 1.

Synthesis of (2-allyloxy-3-tert-butyl-5-methylphenyl)(2-tert-butyl-6,6,9,9-tetramethyl-6,7,8,9-tetrahydrobenzofluoren-11-yl)diethylsilane There was dissolved 2.70 g (8.12 mmol) of 2r-tert-butyl-6,6,9,9-tetramethyl-6,7,8,9-tetrahydrobenzofluorene in 60 mL of THF, and the obtained solution was cooled down to −78° C. To the solution, 5.14 mL of a 1.58 M-concentration hexane solution of n-butyllithium was added slowly, 5.14 mL of said hexane solution containing 8.12 mmol of n-butyllithium. Temperature of the resultant mixture was raised up to a room temperature, and the mixture was stirred for 3 hours at a room temperature. The mixture was cooled down to −78° C., and a solution of 2.64 g (8.12 mmol) of (2-allyloxy-3-tert-butyl-5-methylphenyl)chlorodiethylsilane in 12 mL of toluene was added to the mixture. Temperature of the resultant mixture was raised up to a room temperature, and the mixture was stirred for 3 hours, thereby obtaining a reaction solution. A mixture of 27 mL of a 10% aqueous solution of sodium hydrogen carbonate and 27 mL of a 10% aqueous solution of sodium carbonate was added to the reaction solution at 0° C. To the obtained mixture, 31 mL of toluene was added, and the mixture was separated to the toluene solution and the aqueous solution. The toluene solution was dried over sodium sulfate, and the mixture was filtered. The obtained filtrate was concentrated under a reduced pressure, thereby obtaining quantitatively (2-allyloxy-3-tert-butyl-5-methylphenyl)(2-tert-butyl-6,6,9,9-tetramethyl-6,7,8,9-tetrahydrobenzofluoren-11-yl)diethylsilane.

Its $^1$H-NMR (CDCl$_3$, δ (ppm)) showed the results: 0.52 to 0.63 (m, 6H), 0.74 to 0.99 (m, 4H), 1.12 (s, 3H), 1.18 (s, 3H), 1.06 to 1.47 (m, 4H), 1.24 (s, 9H), 1.32 (s, 3H), 1.34 (s, 3H), 1.42 (s, 9H), 2.28 (s, 3H), 4.34 to 4.35 (m, 2H), 4.39 (s, 1H), 5.28 (d, J=10.9 Hz, 1H), 5.53 (d, J=17.5 Hz, 1H), 6.01 to 6.10 (m, 1H), 6.98 to 7.01 (m, 1H), 7.11 (s, 1H), 7.16 to 7.18 (m, 1H), 7.23 to 7.28 (m, 2H), 7.66 (s, 1H), and 7.66 (d, J=7.9 Hz, 1H).

Its mass spectrum (FD, m/z) showed 620 (M$^+$).

Example 25

Synthesis of diethylsilylene(2-tert-butyl-6,6,9,9-tetramethyl-6,7,8,9-tetrahydrobenzofluoren-11-yl)(3-tert-butyl-5-methyl-2-phenoxy)titanium dichloride (Referred to as "Complex (15)" Hereinafter)

There was dissolved 2.52 g (4.06 mmol) of (2-allyloxy-3-tert-butyl-5-methylphenyl)(2-tert-butyl-6,6,9,9-tetra methyl-6,7,8,9-tetrahydrobenzofluoren-11-yl)diethylsilane in 45 mL of heptane, and 1.72 g (17.04 mmol) of triethylamine was added thereto. Temperature of the obtained mixture was cooled down to −78° C., and 5.39 mL of a 1.58 M-concentration hexane solution of n-butyllithium was added dropwise to the mixture, 5.39 mL of said hexane solution containing 8.52 mmol of n-butyllithium. Temperature of the resultant mixture was raised up to a room temperature, and the mixture was stirred for 1.5 hour at a room temperature. The mixture was cooled down to −78° C., and a solution of 0.85 g (4.46 mmol) of titanium tetrachloride in 5 mL of heptane was dropped to the mixture. Temperature of the resultant mixture was raised up to a room temperature, and the mixture was stirred for 2 hours at 60° C. The obtained mixture was filtered with celite under a nitrogen atmosphere to remove impurities, and the filtrate was concentrated. Pentane was added to the concentrated filtrate, thereby obtaining 0.66 g (yield: 23.2%) of the complex (15) as a brown solid.

Its $^1$H-NMR (CDCl$_3$, δ (ppm)) showed the results: 1.04 (s, 3H), 1.07 to 1.40 (m, 10H), 1.19 (s, 9H), 1.24 (s, 3H), 1.27 (s, 9H), 1.43 (s, 3H), 1.47 (s, 3H), 1.66 to 1.78 (m, 4H), 2.43 (s, 3H), 7.15 (s, 1H), 7.28 (s, 1H), 7.55 (s, 1H), 7.58 (s, 1H), 7.65 (d, J=8.9 Hz, 1H), 8.15 (s, 1H), and 8.18 (d, J=8.9 Hz, 1H).

Its mass spectrum (EI, m/z) showed 697 (M$^+$) and 667.

Example 26

Synthesis of 2,2,5,5,8,8,11,11-octamethyl-2,3,4,5,8,9,10,11-octahydrodibenzofluorene There was obtained 2,2,5,5,8,8,11,11-octamethyl-2,3,4,5,8,9,10,11-octahydrodibenzofluorene according to a method similar to that disclosed in J. Am. Chem. Soc., 126, 16716 (2004).

Synthesis of (2-allyloxy-3-tert-butyl-5-methylphenyl)(2,2,5,5,8,8,11,11-octamethyl-2,3,4,5,8,9,10,11-octahydrodibenzofluoren-13-yl)diethylsilane There was dissolved 5.00 g (12.93 mmol) of 2,2,5,5,8,8,11,11-octamethyl-2,3,4,5,8,9,10,11-octahydrodibenzofluorene in 112 mL of THF, and the obtained solution was cooled down to −78° C. To the solution, 8.40 mL of a 1.54 M-concentration hexane solution of n-butyllithium was added slowly, 8.40 mL of said hexane solution containing 12.93 mmol of n-butyllithium. Temperature of the resultant mixture was raised up to a room temperature, and the mixture was stirred for 3 hours at a room temperature. The mixture was cooled down to −78° C., and a solution of 4.20 g (12.93 mmol) of (2-allyloxy-3-tert-butyl-5-methylphenyl)chlorodiethylsilane in 23 mL of toluene was added to the mixture. Temperature of the resultant mixture was raised up to a room temperature, and the mixture was stirred for 5 hours, thereby obtaining a reaction solution. A mixture of 50 mL of a 10% aqueous solution of sodium hydrogen carbonate and 50 mL of a 10% aqueous solution of sodium carbonate was added to the reaction solution at 0° C. To the obtained mixture, 58 mL of toluene was added, and the mixture was separated to the toluene solution and the aqueous solution. The toluene solution was dried over sodium sulfate, and the mixture was filtered. The obtained filtrate was concentrated under a reduced pressure, thereby obtaining quantitatively (2-allyloxy-3-tert-butyl-5-methylphenyl)(2,2,5,5,8,8,11,11-octamethyl-2,3,4,5,8,9,10,11-octahydrodibenzofluoren-13-yl)diethylsilane.

Its $^1$H-NMR (CDCl$_3$, δ (ppm)) showed the results: 0.52 to 0.91 (m, 10H), 1.12 (s, 6H), 1.17 (s, 6H), 1.20 to 1.74 (m, 8H), 1.34 (s, 6H), 1.35 (s, 6H), 1.41 (s, 9H), 2.28 (s, 3H), 4.32 (br s, 3H), 5.26 (d, J=10.9 Hz, 1H), 5.52 (d, J=17.5 Hz, 1H), 5.95 to 6.08 (m, 1H), 7.00 (s, 2H), 7.25 (br s, 2H), and 7.61 (s, 2H).

Its mass spectrum (FD, m/z) showed 674 (M$^+$).

Example 27

Synthesis of diethylsilylene(2,2,5,5,8,8,11,11-octamethyl-2,3,4,5,8,9,10,11-octahydrodibenzofluoren-13-yl)(3-tert-butyl-5-methyl-2-phenoxy)titanium dichloride (Referred to as "Complex (16)" Hereinafter)

There was dissolved 3.00 g (4.44 mmol) of (2-allyloxy-3-tert-butyl-5-methylphenyl)(2,2,5,5,8,8,11,11-octamethyl-2,3,4,5,8,9,10,11-octahydrodibenzofluoren-13-yl)diethylsilane in 54 mL of heptane, and 2.02 g (20.00 mmol) of triethylamine was added thereto. Temperature of the obtained mixture was cooled down to −78° C., and 6.49 mL of a 1.54 M-concentration hexane solution of n-butyllithium was added dropwise to the mixture, 6.49 mL of said hexane solution containing 10.00 mmol of n-butyllithium. Temperature of the resultant mixture was raised up to a room temperature, and the mixture was stirred for 3.5 hours at a room temperature. The mixture was cooled down to −78° C., and a solution of 1.26 g (6.67 mmol) of titanium tetrachloride in 7 mL of heptane was dropped to the mixture. Temperature of the resultant mixture was raised up to a room temperature, and the mixture was stirred for 3 hours at 90° C. The obtained mixture was filtered with celite under a nitrogen atmosphere to remove impurities, and the filtrate was concentrated. Pentane was added to the concentrated filtrate, thereby obtaining 0.54 g (yield: 16.3%) of the complex (16) as a brown solid.

Its $^1$H-NMR (CDCl$_3$, δ (ppm)) showed the results: 1.03 to 1.40 (m, 10H), 1.08 (s, 6H), 1.19 (s, 9H), 1.26 (s, 6H), 1.45 (s, 6H), 1.50 (s, 6H), 1.68 to 1.77 (m, 8H), 2.43 (s, 3H), 7.13 (s, 1H), 7.26 (s, 1H), 7.57 (s, 2H), and 8.14 (s, 2H).

Its mass spectrum (EI, m/z) showed 750 (M$^+$) and 721.

<Production of Ethylene-Cyclic Olefin Copolymer>

There were used the following methods for measuring physical properties.

(1) Amount of Vinylcyclohexane Unit Contained in Ethylene-Vinylcyclohexane Copolymer, and Amount of Tetracyclodecene Unit Contained in Ethylene-Tetracyclodecene Copolymer, Vinylcyclohexane and Tetracyclodecene Being Referred to Hereinafter as "VCH" and "DMON", Respectively The above-mentioned respective amounts were obtained by a method comprising the steps of (i) measuring a carbon nuclear magnetic resonance spectrum ($^{13}$C-NMR) under the following measurement condition, and (ii) calculating according to the following formula.

<Measurement Condition>
Apparatus: ARX400 manufactured by Bruker
Measurement solvent: mixed solvent containing 4 parts by volume of orthodichlorobenzene and 1 part by volume of orthodichlorobenzene-d4
Measurement temperature: 408K
Measurement method: Powergate Decoupling method
Pulse angle: 45°
Measurement reference: trimethylsilane <Calculation Formula>
Amount of VCH unit (% by mol)=100×A/(B−2A)
A: integrated value of signal of 45 ppm to 40 ppm
B: integrated value of signal of 35 ppm to 25 ppm
Amount of DMON unit (% by mol)=100×C/(D−4C)
C: integrated value of signal of 56 ppm to 50 ppm
D: integrated value of signal of 49 ppm to 15 ppm (2) Intrinsic Viscosity ([η], unit: dl/g)
It was measured at 135° C. in a TETRALINE solution using an Ubbellohde viscometer. The larger its value is, the larger a molecular weight is.

(3) Glass Transition Temperature, Melting Temperature
It was measured under the following condition using a differential scanning calorimeter, SSC-5200, manufactured by Seiko Instruments & Electronics Ltd.

Conditioning: heating from 20° C. up to 200° C. at the rate of temperature increase of 10° C./minute, retaining at 200° C., for 10 minutes, cooling from 200° C. down to −50° C. at the rate of temperature decrease of 10° C./minute, and retaining −50° C. for 10 minutes.

Measuring melting point: immediately after the conditioning, heating from −50° C. down to 200° C. at the rate of temperature increase of 10° C./minute.

Example 28

There were put 10.5 mL of VCH and 137 mL of dehydrated toluene in a 400 mL-autoclave purged with argon. The autoclave was heated up to 50° C., and ethylene was added thereto at its pressure of 0.8 MPa. There were added to the autoclave 1.1 mL of a toluene solution of triisobutylaluminum (referred to hereinafter as "TIBA"), the solution being manufactured by Tosoh-finechem and having an aluminum atom-concentration of 20.3% by weight, and a solution of 0.34 mg of the complex (12) in 0.7 mL of dehydrated toluene, in this order. There was further added thereto 1.5 mL of a toluene solution of N,N-dimethylaniliniumtetrakis(pentafluorophenyl)borate (referred to herein after as "AB"), said toluene solution having a concentration of 1.0 μmol/mL, and therefore 1.5 mL of said toluene solution containing 1.5 μmol of AB, thereby initiating polymerization. The mixture contained in the autoclave was agitated for 0.25 hour, and then 2 mL of ethanol was added to the mixture to terminate polymerization. The resultant reaction liquid was added to 1000 mL of acetone to form a white precipitate, which was filtered off. The white solid was washed with acetone, and dried under a reduced pressure, thereby obtaining 6.5 g of an ethylene-VCH copolymer. The copolymer had a VCH unit in an amount of 9.5% by mol, an intrinsic viscosity ([η]) of 2.16 dl/g, a glass transition temperature of −21.5° C., and a melting point of 68.1° C.

Example 29

Example 28 was repeated except that the amount of VCH was changed to 21.0 mL; the amount of dehydrated toluene was changed to 127 mL; and the agitation time was changed to 0.5 hour, thereby obtaining 10.7 g of an ethylene-VCH copolymer. The copolymer had a VCH unit in an amount of 16% by mol, an intrinsic viscosity ([η]) of 1.37 dl/g, a glass transition temperature of −23.4° C., and a melting point of 35.4° C.

Example 30

There were put 73.3 mL of VCH and 516 mL of dehydrated toluene in a 1000 mL-autoclave purged with argon. The autoclave was heated up to 50° C., and ethylene was added thereto at its pressure of 0.8 MPa. There were added to the autoclave 1.7 mL of a toluene solution of TIBA, the solution being manufactured by Tosoh-finechem and having an aluminum atom-concentration of 20.3% by weight, and a solution of 0.72 mg of the complex (13) in 0.72 mL of dehydrated toluene, in this order. There was further added thereto 3.0 mL of a toluene solution of AB, said toluene solution having a concentration of 1.0 μmol/mL, and therefore 3.0 mL of said toluene solution containing 3.0 μmol of AB, thereby initiating polymerization. The mixture contained in the autoclave was agitated for 3 hours, and then 5 mL of ethanol was added to the mixture to terminate polymerization. The resultant reaction liquid was mixed with 300 mL of hydrochloric acid having a concentration of 1% by weight in a separatory funnel, and the organic layer was separated. The separated organic layer was added to 2000 mL of acetone to form a white precipitate, which was filtered off. The white solid was washed with acetone, and dried under a reduced pressure, thereby obtaining 40 g of an ethylene-VCH copolymer. The copolymer had a VCH unit in an amount of 10.5% by mol, an intrinsic viscosity ([η]) of 1.37 dl/g, a glass transition temperature of −24° C., and a melting point of 60.1° C.

Example 31

Example 30 was repeated except that the amount of VCH was changed to 65.2 mL; 0.72 mg of the complex (13) was changed to 0.77 mg of the complex (16); and the agitation time was changed to 2 hours, thereby obtaining 43 g of an ethylene-VCH copolymer. The copolymer had a VCH unit in an amount of 9.3% by mol, an intrinsic viscosity ([η]) of 1.10 dl/g, a glass transition temperature of −23.1° C., and a melting point of 73.5° C.

Example 32

Example 28 was repeated except that the solution of 0.34 mg of the complex (12) in 0.7 mL of dehydrated toluene was changed to a solution of 1.4 mg of the complex (4) in 1.4 mL of dehydrated toluene; and the toluene solution of AB having a concentration of 1.0 μmol/mL was changed to 4.8 mg of AB powder, thereby obtaining 11.9 g of an ethylene-VCH copolymer. The copolymer had a VCH unit in an amount of 9% by mol, an intrinsic viscosity ([η]) of 0.89 dl/g, a glass transition temperature of −21.7° C., and a melting point of 80° C.

Example 33

Example 28 was repeated except that the amount of VCH was changed to 21.0 mL; the amount of dehydrated toluene was changed to 127 mL; the complex (12) was changed to 0.34 mg of the complex (4); and the agitation time was changed to 0.5 hour, thereby obtaining 9.18 g of an ethylene-VCH copolymer. The copolymer had a VCH unit in an amount of 13% by mol, an intrinsic viscosity ([η]) of 0.61 dl/g, a glass transition temperature of −26.4° C., and a melting point of 58° C.

Example 34

There were put 9.6 mL of DMON and 138 mL of dehydrated toluene in a 300 mL glass-made separable flask purged with argon. The flask was heated up to 50° C., and ethylene was added thereto. There were added to the flask 0.6 mL of a toluene solution of TIBA, the solution being manufactured by Tosoh-finechem and having an aluminum atom-concentration of 20.3% by weight, and a solution of 3.4 mg of the complex (12) in 1.7 mL of dehydrated toluene, in this order. There was further added thereto 12 mg of AB powder, thereby initiating polymerization. The mixture contained in the flask was agitated for 1 hour, and then 5 mL of ethanol was added to the mixture to terminate polymerization. The resultant reaction liquid was mixed with 100 mL of hydrochloric acid having a concentration of 1% by weight in a separatory funnel, and the organic layer was separated. The separated organic layer was added to 600 mL of acetone to form a white precipitate, which was filtered off. The white solid was washed with acetone, and dried under a reduced pressure, thereby obtaining 5.8 g of an ethylene-DMON copolymer. The copolymer had a DMON unit in an amount of 30% by mol, an intrinsic viscosity ([η]) of 1.90 dl/g, a glass transition temperature of 123° C., and no melting point.

Example 35

Example 34 was repeated except that the complex (12) was changed to the complex (4), thereby obtaining 0.9 g of an ethylene-DMON copolymer. The copolymer had a DMON unit in an amount of 31% by mol, an intrinsic viscosity ([η]) of 1.09 dl/g, a glass transition temperature of 130° C., and no melting point.

Comparative Example 1

Synthesis of dimethylsilylene(tetramethylcyclopentadienyl)(3-tert-butyl-5-methyl-2-phenoxy)titanium dichloride (Referred to as "Complex (R1)" Hereinafter)

The complex (R1) was obtained according to a method similar to that disclosed in JP 9-87313A.
Production of Ethylene-VCH Copolymer Example 28 was repeated except that the amount of the toluene solution of TIBA was changed to 0.46 mL; the solution of 0.34 mg of the complex (12) in 0.7 mL of dehydrated toluene was changed to a solution of 0.09 mg of the complex (R1) in 0.4 mL of dehydrated toluene; the amount of the toluene solution (concentration: 1.0 μmol/mL) of AB was changed to 0.6 mL (containing 0.6 μmol of AB); and the agitation time was changed to 0.5 hour, thereby obtaining 7.4 g of an ethylene-VCH copolymer. The copolymer had a VCH unit in an amount of 8.2% by mol, an intrinsic viscosity ([η]) of 0.55 dl/g, a glass transition temperature of −22.1° C., and a melting point of 84.1° C.

Comparative Example 2

Comparative Example 1 was repeated except that the amount of VCH was changed to 21.0 mL; and that the amount of the dehydrated toluene was changed to 127 mL, thereby obtaining 12.4 g of an ethylene-VCH copolymer. The copolymer had a VCH unit in an amount of 14.1% by mol, an intrinsic viscosity ([η]) of 0.34 dl/g, a glass transition temperature of −29.2° C., and a melting point of 50.5° C.

<Production of Ethylene-α-Olefin Copolymer (1)>

There were used the following methods for measuring physical properties.

(1) Amount of 1-Hexene Unit Contained in Copolymer (SCB, Unit: 1/1000 C)

The above-mentioned amount was obtained by an infrared spectroscopy using an infrared spectrometer, IR-810, manufactured by JASCO Corporation. There was used a peak of 1378 cm$^{-1}$ to 1303 cm$^{-1}$ as a characteristic absorption of a branched butyl group, and an amount of a 1-hexene unit was expressed by the number of the branched butyl group per 1000 carbon atoms contained in an ethylene-1-hexene copolymer.

(2) Intrinsic Viscosity ([7], Unit: dl/g)

It was measured at 135° C. in a TETRALINE solution using an Ubbellohde viscometer. The larger its value is, the larger a molecular weight is.

(3) Molecular Weight and Molecular Weight Distribution

They were measured by gel permeation chromatography (GPC) under the following conditions. A calibration curve was prepared using a standard polystyrene. The molecular weight distribution was evaluated by a ratio of Mw/Mn, wherein Mw is a weight average molecular weight, and Mn is a number average molecular weight.

Apparatus: Type 150C, manufactured by Milipore Waters Co.

Column: TSK-GEL GMH-HT (7.5 mmφ×660 mm), 2 columns, manufactured by Tosoh

Measurement temperature: 140° C.
Mobile phase: o-dichlorobenzene
Sample concentration: 5 mg/5 mL
Rate of flow: 1.0 mL/minute (4) Melting Point It was measured under the following condition using a differential scanning calorimeter, SSC-5200, manufactured by Seiko Instruments & Electronics Ltd.

Conditioning: heating from 40° C. up to 150° C. at the rate of temperature increase of 10° C./minute, retaining at 150° C. for 5 minutes, cooling from 150° C. down to 10° C. at the rate of temperature decrease of 5° C./minute, and retaining 10° C. for 10 minutes.

Measuring melting point: immediately after the conditioning, heating from 10° C. up to 160° C. at the rate of temperature increase of 5° C./minute.

Example 36

A 0.4 liter-inner volume autoclave equipped with a stirrer was vacuum-dried, and was charged with argon. There were put 185 mL of toluene as a solvent and 15 mL of 1-hexene as an α-olefin in the autoclave at room temperature, and the autoclave was heated up to 180° C. Ethylene was fed to the autoclave while keeping its pressure of 2.5 MPa. After stabilizing the system, there were added to the autoclave 0.30 mL (containing 0.30 mmol of TIBA) of a toluene solution of TIBA having a concentration of 1.0 mol/L, 0.5 mL (containing 0.50 μmol of the complex (1)) of a toluene solution of the complex (1) having a concentration of 1.0 μmol/mL, and 3.0 mL (containing 3.0 μmol of AB) of a toluene solution of AB having a concentration of 1.0 μmol/mL, thereby initiating polymerization. Polymerization was carried out for 2 minutes by feeding ethylene while regulating its partial pressure of 2.5 MPa and temperature of 180° C., thereby obtaining 2.96 g of an ethylene-1-hexene copolymer. A polymerization activity was 5.9×10$^6$ g/mol-Ti. The copolymer had SBC of 22/1000 C, an intrinsic viscosity ([η]) of 1.49 dl/g, Mw of 99000, Mw/Mn of 1.8, and a melting point of 96° C.

Example 37

Example 36 was repeated except that the toluene solution of the complex (1) was changed to 0.5 mL (containing 0.50 μmol of the complex (4)) of a toluene solution of the complex (4) having a concentration of 1.0 μmol/mL, thereby obtaining 3.39 g of an ethylene-1-hexene copolymer. A polymerization activity was 6.8×10$^6$ g/mol-Ti. The copolymer had SBC of 23/1000 C, an intrinsic viscosity ([η]) of 1.92 dl/g, Mw of 138000, Mw/Mn of 1.8, and melting points of 91° C. and 67° C.

Example 38

A 0.4 liter-inner volume autoclave equipped with a stirrer was vacuum-dried, and was charged with argon. There were put 185 mL of toluene as a solvent and 15 mL of 1-hexene as an α-olefin in the autoclave at room temperature, and the autoclave was heated up to 180° C. Ethylene was fed to the autoclave while keeping its pressure of 2.5 MPa. After stabilizing the system, there were added to the autoclave 0.30 mL (containing 0.30 mmol of TIBA) of a toluene solution of TIBA having a concentration of 1.0 mol/L, 0.50 mL (containing 0.50 μmol of the complex (4) and 25 μmol of TIBA) of a toluene solution containing both the complex (4) and TIBA having a complex (4)-concentration of 1.0 μmol/mL and a TIBA-concentration of 50 μmol/mL, and 3.0 mL (containing 3.0 μmol of AB) of a toluene solution of AB having a concentration of 1.0 μmol/mL, thereby initiating polymerization. Polymerization was carried out for 2 minutes by feeding ethylene while regulating its partial pressure of 2.5 MPa and temperature of 180° C., thereby obtaining 2.48 g of an ethylene-1-hexene copolymer. A polymerization activity was 5.0×10$^6$ g/mol-Ti. The copolymer had SBC of 27/1000 C, an intrinsic viscosity ([η]) of 2.18 dl/g, Mw of 170000, and Mw/Mn of 2.8.

Example 39

Example 38 was repeated except that the amount of toluene as a solvent was changed to 180 mL; and the amount of 1-hexene was changed to 20 mL, thereby obtaining 3.15 g of an ethylene-1-hexene copolymer. A polymerization activity was 6.3×10$^6$ g/mol-Ti. The copolymer had SBC of 31/1000 C, an intrinsic viscosity ([η]) of 1.59 dl/g, Mw of 120000, Mw/Mn of 2.0, and a melting point of 82° C.

Example 40

Example 38 was repeated except that the amount of toluene as a solvent was changed to 175 mL; and the amount of 1-hexene was changed to 25 mL, thereby obtaining 2.6 g of an ethylene-1-hexene copolymer. A polymerization activity was 5.2×10$^6$ g/mol-Ti. The copolymer had SBC of 36/1000 C, an intrinsic viscosity ([η]) of 1.42 dl/g, Mw of 100000, Mw/Mn of 1.9, and a melting point of 76° C.

Example 41

Example 38 was repeated except that the polymerization temperature was changed to 210° C., thereby obtaining 1.45 g of an ethylene-1-hexene copolymer. A polymerization activity was 2.9×10$^6$ g/mol-Ti. The copolymer had SBC of 20/1000 C, an intrinsic viscosity ([η]) of 1.34 dl/g, Mw of 86000, Mw/Mn of 2.1, and melting points of 100° C. and 115° C.

Example 42

Example 38 was repeated except that the polymerization temperature was changed to 210° C.; the amount of toluene as a solvent was changed to 175 mL; and the amount of 1-hexene was changed to 25 mL, thereby obtaining 1.4 g of an ethylene-1-hexene copolymer. A polymerization activity was $2.8 \times 10^6$ g/mol-Ti. The copolymer had SBC of 34/1000 C, an intrinsic viscosity ([η]) of 0.98 dl/g, Mw of 59000, Mw/Mn of 2.3, and melting points of 81° C. and 113° C.

Example 43

Preparation of Bi Compound

There were put 101 g (0.230 mmol) of triphenylbismuth and 500 mL of toluene in a 2-liter four-necked flask purged with argon. There was added dropwise 345 mL (containing 0.690 mmol of pentafluorophenol) of a toluene solution of pentafluorophenol having a concentration of 2.00 mol/L to the mixture at room temperature. The resultant mixture was stirred for 11 hours under a ref lux condition. The obtained mixture was allowed to stand at 0° C. to precipitate a yellow crystal. The yellow crystal was filtered off, and the obtained yellow crystal was dried under a reduced pressure, thereby obtaining 171 g of the dried yellow crystal.

There were put 15.3 g (20.2 mmol) of the dried yellow crystal and 100 mL of toluene in a 500 mL separable flask purged with argon. The mixture was heated up to 80° C. to dissolve the yellow crystal completely. There was added dropwise 363 μL (20.2 mmol) of water to the mixture over 10 minutes, and the resultant mixture was stirred at 80° C. for 1 hour, thereby precipitating white powder. The mixture was cooled down to a room temperature, and was allowed to stand, thereby settling out the precipitated white powder. The supernatant liquid was withdrawn from the flask, and the remaining white powder was washed with 40 mL of toluene one time, and then with each 40 mL of hexane two times. Volatile matters contained in the washed white powder were evaporated to dryness, thereby obtaining 6.24 g of a white compound (referred to hereinafter as "compound (c)").

Production of Ethylene-1-Hexene Copolymer

A 400 mL-inner volume autoclave equipped with a stirrer was vacuum-dried, and was charged with argon. There were put therein 185 mL of toluene as a solvent and 15 mL of 1-hexene as a comonomer, and the autoclave was heated up to 180° C. Ethylene was fed thereto while keeping its partial pressure of 2.5 MPa. After stabilizing the system, there were added thereto 0.3 mL (containing 300 μmol of TIBA) of a toluene solution of TIBA having a concentration of 1.0 mol/L, 0.5 mL (containing 0.5 μmol of the complex (4) and 25 μmol of TIBA) of a toluene solution containing both the complex (4) and TIBA having a complex (4)-concentration of 1.0 μmol/mL and a TIBA-concentration of 50 μmol/mL, and 5.0 mL of a toluene slurry of the compound (c) having a concentration of 4.98% by weight to initiate polymerization. Polymerization was carried out for 2 minutes, thereby obtaining 0.32 g of an ethylene-1-hexene copolymer. A polymerization activity was $0.64 \times 10^6$ g/mol-Ti/2 minutes. The copolymer had SBC of 25/1000 C, an intrinsic viscosity ([η]) of 2.38 dl/g, Mw of 190000, Mw/Mn of 1.9, and a melting point of 70° C.

Example 44

Example 38 was repeated except that the toluene solution containing both the complex (4) and TIBA was changed to 0.50 mL (containing 0.25 μmol of the complex (5) and 13 μmol of TIBA) of a toluene solution containing both the complex (5) and TIBA having a complex (5)-concentration of 0.5 μmol/mL and a TIBA-concentration of 25 μmol/mL, thereby obtaining 0.996 g of an ethylene-1-hexene copolymer. A polymerization activity was $4.0 \times 10^6$ g/mol-Ti. The copolymer had SBC of 22/1000 C, an intrinsic viscosity ([η]) of 2.18 dl/g, Mw of 160000, and Mw/Mn of 2.1.

Example 45

Example 38 was repeated except that the toluene solution containing both the complex (4) and TIBA was changed to 0.50 mL (containing 0.50 μmol of the complex (6) and 25 μmol of TIBA) of a toluene solution containing both the complex (6) and TIBA having a complex (6)-concentration of 1.0 μmol/mL and a TIBA-concentration of 50 μmol/mL, thereby obtaining 2.76 g of an ethylene-1-hexene copolymer. A polymerization activity was $5.5 \times 10^6$ g/mol-Ti. The copolymer had SBC of 22/1000 C, an intrinsic viscosity ([η]) of 2.03 dl/g, Mw of 150000, and Mw/Mn of 2.1.

Example 46

Example 38 was repeated except that the toluene solution containing both the complex (4) and TIBA was changed to 0.50 mL (containing 0.50 μmol of the complex (7) and 25 μmol of TIBA) of a toluene solution containing both the complex (7) and TIBA having a complex (7)-concentration of 1.0 μmol/mL and a TIBA-concentration of 50 μmol/mL, thereby obtaining 2.29 g of an ethylene-1-hexene copolymer. A polymerization activity was $4.6 \times 10^6$ g/mol-Ti. The copolymer had SBC of 23/1000 C, an intrinsic viscosity ([η]) of 2.09 dl/g, Mw of 150000, and Mw/Mn of 1.9.

Example 47

Example 38 was repeated except that the toluene solution containing both the complex (4) and TIBA was changed to 0.50 mL (containing 0.50 μmol of the complex (12) and 25 μmol of TIBA) of a toluene solution containing both the complex (12) and TIBA having a complex (12)-concentration of 1.0 μmol/mL and a TIBA-concentration of 50 μmol/mL, thereby obtaining 2.01 g of an ethylene-1-hexene copolymer. A polymerization activity was $4.0 \times 10^6$ g/mol-Ti. The copolymer had SBC of 27/1000 C, an intrinsic viscosity ([η]) of 1.64 dl/g, Mw of 150000, and Mw/Mn of 2.3.

Comparative Example 3

Synthesis of dimethylsilylene(tetramethylcyclopentadienyl)(3-tert-butyl-5-methyl-2-phenoxy)titanium dimethoxide (Referred to as "Complex (R2)" Hereinafter)

The complex (R2) was obtained according to a method similar to that disclosed in JP 2000-119287A.

Production of Ethylene-1-Hexene Copolymer

Example 38 was repeated except that the toluene solution containing both the complex (4) and TIBA was changed to 0.50 mL (containing 0.50 μmol of the complex (R2) and 25 μmol of TIBA) of a heptane solution containing both the complex (R2) and TIBA having a complex (R2)-concentration of 1.0 μmol/mL and a TIBA-concentration of 50 μmol/mL, thereby obtaining 4.59 g of an ethylene-1-hexene copolymer. A polymerization activity was $9.2 \times 10^6$ g/mol-Ti. The copolymer had SBC of 31/1000 C, an intrinsic viscosity ([η]) of 1.00 dl/g, Mw of 150000, and Mw/Mn of 2.3.

Comparative Example 4

Comparative Example 3 was repeated except that polymerization temperature was changed to 210° C.; and toluene as a solvent was changed to 185 mL of cyclohexane, thereby obtaining 0.85 g of an ethylene-1-hexene copolymer. A polymerization activity was $1.7 \times 10^6$ g/mol-Ti. The copolymer had SBC of 34/1000 C, an intrinsic viscosity ([η]) of 0.57 dl/g, Mw of 25000, and Mw/Mn of 2.6.

Comparative Example 5

Synthesis of 2,7-di-tert-butylfluorenyldimethylsilyl-tert-butylamidotitanium dichloride (Referred to as "Complex (R3)" Hereinafter)

The complex (R3) was obtained using 2,7-di-tert-butyl fluorene according to a method similar to that disclosed in WO 98/6727A.

Production of Ethylene-1-Hexene Copolymer

Example 36 was repeated except that the toluene solution of the complex (1) was changed to 0.5 mL (containing 0.50 μmol of the complex (R3)) of a toluene solution of the complex (R3) having a concentration of 1.0 μmol/mL, thereby obtaining no polymer.

<Production of Ethylene-α-Olefin Copolymer (2)>

The following items were measured.

(1) Amount of 1-Hexene Unit Contained in Copolymer (SCB, Unit: 1/1000 C)

The above-mentioned amount was obtained by an infrared spectroscopy using an infrared spectrometer, EQUINOX 55, manufactured by Bruker. There was used a peak of 1378 cm$^{-1}$ to 1303 cm$^{-1}$ as a characteristic absorption of a branched butyl group, and an amount of a 1-hexene unit was expressed by the number of the branched butyl group per 1000 carbon atoms contained in an ethylene-1-hexene copolymer.

(2) Molecular Weight and Molecular Weight Distribution

They were measured by gel permeation chromatography (GPC) under the following conditions. The molecular weight distribution was evaluated by a ratio of Mw/Mn, wherein Mw is a weight average molecular weight, and Mn is a number average molecular weight.

Apparatus: solution sending apparatus (LC pump), Model 1305 (pump head 25. SC) manufactured by Gilson Column: PL gel Mixed-B 10 μm (7.5 mmφ×300 mm) manufactured by Polymer Laboratories Measurement temperature: 160° C.

Mobile phase: o-dichlorobenzene

Sample concentration: 1 mg-copolymer/1 mL-1,2,4-tri chlorobenzene

Rate of flow: 2 mL/minute

Standard substance: (molecular weight of standard polystyrenes) 5,000; 10,050; 28,500; 65,500; 185,400; 483,000; 1,013,000; and 3,390,000

Examples 48 to 77

Copolymerization of ethylene and 1-hexene was carried out under the following polymerization condition by the use of respective complexes as a catalyst component for olefin polymerization using a PPR system manufactured by Symyx. Polymerization results are shown in Tables 1 to 9.

<Polymerization Condition>

(A-2)

There were put 5.0 mL of toluene and 50 μL of 1-hexexne in the autoclave in an atmosphere of nitrogen, and the system was stabilized at 70° C. Then, ethylene was pressed into the autoclave up to 0.60 MPa, and the system was stabilized. There were added to the autoclave 100 μmol (value corresponding to an amount of an aluminum atom) of aluminoxane, MMAO (containing 5.8% by weight of an aluminum atom), manufactured by Tosoh-finechem, and 0.10 μmol of the complex, and polymerization was carried out for 30 minutes.

(B-1)

There were put 5.0 mL of toluene and 60 μL of 1-hexexne in the autoclave in an atmosphere of nitrogen, and the system was stabilized at 40° C. Then, ethylene was pressed into the autoclave up to 0.60 MPa, and the system was stabilized. There were added to the autoclave 40 μL of a hexane solution of TIBA having a concentration of 1.0 mol/L manufactured by Kanto Chemical Co., Inc., 0.30 μmol of AB, and 0.10 μmol of the complex, and polymerization was carried out for 30 minutes.

(B-2)

There were put 5.0 mL of toluene and 50 μL of 1-hexexne in the autoclave in an atmosphere of nitrogen, and the system was stabilized at 70° C. Then, ethylene was pressed into the autoclave up to 0.60 MPa, and the system was stabilized. There were added to the autoclave 40 μL of a hexane solution of TIBA having a concentration of 1.0 mol/L manufactured by Kanto Chemical Co., Inc., 0.30 μmol of AB, and 0.10 μmol of the complex, and polymerization was carried out for 30 minutes.

(B-3)

There were put 5.0 mL of toluene and 40 μL of 1-hexexne in the autoclave in an atmosphere of nitrogen, and the system was stabilized at 130° C. Then, ethylene was pressed into the autoclave up to 0.60 MPa, and the system was stabilized. There were added to the autoclave 40 μL of a hexane solution of TIBA having a concentration of 1.0 mol/L manufactured by Kanto Chemical Co., Inc., 0.30 μmol of AB, and 0.10 μmol of the complex, and polymerization was carried out for 30 minutes.

(C-1)

There were put 5.0 mL of toluene and 60 μL of 1-hexexne in the autoclave in an atmosphere of nitrogen, and the system was stabilized at 40° C. Then, ethylene was pressed into the autoclave up to 0.60 MPa, and the system was stabilized. There were added to the autoclave 40 μL of a hexane solution of TIBA having a concentration of 1.0 mol/L manufactured by Kanto Chemical Co., Inc., 0.30 μmol of triphenylmethyltetrakis(pentafluorophenyl)borate (referred to as "CB" hereinafter), and 0.10 μmol of the complex, and polymerization was carried out for 30 minutes.

(C-2)

There were put 5.0 mL of toluene and 50 μL of 1-hexexne in the autoclave in an atmosphere of nitrogen, and the system was stabilized at 70° C. Then, ethylene was pressed into the autoclave up to 0.60 MPa, and the system was stabilized. There were added to the autoclave 40 μL of a hexane solution of TIBA having a concentration of 1.0 mol/L manufactured by Kanto Chemical Co., Inc., 0.30 μmol of CB, and 0.10 μmol of the complex, and polymerization was carried out for 30 minutes.

(C-3)

There were put 5.0 mL of toluene and 40 μL of 1-hexexne in the autoclave in an atmosphere of nitrogen, and the system was stabilized at 130° C. Then, ethylene was pressed into the autoclave up to 0.60 MPa, and the system was stabilized. There were added to the autoclave 40 μL of a hexane solution of TIBA having a concentration of 1.0 mol/L manufactured by Kanto Chemical Co., Inc., 0.30 μmol of CB, and 0.10 μmol of the complex, and polymerization was carried out for 30 minutes.

TABLE 1

| Example No. | Complex No. | Polymerization condition | SCB (1/1000 C) | Mw | Mw/Mn | Polymerization activity (g/mol-cat/hr) |
|---|---|---|---|---|---|---|
| 48 | (1) | A-2 | 11 | 359000 | 2.3 | $5.92 \times 10^7$ |
| 49 | (1) | B-1 | 22 | 1130000 | 2.8 | $4.30 \times 10^7$ |
| 50 | (1) | B-2 | 18 | 826000 | 2.8 | $4.40 \times 10^7$ |
| 51 | (1) | B-3 | 19 | 491000 | 1.9 | $0.87 \times 10^7$ |
| 52 | (1) | C-1 | 22 | 1180000 | 2.7 | $22.68 \times 10^7$ |
| 53 | (1) | C-2 | 18 | 819000 | 2.6 | $2.02 \times 10^7$ |
| 54 | (1) | C-3 | 24 | 404000 | 2.1 | $0.48 \times 10^7$ |

TABLE 2

| Example No. | Complex No. | Polymerization condition | SCB (1/1000 C) | Mw | Mw/Mn | Polymerization activity (g/mol-cat/hr) |
|---|---|---|---|---|---|---|
| 55 | (4) | A-2 | 13 | 461000 | 3.0 | $5.18 \times 10^7$ |
| 56 | (4) | B-1 | 23 | 1920000 | 2.6 | $11.52 \times 10^7$ |
| 57 | (4) | B-2 | 18 | 886000 | 2.8 | $2.40 \times 10^7$ |
| 58 | (4) | B-3 | 19 | 741000 | 2.1 | $1.05 \times 10^7$ |
| 59 | (4) | C-1 | 23 | 1990000 | 2.7 | $18.47 \times 10^7$ |
| 60 | (4) | C-2 | 20 | 1250000 | 2.9 | $2.18 \times 10^7$ |
| 61 | (4) | C-3 | 18 | 725000 | 2.1 | $0.80 \times 10^7$ |

TABLE 3

| Example No. | Complex No. | Polymerization condition | SCB (1/1000 C) | Mw | Mw/Mn | Polymerization activity (g/mol-cat/hr) |
|---|---|---|---|---|---|---|
| 62 | (9) | B-1 | 17 | 960000 | 2.9 | $8.40 \times 10^7$ |
| 63 | (9) | B-2 | 16 | 614000 | 2.7 | $3.74 \times 10^7$ |

TABLE 4

| Example No. | Complex No. | Polymerization condition | SCB (1/1000 C) | Mw | Mw/Mn | Polymerization activity (g/mol-cat/hr) |
|---|---|---|---|---|---|---|
| 64 | (10) | B-2 | 23 | 599000 | 2.7 | $1.77 \times 10^7$ |

TABLE 5

| Example No. | Complex No. | Polymerization condition | SCB (1/1000 C) | Mw | Mw/Mn | Polymerization activity (g/mol-cat/hr) |
|---|---|---|---|---|---|---|
| 65 | (11) | B-1 | 18 | 1035000 | 1.9 | $5.04 \times 10^7$ |

TABLE 6

| Example No. | Complex No. | Polymerization condition | SCB (1/1000 C) | Mw | Mw/Mn | Polymerization activity (g/mol-cat/hr) |
|---|---|---|---|---|---|---|
| 66 | (12) | B-1 | 14 | 849000 | 2.2 | $8.81 \times 10^7$ |
| 67 | (12) | B-2 | 16 | 366000 | 1.9 | $3.70 \times 10^7$ |
| 68 | (12) | B-3 | 23 | 299000 | 1.6 | $0.85 \times 10^7$ |
| 69 | (12) | C-1 | 16 | 1170000 | 1.8 | $11.40 \times 10^7$ |
| 70 | (12) | C-2 | 19 | 541000 | 1.9 | $3.10 \times 10^7$ |
| 71 | (12) | C-3 | 26 | 268000 | 1.6 | $0.67 \times 10^7$ |

TABLE 7

| Example No. | Complex No. | Polymerization condition | SCB (1/1000 C) | Mw | Mw/Mn | Polymerization activity (g/mol-cat/hr) |
|---|---|---|---|---|---|---|
| 72 | (13) | B-1 | 19 | 925000 | 2.1 | $2.02 \times 10^7$ |
| 73 | (13) | B-2 | 12 | 452000 | 2.2 | $3.33 \times 10^7$ |

TABLE 8

| Example No. | Complex No. | Polymerization condition | SCB (1/1000 C) | Mw | Mw/Mn | Polymerization activity (g/mol-cat/hr) |
|---|---|---|---|---|---|---|
| 74 | (15) | B-1 | 25 | 1025000 | 1.9 | $3.25 \times 10^7$ |
| 75 | (15) | B-2 | 10 | 486000 | 2.3 | $3.32 \times 10^7$ |

TABLE 9

| Example No. | Complex No. | Polymerization condition | SCB (1/1000 C) | Mw | Mw/Mn | Polymerization activity (g/mol-cat/hr) |
|---|---|---|---|---|---|---|
| 76 | (16) | B-1 | 30 | 1355000 | 2.7 | $0.83 \times 10^7$ |
| 77 | (16) | B-2 | 17 | 586000 | 2.2 | $3.55 \times 10^7$ |

Comparative Examples 6 to 12

Copolymerization of ethylene and 1-hexene was carried out under the above-mentioned polymerization condition by the use of the complex (R1) as a catalyst component for olefin polymerization using a PPR system manufactured by Symyx. Polymerization results are shown in Table 10.

TABLE 10

| Comparative Example No. | Complex No. | Polymerization condition | SCB (1/1000 C) | Mw | Mw/Mn | Polymerization activity (g/mol-cat/hr) |
|---|---|---|---|---|---|---|
| 6 | (R1) | A-2 | 23 | 128000 | 3.2 | $1.43 \times 10^7$ |
| 7 | (R1) | B-1 | 19 | 654000 | 2.6 | $2.63 \times 10^7$ |
| 8 | (R1) | B-2 | 28 | 260000 | 2.5 | $15.23 \times 10^7$ |
| 9 | (R1) | B-3 | 24 | 169000 | 2.1 | $3.08 \times 10^7$ |
| 10 | (R1) | C-1 | 17 | 535000 | 6.7 | $5.91 \times 10^7$ |
| 11 | (R1) | C-2 | 12 | 357000 | 3.6 | $7.53 \times 10^7$ |
| 12 | (R1) | C-3 | 28 | 189000 | 2.7 | $0.95 \times 10^7$ |

INDUSTRIAL APPLICABILITY

According to the present invention, there can be provided a transition metal complex, whose use as a catalyst component for olefin polymerization can polymerize an olefin to produce a high molecular weight olefin polymer; a catalyst component for olefin polymerization comprising said transition metal complex; a catalyst for olefin polymerization using said transition metal complex as a catalyst component for olefin polymerization; a process for producing an olefin polymer comprising the step of polymerizing an olefin in the presence of said catalyst for olefin polymerization; a process for producing said transition metal complex; a substituent-carrying fluorene compound usable for producing said transition metal complex; a process for producing said substituent-carrying fluorene compound; and a process for producing said transition metal complex using said substituent-carrying fluorene compound.

The invention claimed is:
1. A transition metal complex represented by the general formula [1]:

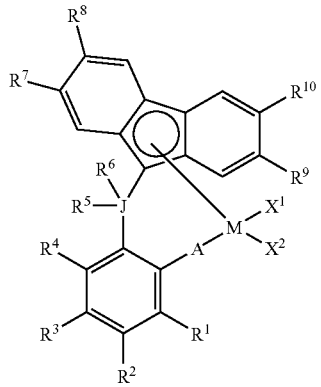

[1]

wherein M is a group 4 transition metal atom in the periodic table of elements; A is a group 16 atom therein; J is a group 14 atom therein; $R^1, R^2, R^3, R^4, R^5, R^6, X^1$ and $X^2$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^1$ and $R^2$, $R^2$ and $R^3$, and $R^3$ and $R^4$ may be linked to each other, respectively, to form respective rings; $R^5$ and $R^6$ may be linked to each other to form a ring; $R^7$ and $R^8$ are independently of each other (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, wherein $R^7$ and $R^8$ are linked to each other to form a ring; $R^9$ and $R^{10}$ are independently of each other (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; and $R^9$ and $R^{10}$ may be linked to each other to form a ring.

2. The transition metal complex according to claim 1, wherein at least one of $R^5$ and $R^6$ is an ethyl group.

3. The transition metal complex according to claim 1, wherein J is a silicon atom or a germanium atom.

4. A catalyst component for olefin polymerization, which comprises a transition metal complex of claim 1.

5. A catalyst for olefin polymerization obtained by contacting a catalyst component for olefin polymerization of claim 4 with the following compound (A) and/or compound (B):

(A) one or more kinds of aluminum compounds selected from the group consisting of the following (A1) to (A3),
  (A1) an organoaluminum compound represented by the general formula, $E^1{}_a AlZ_{3-a}$,
  (A2) a cyclic aluminoxane having a structure represented by the general formula, $\{Al(E^2)\text{-O—}\}_b$, and
  (A3) a linear aluminoxane having a structure represented by the general formula, $E^3\{\text{-Al}(E^3)\text{-O—}\}_c AlE^3{}_2$ wherein a is a number satisfying $0 < a \leq 3$; b is an integer of 2 or more; c is an integer of 1 or more; $E^1$, $E^2$ and $E^3$ are independently of one another a hydrocarbyl group having 1 to 20 carbon atoms, and plural $E^1$s, $E^2$s and $E^3$s are the same as or different from one another, respectively; and Z is a hydrogen atom or a halogen atom, and plural Zs are the same as or different from one another, (B) one or more kinds of boron compounds selected from the group consisting of the following (B1) to (B3),
  (B1) a boron compound represented by the general formula, $BQ^1Q^2Q^3$,
  (B2) a boron compound represented by the general formula, $G^+(BQ^1Q^2Q^3Q^4)$, and
  (B3) a boron compound represented by the general formula, $(L^1\text{-H})^+(BQ^1Q^2Q^3Q^4)$, wherein B is a trivalent boron atom; $Q^1$, $Q^2$, $Q^3$ and $Q^4$ are independently of one another a halogen atom, a hydrocarbyl group, a halogenated hydrocarbyl group, a substituent-carrying silyl group, an alkoxy group, or a di-substituent-carrying amino group; $G^+$ is an inorganic or organic cation; and $L^1$ is a neutral Lewis base.

6. A process for producing an olefin polymer, which comprises the step of polymerizing an olefin in the presence of the catalyst for olefin polymerization of claim 5.

7. A process for producing an ethylene-α-olefin copolymer, which comprises the step of polymerizing ethylene and an α-olefin in the presence of the catalyst for olefin polymerization of claim 5.

8. A process for producing an ethylene-cyclic olefin copolymer, which comprises the step of polymerizing ethylene and a cyclic olefin in the presence of the catalyst for olefin polymerization of claim 5.

9. A process for producing a transition metal complex of claim 1, which comprises the steps of:
  (1) reacting a substituent-carrying fluorene compound represented by the general formula [2] with a base; and
  (2) further reacting with a transition metal compound represented by the general formula [3],

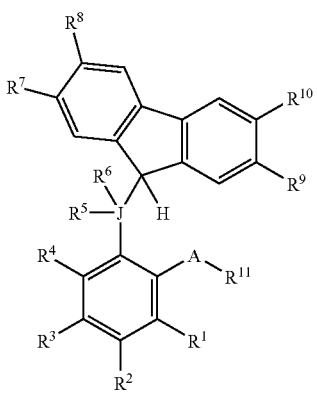

[2]

wherein A is a group 16 atom in the periodic table of elements; J is a group 14 atom therein; $R^1$, $R^2$, $R^3$, $R^4$, $R^5$ and $R^6$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^6$ is an ethyl group; $R^1$ and $R^2$, $R^2$ and $R^3$, and $R^3$ and $R^4$ may be linked to each other, respectively, to form respective rings; $R^5$ and $R^6$ may be linked to each other to form a ring; $R^7$ and $R^8$ are independently of each other (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, wherein $R^7$ and $R^8$ are linked to each other to form a ring; $R^9$ and $R^{10}$ are independently of each other (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^9$ and $R^{10}$ may be linked to each other to form a ring; and $R^{11}$ is a hydrocarbyl group or a three substituent-carrying silyl group, and $$M\text{-}X^3_n \qquad [3],$$

wherein M is a group 4 transition metal atom in the periodic table of elements; n is an integer of 3 or 4; $X^3$ is (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying amino group having 1 to 20 carbon atoms, which substituent is a hydrocarbyl group, and said hydrocarbyl group may be substituted by a halogen atom, (1-5) an alkoxy group having 1 to 20 carbon atoms, which may be substituted by a halogen atom, (1-6) an aralkyloxy group having 7 to 20 carbon atoms, which may be substituted by a halogen atom, and (1-7) an aryloxy group having 6 to 20 carbon atoms, which may be substituted by a halogen atom, (2) a halogen atom or (3) a hydrogen atom; and plural $X^3$s are the same as, or different from one another.

10. The process for producing a transition metal complex according to claim 9, wherein J is a silicon atom or a germanium atom.

11. A substituent-carrying fluorene compound represented by the general formula [2]:

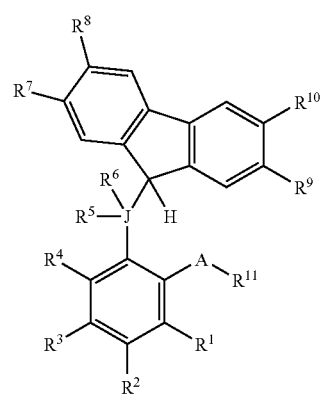

[2]

wherein A is a group 16 atom in the periodic table of elements; J is a group 14 atom therein; $R^1$, $R^2$, $R^3$, $R^4$, $R^5$ and $R^6$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^6$ is an ethyl group; $R^1$ and $R^2$, $R^2$ and $R^3$, and $R^3$ and $R^4$ may be linked to each other, respectively, to form respective rings; $R^5$ and $R^6$ may be linked to each other to form a ring; $R^7$ and $R^8$ are independently of each other (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, wherein $R^7$ and $R^8$ are linked to each other to form a ring; $R^9$ and $R^{10}$ are independently of each other (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^9$ and $R^{10}$ may be linked to each other to form a ring; and $R^{11}$ is a hydrocarbyl group or a three substituent-carrying silyl group.

12. The substituent-carrying fluorene compound according to claim 11, wherein J is a silicon atom or a germanium atom.

13. A process for producing a substituent-carrying fluorene compound of claim 11, which comprises the steps of:

(1) reacting a substituent-carrying fluorene compound represented by the general formula [4] with a base; and (2) further reacting with a compound represented by the general formula [5],

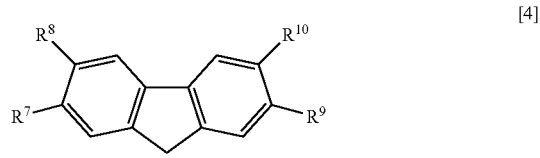

[4]

wherein $R^7$ and $R^8$ are independently of each other (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, wherein $R^7$ and $R^8$ are linked to each other to form a ring; $R^9$ and $R^{10}$ are independently of each other (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; and $R^9$ and $R^{10}$ may be linked to each other to form a ring; and

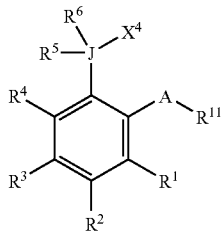

[5]

wherein A is a group 16 atom in the periodic table of elements; J is a group 14 atom therein; $R^1, R^2, R^3, R^4, R^5$ and $R^6$ are independently of one another (1) a substituent selected from the group consisting of (1-1) an alkyl group having 1 to 20 carbon atoms, which may be substituted by a halogen atom, (1-2) an aralkyl group having 7 to 20 carbon atoms, which may be substituted by a halogen atom, (1-3) an aryl group having 6 to 20 carbon atoms, which may be substituted by a halogen atom, (1-4) a substituent-carrying silyl group having 1 to 20 carbon atoms, which substituent is a hydrocarbyl group, and said hydrocarbyl group may be substituted by a halogen atom, (1-5) a disubstituent-carrying amino group having 2 to 20 carbon atoms, which substituent is a hydrocarbyl group, and said hydrocarbyl group may be substituted by a halogen atom, (1-6) an alkoxy group having 1 to 20 carbon atoms, which may be substituted by a halogen atom, (1-7) an aralkyloxy group having 7 to 20 carbon atoms, which may be substituted by a halogen atom, and (1-8) an aryloxy group having 6 to 20 carbon atoms, which may be substituted by a halogen atom, (2) a halogen atom or (3) a hydrogen atom; $R^1$ and $R^2$, $R^2$ and $R^3$, and $R^3$ and $R^4$ may be linked to each other, respectively, to form respective rings; $R^5$ and $R^6$ may be linked to each other to form a ring; $R^{11}$ is a hydrocarbyl group or a three substituent-carrying silyl group; and $X^4$ is a halogen atom.

14. The process for producing a substituent-carrying fluorene compound according to claim 13, wherein J is a silicon atom or a germanium atom.

* * * * *